(12) United States Patent
Heo et al.

(10) Patent No.: US 12,137,608 B2
(45) Date of Patent: Nov. 5, 2024

(54) COMPOUND AND ORGANIC LIGHT EMITTING DEVICE COMPRISING THE SAME

(71) Applicant: LG CHEM, LTD., Seoul (KR)

(72) Inventors: Dong Uk Heo, Daejeon (KR); Sung Kil Hong, Daejeon (KR); Jungoh Huh, Daejeon (KR); Miyeon Han, Daejeon (KR); Jae Tak Lee, Daejeon (KR); Junghoon Yang, Daejeon (KR)

(73) Assignee: LG CHEM, LTD., Seoul (KR)

( * ) Notice: Subject to any disclaimer, the term of this patent is extended or adjusted under 35 U.S.C. 154(b) by 575 days.

(21) Appl. No.: 17/261,795

(22) PCT Filed: Nov. 11, 2019

(86) PCT No.: PCT/KR2019/015274
§ 371 (c)(1),
(2) Date: Jan. 20, 2021

(87) PCT Pub. No.: WO2020/101305
PCT Pub. Date: May 22, 2020

(65) Prior Publication Data
US 2021/0280794 A1    Sep. 9, 2021

(30) Foreign Application Priority Data

Nov. 13, 2018 (KR) .................. 10-2018-0139107
Nov. 8, 2019 (KR) .................. 10-2019-0142731

(51) Int. Cl.
| | | |
|---|---|---|
| C07D 251/24 | (2006.01) | |
| C07D 401/10 | (2006.01) | |
| C07D 405/10 | (2006.01) | |
| C07D 409/10 | (2006.01) | |
| H10K 85/60 | (2023.01) | |
| H10K 50/16 | (2023.01) | |

(52) U.S. Cl.
CPC ......... *H10K 85/654* (2023.02); *C07D 251/24* (2013.01); *C07D 401/10* (2013.01); *C07D 405/10* (2013.01); *C07D 409/10* (2013.01); *H10K 85/6574* (2023.02); *H10K 85/6576* (2023.02); *H10K 50/16* (2023.02)

(58) Field of Classification Search
None
See application file for complete search history.

(56) References Cited

U.S. PATENT DOCUMENTS

| | | | |
|---|---|---|---|
| 2004/0251816 A1 | 12/2004 | Leo et al. | |
| 2015/0171336 A1* | 6/2015 | Park ................. | C07D 403/04 257/40 |
| 2016/0118599 A1* | 4/2016 | Jeong ................ | H10K 85/6572 546/276.7 |
| 2017/0222157 A1* | 8/2017 | Jatsch ................. | C07D 405/14 |
| 2018/0013072 A1 | 1/2018 | Eum et al. | |
| 2018/0127385 A1 | 5/2018 | Jung et al. | |
| 2019/0214571 A1* | 7/2019 | Huh ..................... | C07D 405/10 |
| 2019/0292169 A1* | 9/2019 | Park ..................... | H10K 85/654 |
| 2019/0296243 A1* | 9/2019 | Suh ...................... | H10K 85/615 |
| 2020/0227646 A1* | 7/2020 | Jung .................... | H10K 85/6574 |
| 2020/0317646 A1* | 10/2020 | He ....................... | H10K 85/615 |
| 2022/0289693 A1* | 9/2022 | Lee ...................... | H10K 85/622 |

FOREIGN PATENT DOCUMENTS

| | | |
|---|---|---|
| KR | 10-2000-0051826 A | 8/2000 |
| KR | 10-2015-0136032 A | 12/2015 |
| KR | 10-2016-0078238 A | 7/2016 |
| KR | 10-2017-0113342 A | 10/2017 |
| KR | 10-2017-0116944 A | 10/2017 |
| KR | 10-2017-0116992 A | 10/2017 |
| KR | 10-2017-0126691 A | 11/2017 |
| KR | 10-2017-0134264 A | 12/2017 |
| KR | 10-2018-0022190 A | 3/2018 |
| KR | 10-2018-0043744 A | 4/2018 |
| KR | 10-2018-0103021 A | 9/2018 |
| WO | 2003-012890 A2 | 2/2003 |
| WO | 2016-105050 A1 | 6/2016 |
| WO | 2016-105141 A2 | 6/2016 |
| WO | 2016-182388 A2 | 11/2016 |
| WO | 2017-171376 A1 | 10/2017 |
| WO | 2017-179911 A1 | 10/2017 |
| WO | WO-2017171375 A1 * | 10/2017 ............. C07C 13/62 |
| WO | WO-2018038401 A1 * | 3/2018 ........... C07D 221/20 |
| WO | 2018-074881 A1 | 4/2018 |

OTHER PUBLICATIONS

Machine translation of WO-2018038401, translation generated May 2023, 35 pages. (Year: 2023).*
Machine translation of WO-2017171375, translation generated May 2023, 17 pages. (Year: 2023).*
Machine translation of WO 2018/038401, translation generated Sep. 2023, 35 pages. (Year: 2023).*

* cited by examiner

*Primary Examiner* — Robert S Loewe
(74) *Attorney, Agent, or Firm* — Bryan Cave Leighton Paisner LLP

(57) ABSTRACT

A novel compound represented by the following Chemical Formula 1, and an organic light emitting device including the same.

Chemical Formula 1

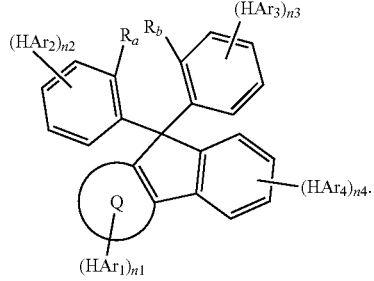

14 Claims, 1 Drawing Sheet

[FIG. 1]
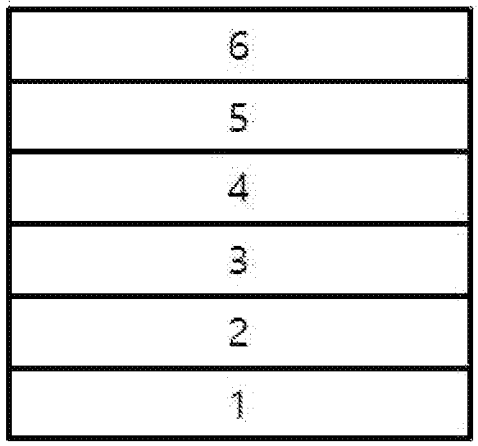
[FIG. 2]
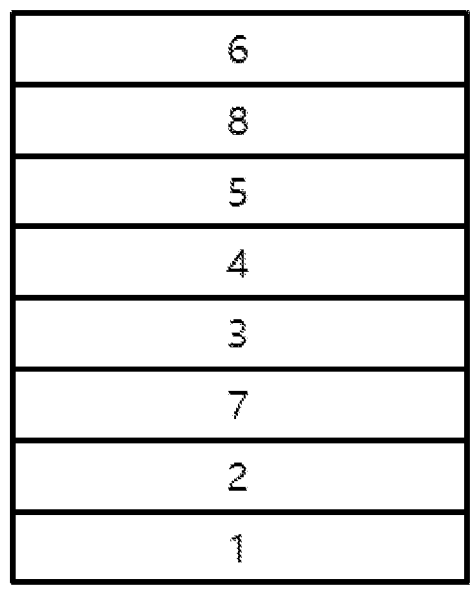

COMPOUND AND ORGANIC LIGHT EMITTING DEVICE COMPRISING THE SAME

CROSS-REFERENCE TO RELATED APPLICATION(S)

This application is a National Stage Application of International Application No. PCT/KR2019/015274 filed on Nov. 11, 2019, which claims the benefits of the filing dates of Korean Patent Application No. 10-2018-0139107 filed with the Korean Intellectual Property Office on Nov. 13, 2018, and Korean Patent Application No. 10-2019-0142731 filed with the Korean Intellectual Property Office on Nov. 8, 2019, the entire contents of which are incorporated herein by reference.

TECHNICAL FIELD

The present disclosure relates to novel compounds and organic light emitting devices including the same.

BACKGROUND

In general, an organic light emitting phenomenon refers to a phenomenon where electrical energy is converted into light energy by using an organic material. The organic light emitting device using the organic light emitting phenomenon has characteristics such as a wide viewing angle, excellent contrast, a fast response time, and excellent luminance, driving voltage, and response speed, and thus many studies have proceeded thereon.

The organic light emitting device generally has a structure which includes an anode, a cathode, and an organic material layer interposed between the anode and the cathode. The organic material layer frequently has a multilayered structure that includes different materials in order to enhance efficiency and stability of the organic light emitting device, and for example, the organic material layer may be formed of a hole injection layer, a hole transport layer, a light emitting layer, an electron transport layer, an electron injection layer, and the like. In the structure of the organic light emitting device, if a voltage is applied between two electrodes, holes are injected from an anode into the organic material layer and electrons are injected from the cathode into the organic material layer, and when the injected holes and electrons meet each other, an exciton is formed, and light is emitted when the exciton falls to a ground state again.

There is a continuing need for the development of new materials for the organic materials used in these organic light emitting devices.

PRIOR ART LITERATURE (Patent Literature 0001) Korean Patent Laid-open Publication No. 10-2000-0051826

Technical Problem

It is an object of the present invention to provide a novel compound and an organic light emitting device including the same.

Technical Solution

In one aspect of the present disclosure, there is provided a compound represented by the following Chemical Formula 1.

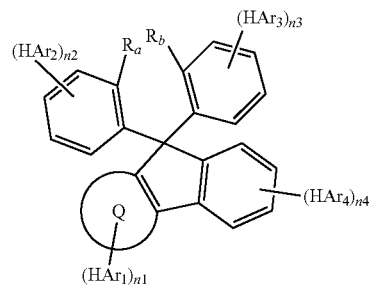

Chemical Formula 1 wherein, in Chemical Formula 1,
Q is naphthalene,
$R_a$ and $R_b$ are each hydrogen, or are bonded to each other to form Y,
Y is single bond, O, or S,
one of $HAr_1$ to $HAr_4$ is the following Chemical Formula 2, one of the others is the following Chemical Formula 3, and the rest are each independently Chemical Formula 2 or 3,

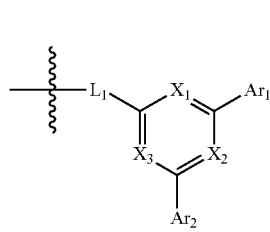

Chemical Formula 2

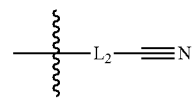

Chemical Formula 3 wherein, in Chemical Formula 2 and 3,
$L_1$ and $L_2$ are each independently a single bond; or a substituted or unsubstituted $C_{6-60}$ arylene,
$X_1$ to $X_3$ are each independently N or CR, and at least two of $X_1$ to $X_3$ are N,
$Ar_1$ and $Ar_2$ are each independently a substituted or unsubstituted $C_{6-60}$ aryl; or a substituted or unsubstituted $C_{2-60}$ heteroaryl containing one or more heteroatoms selected from the group consisting of N, O, and S,
R is hydrogen; deuterium; a substituted or unsubstituted $C_{1-60}$ alkyl; a substituted or unsubstituted $C_{3-60}$ cycloalkyl; a substituted or unsubstituted $C_{6-60}$ aryl; or a substituted or unsubstituted $C_{2-60}$ heteroaryl containing one or more heteroatoms selected from the group consisting of N, O, and S,
n1 to n4 are each an integer of 0 to 2,
n1+n2+n3+n4 is an integer of 2 to 8, and
when n1 to n4 are 2 or more, the structures in parentheses are the same as or different from each other.

In another aspect of the present disclosure, there is provided an organic light emitting device including: a first electrode; a second electrode provided to face the first electrode; and one or more organic material layers provided between the first electrode and the second electrode, wherein one or more layers of the organic material layers include the compound represented by Chemical Formula 1.

Advantageous Effects

The compound represented by Chemical Formula 1 described above can be used as a material of an organic material layer of an organic light emitting device, and may improve efficiency, achieve a low driving voltage, and/or improve lifespan characteristics of the organic light emitting device.

BRIEF DESCRIPTION OF DRAWINGS

FIG. 1 shows an example of an organic light emitting device including a substrate 1, an anode 2, a hole transport layer 3, a light emitting layer 4, an electron injection and transport layer 5, and a cathode 6.

FIG. 2 shows an example of an organic light emitting device including a substrate 1, an anode 2, a hole injection layer 7, a hole transport layer 3, a light emitting layer 4, an electron injection and transport layer 5, and a cathode 6.

DETAILED DESCRIPTION

Hereinafter, the present disclosure will be described in more detail to help understanding of the present disclosure.

In the present specification,

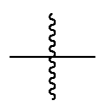

means a bond connected to another substituent group.

As used herein, the term "substituted or unsubstituted" means being unsubstituted or substituted with one or more substituents selected from the group consisting of deuterium; a halogen group; a cyano group; a nitro group; a hydroxy group; a carbonyl group; an ester group; an imide group; an amino group; a phosphine oxide group; an alkoxy group; an aryloxy group; an alkylthioxy group; an arylthioxy group; an alkylsulfoxy group; an arylsulfoxy group; a silyl group; a boron group; an alkyl group; a cycloalkyl group; an alkenyl group; an aryl group; an aralkyl group; an aralkenyl group; an alkylaryl group; an alkylamine group; an aralkylamine group; a heteroarylamine group; an arylamine group; an arylphosphine group; and a hetero-cyclic group containing at least one of N, O, and S atoms, or being unsubstituted or substituted with a substituent to which two or more substituents are linked among the substituents exemplified above. For example, "the substituent to which two or more substituents are linked" may be a biphenyl group. That is, the biphenyl group may also be an aryl group, and may be interpreted as a substituent to which two phenyl groups are linked.

As used herein, the number of carbon atoms of a carbonyl group is not particularly limited, but is preferably 1 to 40. Specifically, the carbonyl group may be a compound having the following structural formulae, but is not limited thereto.

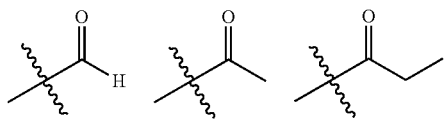

-continued

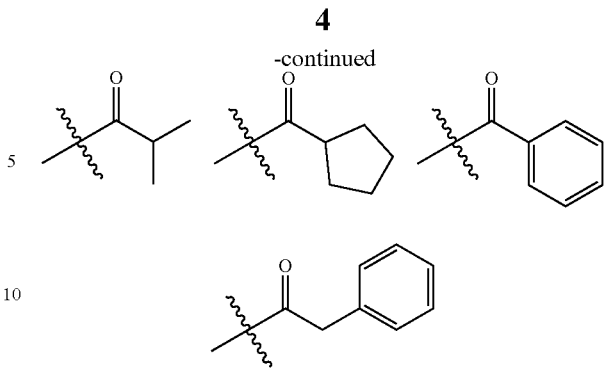

As used herein, an ester group may have a structure in which oxygen of the ester group may be substituted by a straight-chain, branched-chain, or cyclic alkyl group having 1 to 25 carbon atoms, or an aryl group having 6 to 25 carbon atoms. Specifically, the ester group may be a compound having the following structural formulae, but is not limited thereto.

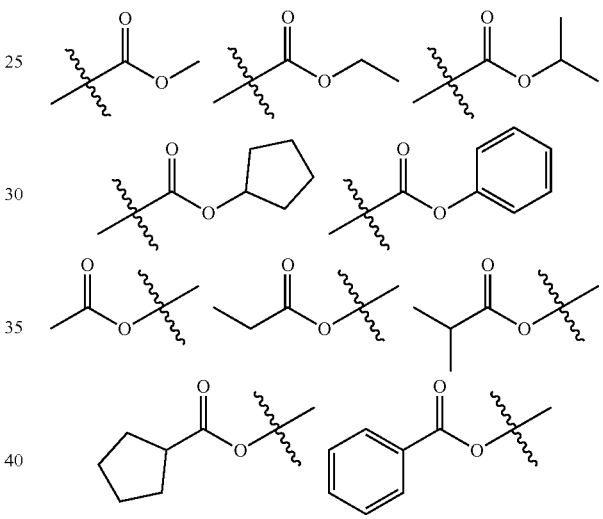

As used herein, the number of carbon atoms of an imide group is not particularly limited, but is preferably 1 to 25. Specifically, the imide group may be a compound having the following structural formulae, but is not limited thereto.

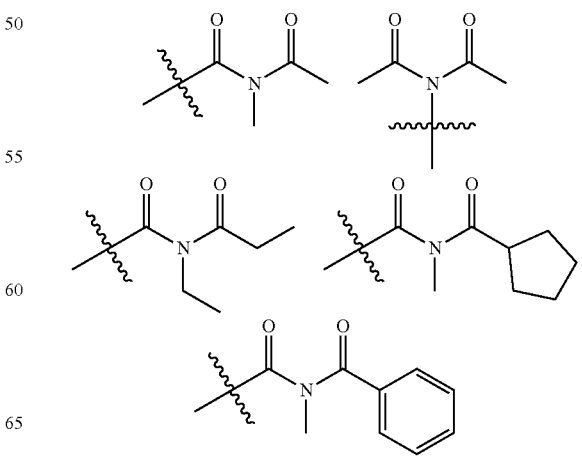

As used herein, a silyl group specifically includes a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but is not limited thereto.

As used herein, a boron group specifically includes a trimethylboron group, a triethylboron group, a t-butyldimethylboron group, a triphenylboron group, and a phenylboron group, but is not limited thereto.

As used herein, examples of a halogen group include fluorine, chlorine, bromine, and iodine.

As used herein, the alkyl group may be a straight chain or branched chain, and the number of carbon atoms thereof is not particularly limited, but is preferably 1 to 40. According to one embodiment, the number of carbon atoms of the alkyl group is 1 to 20. According to another embodiment, the number of carbon atoms of the alkyl group is 1 to 10. According to a further embodiment, the number of carbon atoms of the alkyl group is 1 to 6. Specific examples of the alkyl group include methyl, ethyl, propyl, n-propyl, isopropyl, butyl, n-butyl, isobutyl, tert-butyl, sec-butyl, 1-methylbutyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethylpropyl, 1,1-dimethyl-propyl, isohexyl, 2-methylpentyl, 4-methylhexyl, 5-methylhexyl, and the like, but are not limited thereto.

As used herein, the alkenyl group may be a straight chain or branched chain, and the number of carbon atoms thereof is not particularly limited, but is preferably 2 to 40. According to one embodiment, the number of carbon atoms of the alkenyl group is 2 to 20. According to another embodiment, the number of carbon atoms of the alkenyl group is 2 to 10. According to still another embodiment, the number of carbon atoms of the alkenyl group is 2 to 6. Specific examples thereof include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group, and the like, but are not limited thereto.

As used herein, a cycloalkyl group is not particularly limited, but the number of carbon atoms thereof is preferably 3 to 60. According to one embodiment, the number of carbon atoms of the cycloalkyl group is 3 to 30. According to another embodiment, the number of carbon atoms of the cycloalkyl group is 3 to 20. According to still another embodiment, the number of carbon atoms of the cycloalkyl group is 3 to 6. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

As used herein, an aryl group is not particularly limited, but preferably has 6 to 60 carbon atoms, and may be a monocyclic aryl group or a polycyclic aryl group. According to one embodiment, the number of carbon atoms of the aryl group is 6 to 30. According to one embodiment, the number of carbon atoms of the aryl group is 6 to 20. The aryl group may be a phenyl group, a biphenyl group, a terphenyl group, or the like as the monocyclic aryl group, but is not limited thereto. Examples of the polycyclic aryl group include a naphthyl group, an anthracenyl group, a phenanthryl group, a pyrenyl group, a perylenyl group, a chrysenyl group, a fluorenyl group, or the like, but are not limited thereto.

As used herein, a fluorenyl group may be substituted, and two substituent groups may be bonded to each other to form a spiro structure. In the case where the fluorenyl group is substituted,

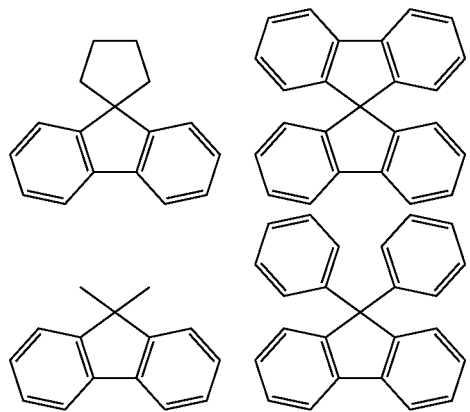

and the like can be formed. However, the structure is not limited thereto.

As used herein, a heteroaryl is a heteroaryl including one or more of O, N, Si, and S as a heteroatom, and the number of carbon atoms thereof is not particularly limited, but is preferably 2 to 60. Examples of the heteroaryl include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazole group, a benzocarbazole group, a benzothiophene group, a dibenzothiophene group, a benzofuranyl group, a phenanthroline group, an isoxazolyl group, a thiadiazolyl group, a phenothiazinyl group, a dibenzofuranyl group, and the like, but are not limited thereto.

As used herein, the aryl group in the aralkyl group, the aralkenyl group, the alkylaryl group, and the arylamine group is the same as the aforementioned examples of the aryl group. In the present specification, the alkyl group in the aralkyl group, the alkylaryl group, and the alkylamine group is the same as the aforementioned examples of the alkyl group. In the present specification, for the heteroaryl in the heteroarylamine group the aforementioned description of the heterocyclic group can be applied. In the present specification, the alkenyl group in the aralkenyl group is the same as the aforementioned examples of the alkenyl group. In the present specification, the aforementioned description of the aryl group may be applied except that the arylene is a divalent group. In the present specification, the aforementioned description of the heteroaryl group can be applied except that the heteroarylene is a divalent group. In the present specification, the aforementioned description of the aryl group or cycloalkyl group can be applied except that the hydrocarbon ring is not a monovalent group but is formed by combining two substituent groups. In the present specification, the aforementioned description of the heteroaryl group can be applied, except that the heterocycle is not a monovalent group but is formed by combining two substituent groups.

Meanwhile, the present disclosure provides a compound represented by Chemical Formula 1. The compound represented by Chemical Formula 1 simultaneously includes a substituent of Chemical Formula 2 and a substituent of Chemical Formula 3. In other words, at least one of the substituents $HAr_1$ to $HAr_4$ is Chemical Formula 2, and at least one of the substituents $HAr_1$ to $HAr_4$ is Chemical Formula 3 in Chemical Formula 1. Thus, n1+n2+n3+n4 has a value of 2 or more, wherein when n1+n2+n3+n4 is 2, one of $HAr_1$ to $HAr_4$ is a substituent represented by Chemical Formula 2, and the other of $HAr_1$ to $HAr_4$ is a substituent represented by Chemical Formula 3.

As described above, the compound represented by Chemical Formula 1, which includes both the N-containing 6-membered heteroaryl group of Chemical Formula 2 and the cyano group of Chemical Formula 3, exhibits high electron mobility and can control electron transfer speed at the same time. Therefore, the organic light-emitting device using the compound exhibits excellent properties in terms of efficiency and/or lifespan compared to the organic light-emitting device using a compound that does not contain these substituents or contains only one of these substituents.

Specifically, the compound represented by Chemical Formula 1 is represented by the following Chemical Formulae 1-1 or 1-2 according to the definition of $R_a$ and $R_b$:

Chemical Formula 1-1

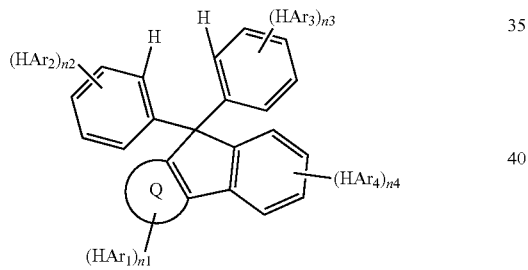

Chemical Formula 1-2

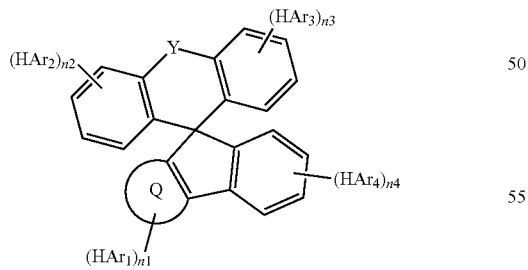

wherein, in Chemical Formulae 1-1 and 1-2,

Q, Y, $HAr_1$ to $HAr_4$, and n1 to n4 are as defined in Chemical Formula 1.

More specifically, the compound represented by Chemical Formula 1 may be represented by the following Chemical Formulae 1-1-1 to 1-1-3 and 1-2-1 to 1-2-3 according to the definition of $R_a$ and $R_b$ and the fused site of naphthalene:

Chemical Formula 1-1-1

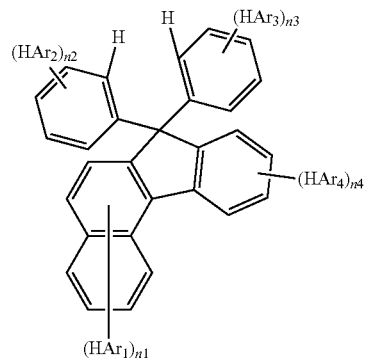

Chemical Formula 1-1-2

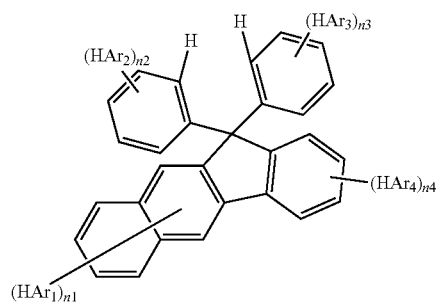

Chemical Formula 1-1-3

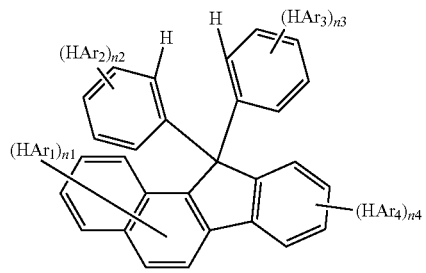

Chemical Formula 1-2-1

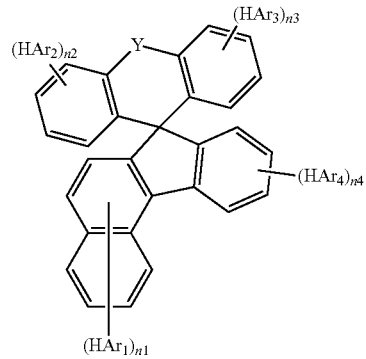

Chemical Formula 1-2-2

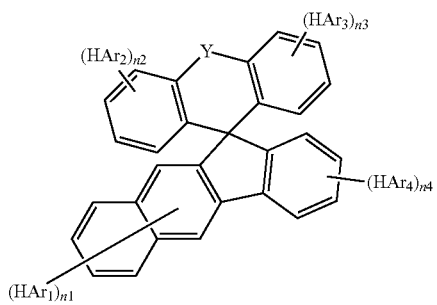

Chemical Formula 1-2-3

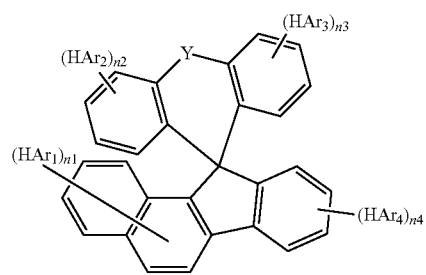

wherein, in Chemical Formulae 1-1-1 to 1-1-3 and 1-2-1 to 1-2-3,

Y is single bond, O, or S, and $HAr_1$ to $HAr_4$ and n1 to n4 are as defined in Chemical Formula 1.

Preferably, $L_1$ and $L_2$ may each independently be a single bond, or a $C_{6-20}$ arylene.

Specifically, $L_1$ and $L_2$ may each independently be single bond, phenylene, or biphenylene.

More specifically, $L_1$ may be a single bond, or any one selected from the group consisting of the following.

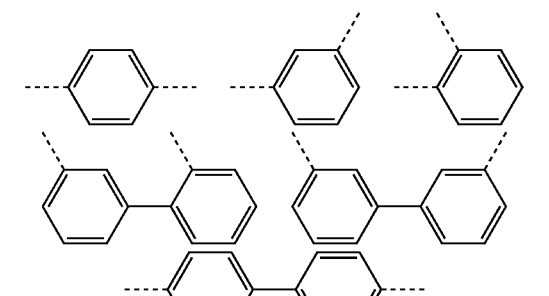

$L_2$ may be single bond, or any one selected from the group consisting of the following.

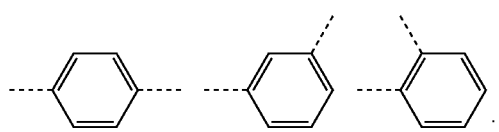

Preferably, $X_1$ to $X_3$ may each independently be N or CR, wherein R may be hydrogen. More preferably, $X_1$ to $X_3$ may be N.

Preferably, Ar and $Ar_2$ may each independently be a $C_{6-20}$ aryl which is unsubstituted, or substituted with pyridinyl.

Specifically, $Ar_1$ and $Ar_2$ may each independently be phenyl or pyridinylphenyl.

For example, $Ar_1$ and $Ar_2$ may be phenyl, or $Ar_1$ may be phenyl and $Ar_2$ may be pyridinylphenyl.

Preferably, n1 to n4 are each 0 or 1, and n1+n2+n3+n4 is 2.

For example, the compound may be represented by Chemical Formula 1-1.

In this regard, Q is naphthalene, $HAr_1$ and $HAr_2$ are each independently Chemical Formula 2 or 3, and at least one of $HAr_1$ and $HAr_2$ is Chemical Formula 2, $HAr_3$ and $HAr_4$ are each independently the Chemical Formula 3, n1 to n4 are each 0 or 1, and n1+n2+n3+n4 is 2.

Alternatively, the compound may be represented by the following Chemical Formula 1-2A:

Chemical Formula 1-2A

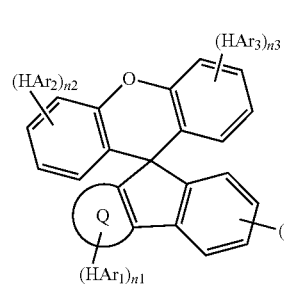

wherein, in Chemical Formula 1-2A,

Q is naphthalene, $HAr_1$ to $HAr_3$ are each independently Chemical Formula 2 or 3, and at least one of $HAr_1$ to $HAr_3$ is Chemical Formula 2, $HAr_4$ is Chemical Formula 3, n1 to n4 are each 0 or 1, and n1+n2+n3+n4 is 2.

Alternatively, the compound may be represented by the following Chemical Formula 1-2B:

Chemical Formula 1-2B

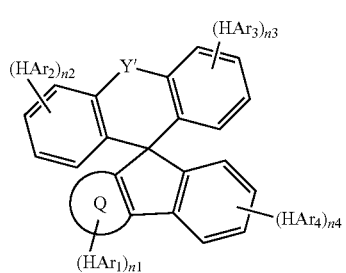

wherein, in Chemical Formula 1-2B,

Q is naphthalene,

Y' is single bond, or S, one of $HAr_1$ to $HAr_4$ is the following Chemical Formula 2, one of the others is the following Chemical Formula 3, the rest are each independently Chemical Formula 2 or 3, n1 to n4 are each 0 or 1, and n1+n2+n3+n4 is 2.

More preferably, when n1+n2+n3+n4 is 2, n1 and n3 are 1, and n2 and n4 are 0;

n1 and n4 are 1, and n2 and n3 are 0; or n2 and n3 are 1, and n1 and n4 are 0.

For example, the compound represented by Chemical Formula 1 may be represented by any one of the following Chemical Formulae 4-1 to 4-7:

4-1

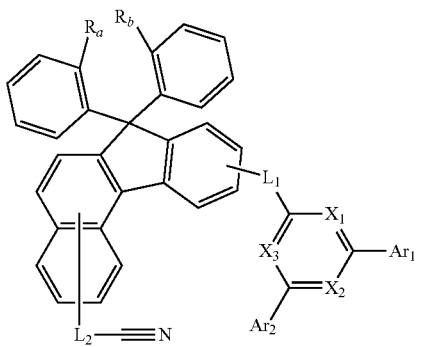

4-2

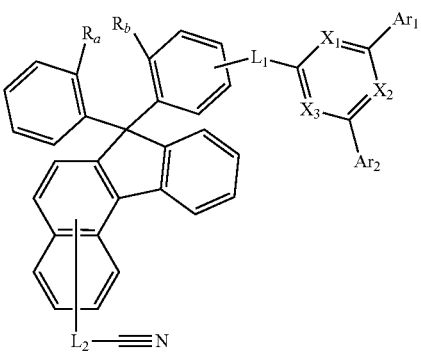

4-3

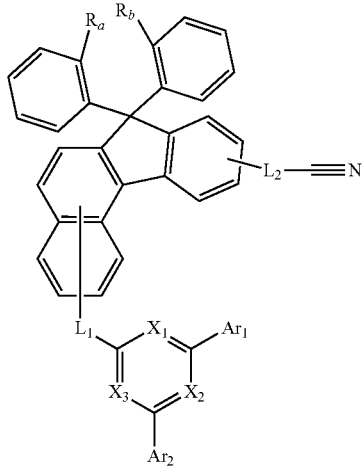

4-4

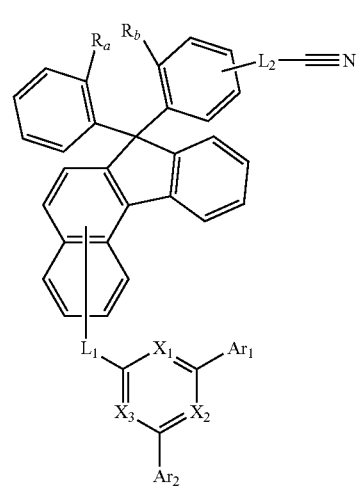

4-5

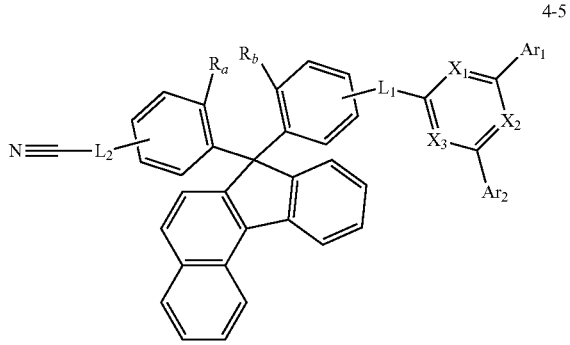

4-6

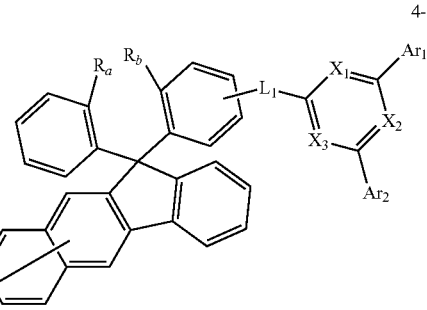

4-7

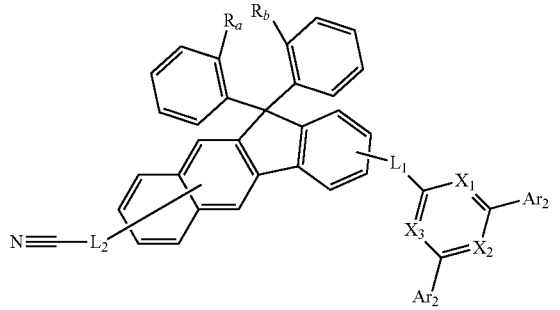

wherein, in Chemical Formulae 4-1 to 4-7, $R_a$, $R_b$, $L_1$, $L_2$, $X_1$ to $X_3$, $Ar_1$, and $Ar_2$ are as defined in Chemical Formula 1.

Preferably, in Chemical Formula 4-1 and 4-7, $R_a$ and $R_b$ are bonded to each other to form a single bond, or S, in Chemical Formula 4-2, 4-5, and 4-6, $R_a$ and $R_b$ are bonded to each other to form single bond, O or S, in Chemical Formula 4-3 and 4-4, $R_a$ and $R_b$ are each hydrogen, or are bonded to each other to form single bond, O or S.

Further preferably, n1 to n4 may each be 0, 1, or 2, and n1+n2+n3+n4 may be 3.

For example, in Chemical Formula 1, one of $HAr_1$ to $HAr_4$ may be Chemical Formula 2, and two of the others may be Chemical Formula 3.

Further preferably, when n1+n2+n3+n4 is 3, n1, n2, and n4 are 1, and n3 is 0;

n1, n3, and n4 are 1, and n2 is 0;

n1 is 2, n3 is 1, and n2 and n4 are 0;

n3 is 2, n1 is 1, and n2 and n4 are 0; or n4 is 2, n1 is 1, and n2 and n3 are 0.

More specifically, the compound represented by Chemical Formula 1 may be represented by any one of the following Chemical Formulae 5-1 to 5-7:

5-1

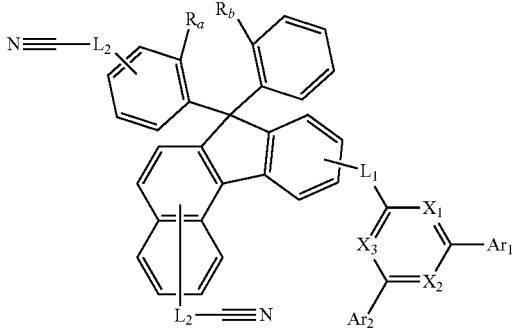

5-2

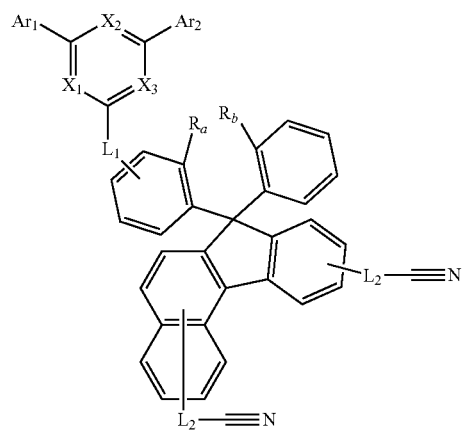

5-3

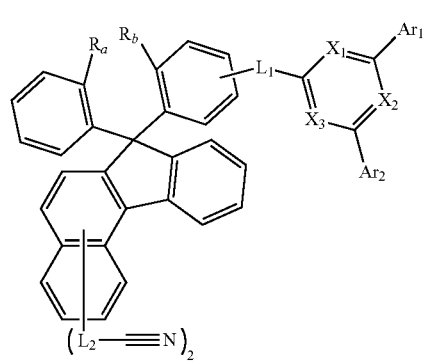

5-4

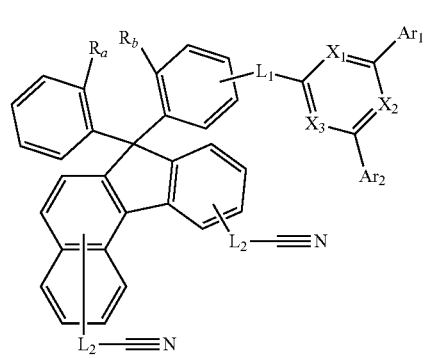

5-5

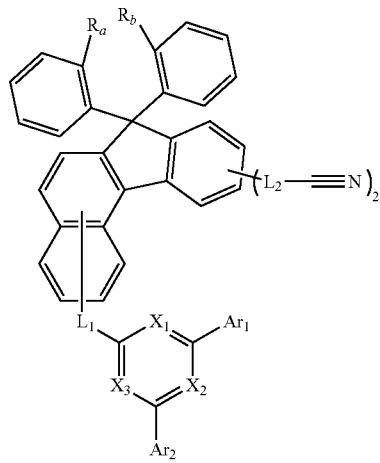

5-6
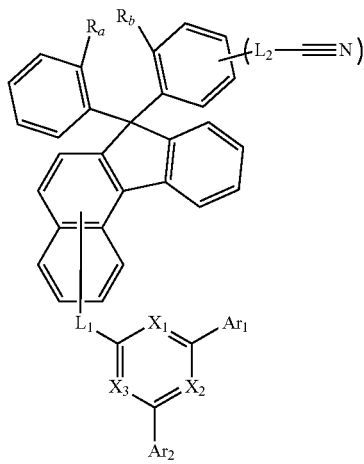
5-7
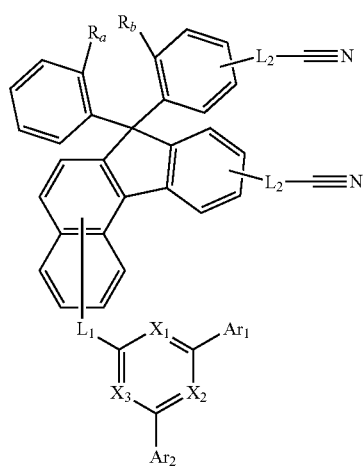
wherein, in Chemical Formulae 5-1 to 5-7,
$R_a$, $R_b$, $L_1$, $L_2$, $X_1$ to $X_3$, $Ar_1$, and $Ar_2$ are as defined in Chemical Formula 1.
For example, the above-mentioned compound may be any one selected from the group consisting of the following compounds.
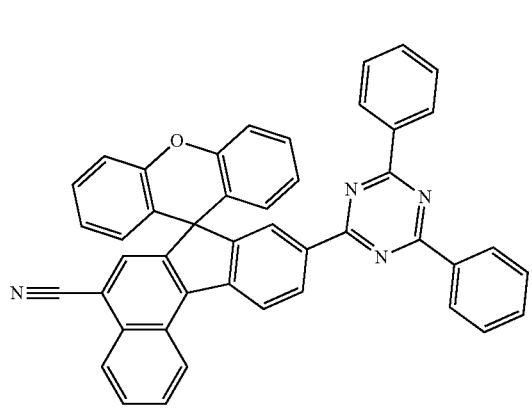
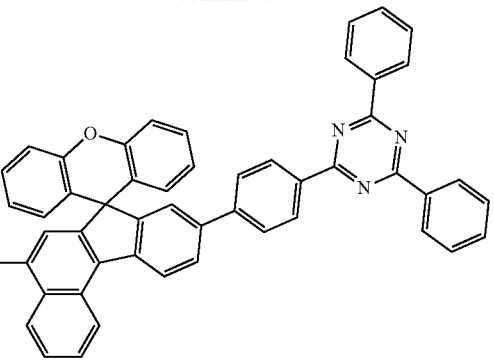
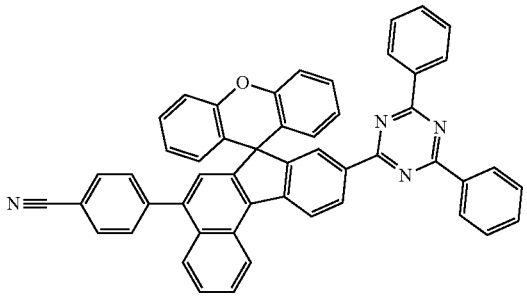
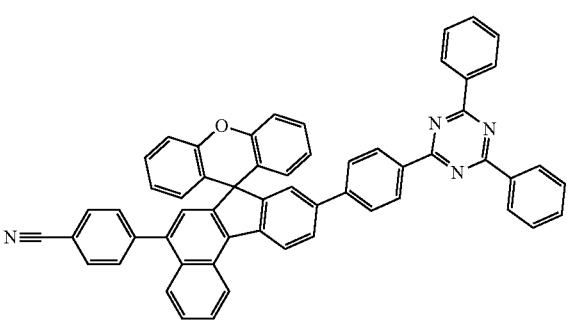
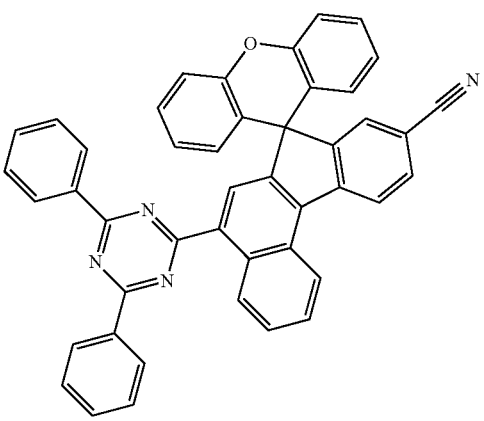

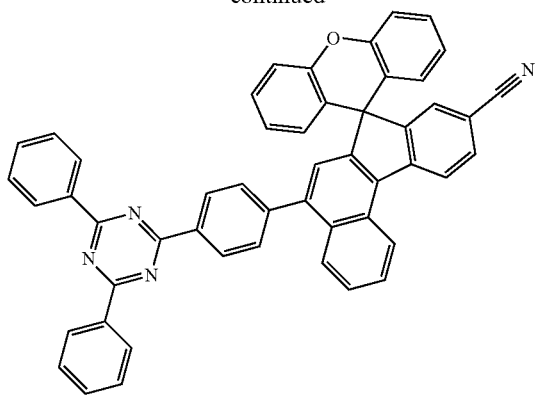
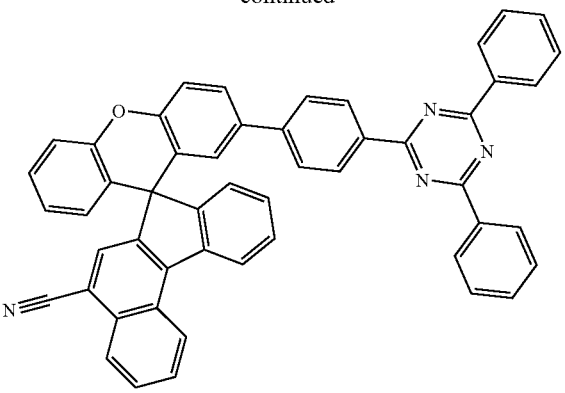
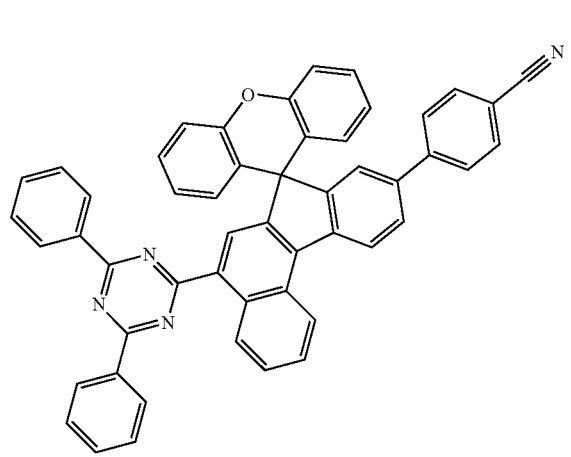
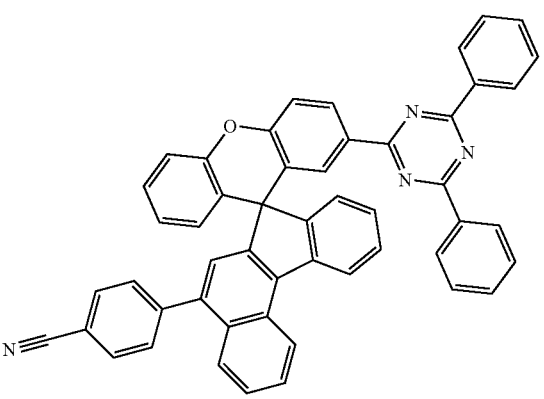
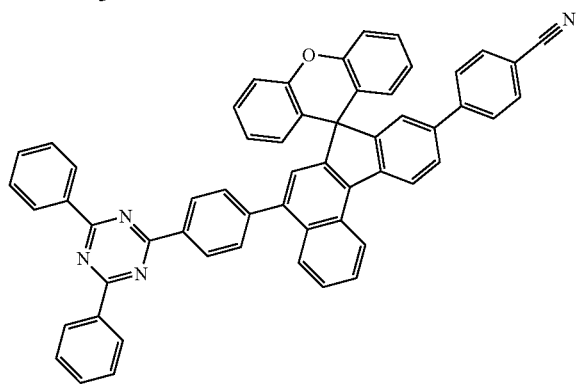
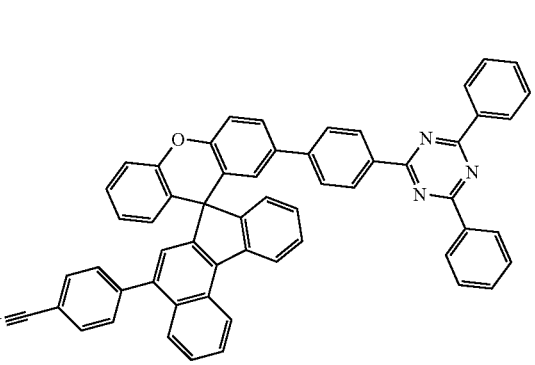
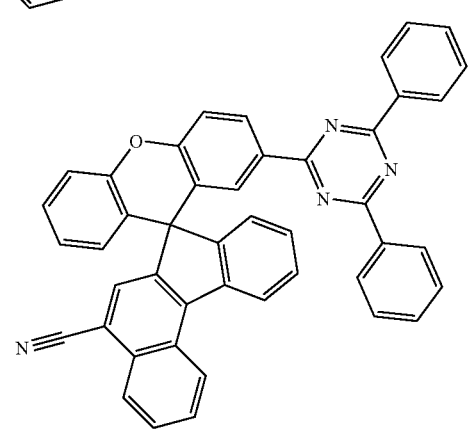
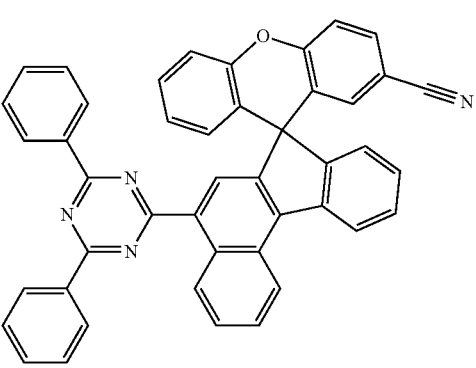

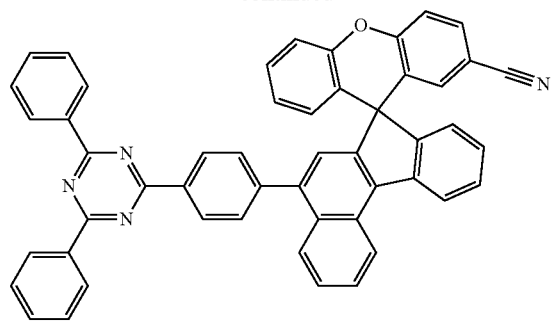
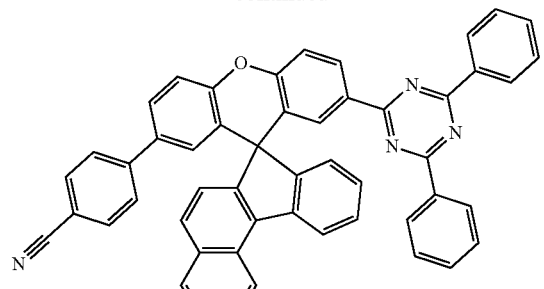
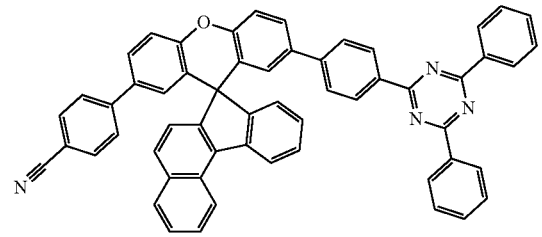
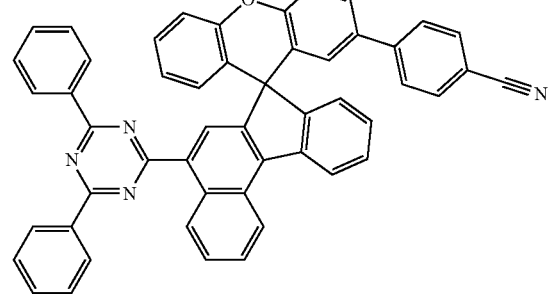
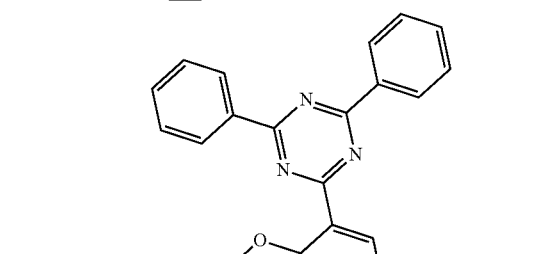
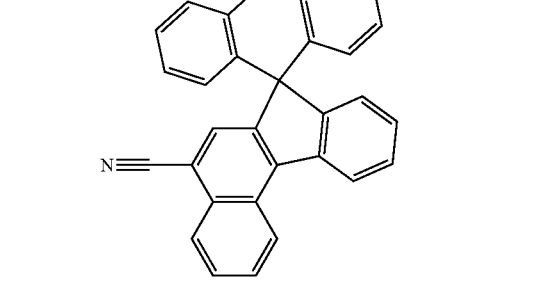
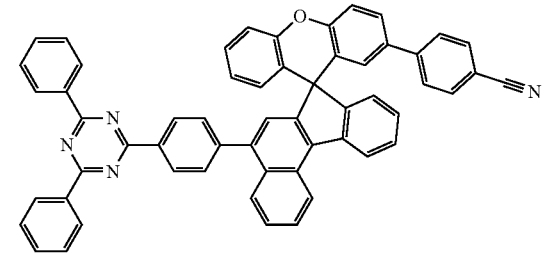
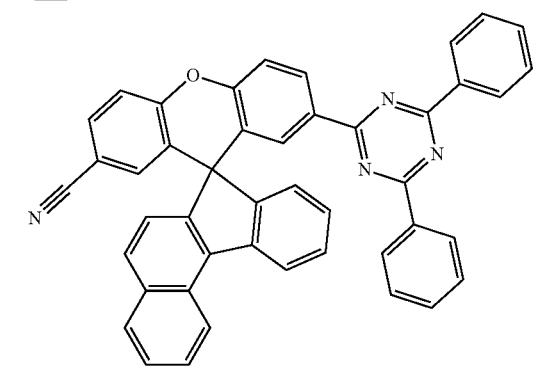
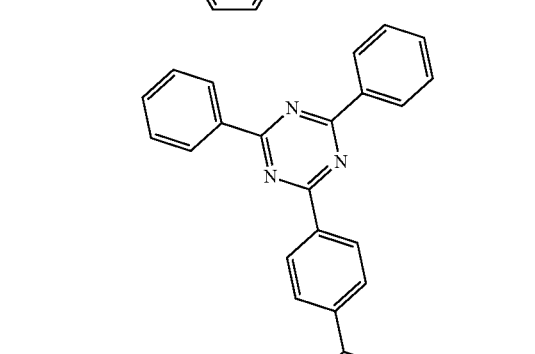
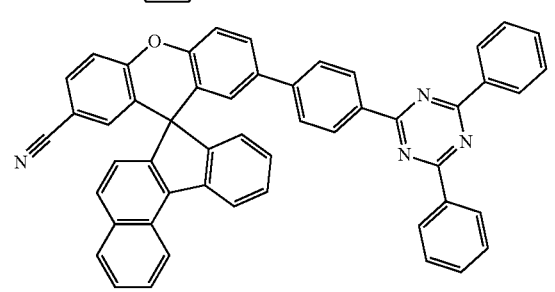
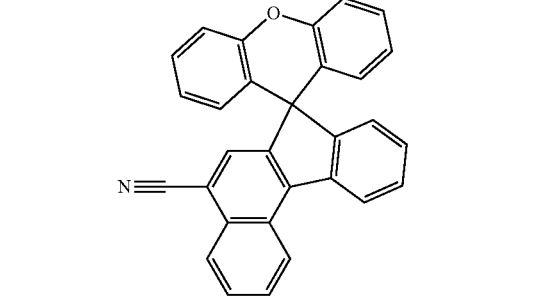

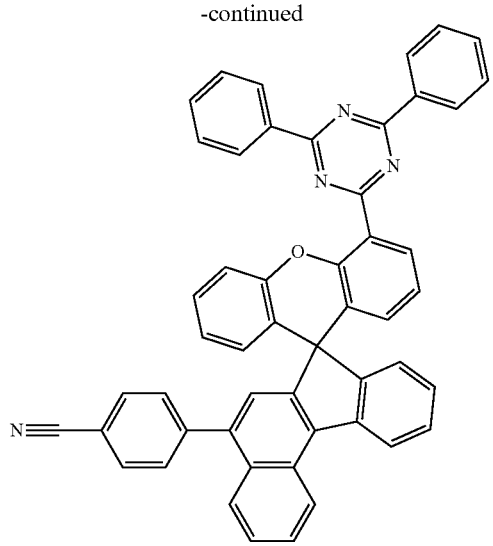
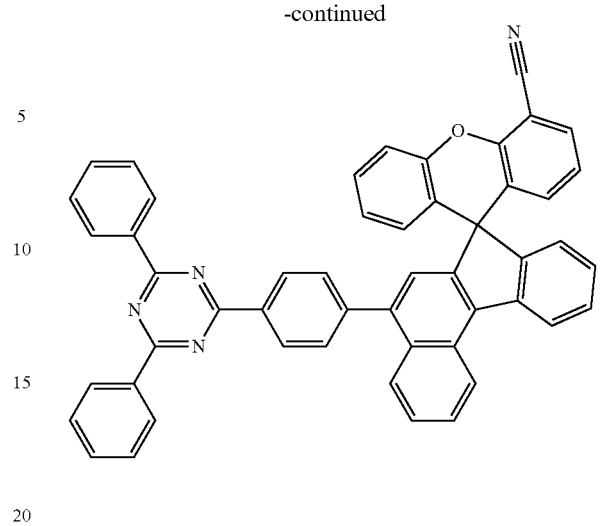
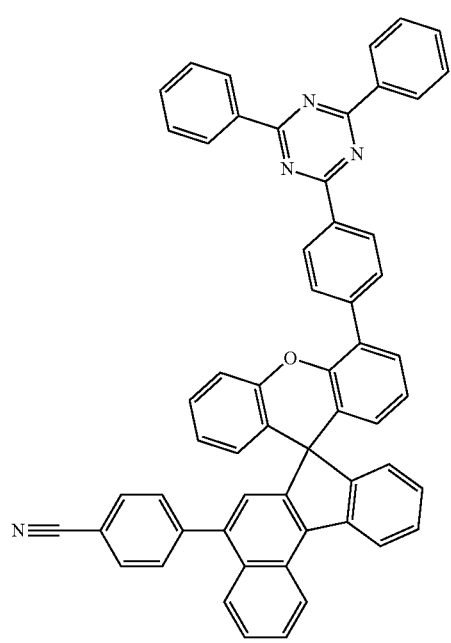
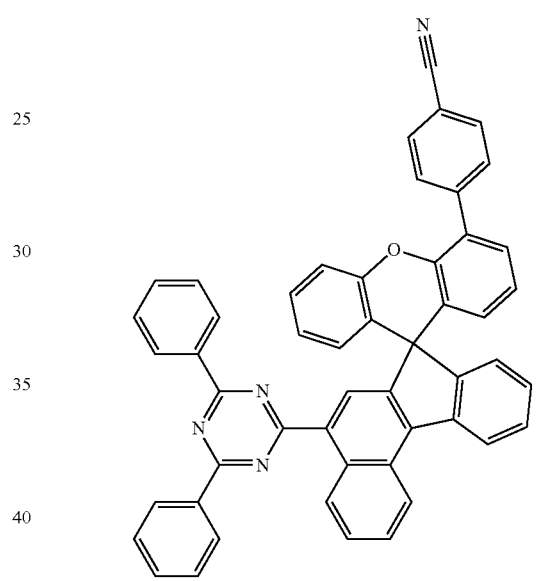
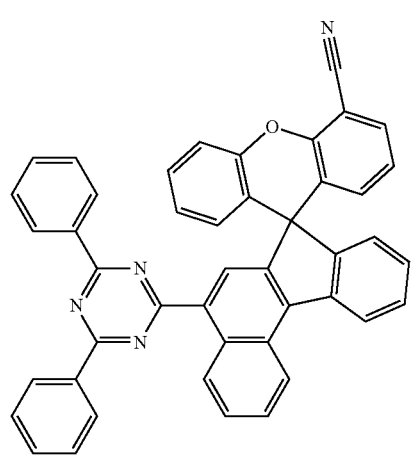
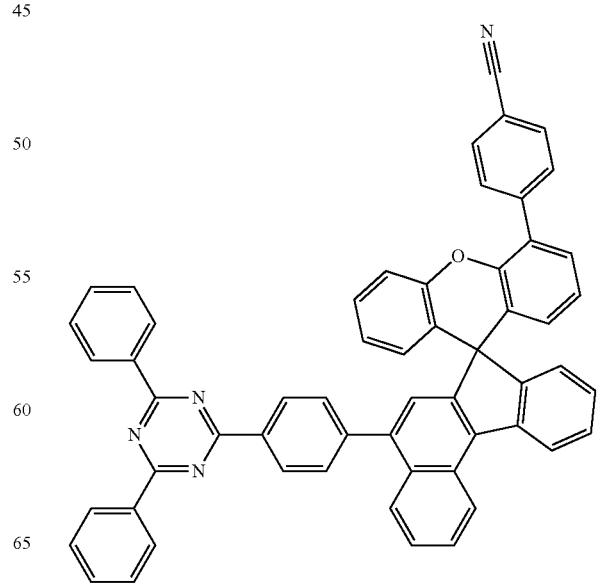

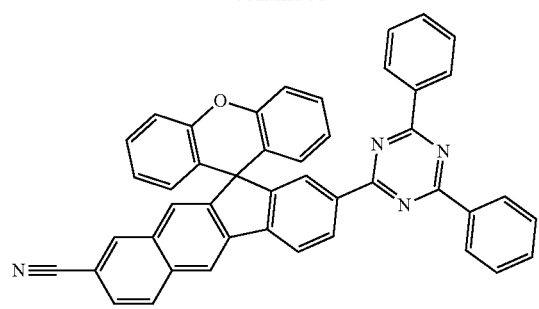
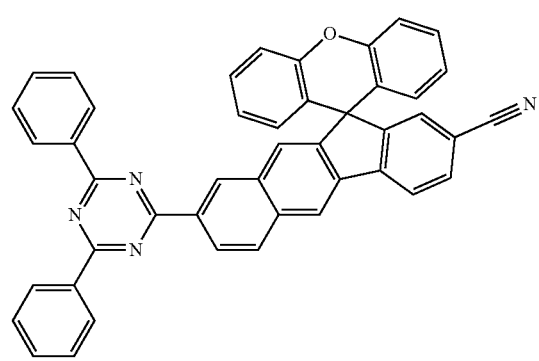
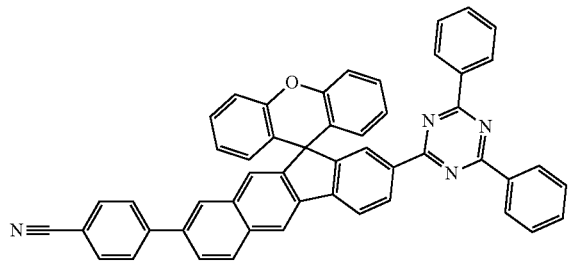
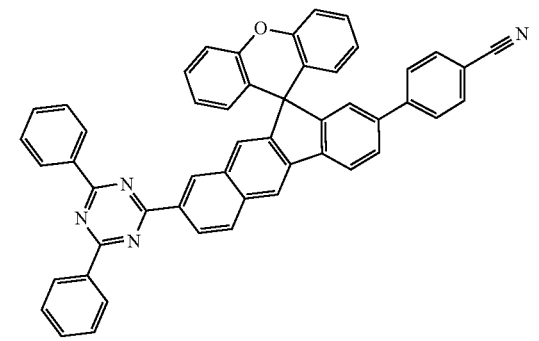
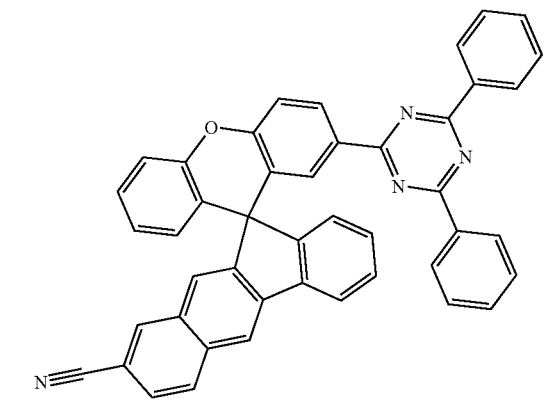
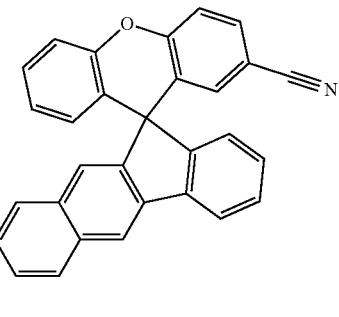
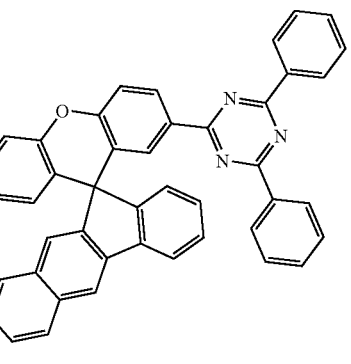
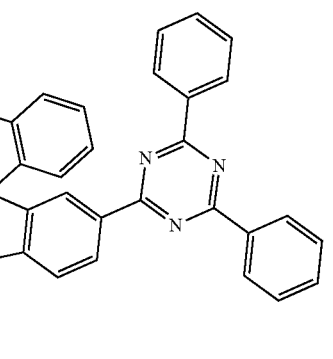
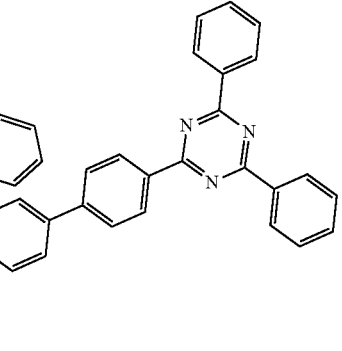

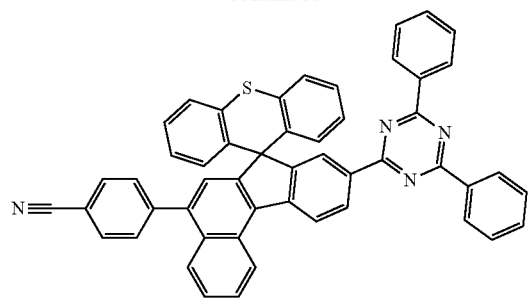
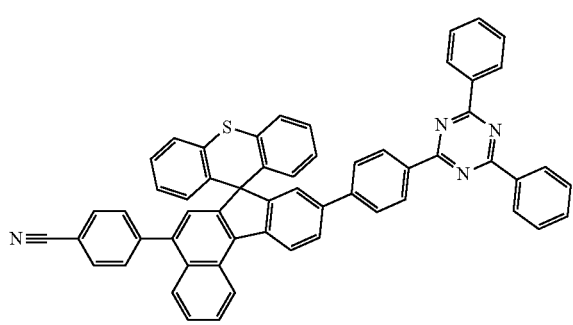
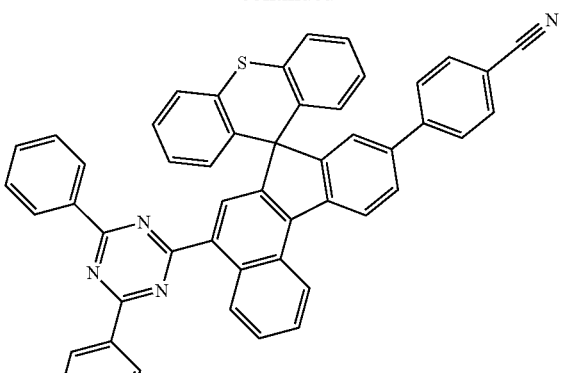
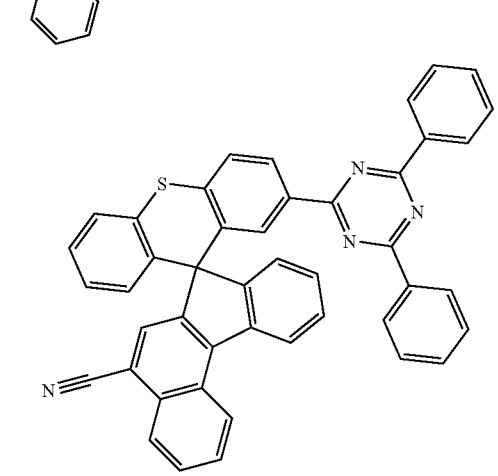
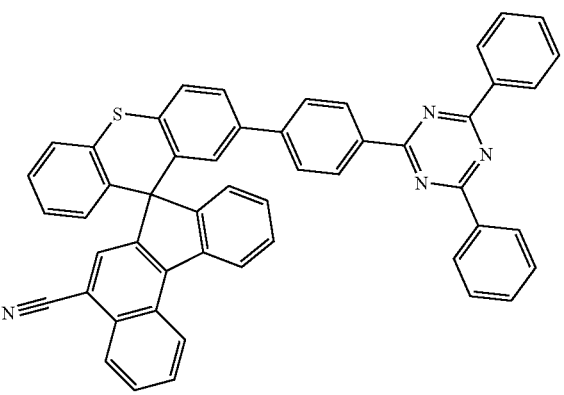

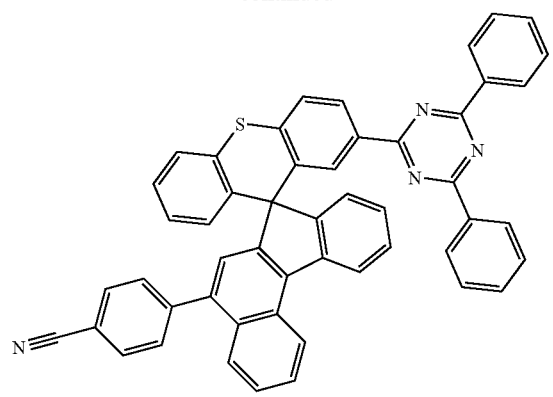
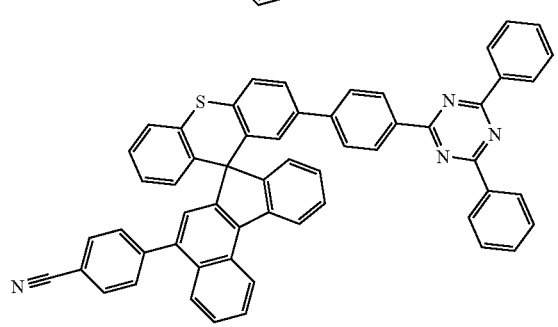
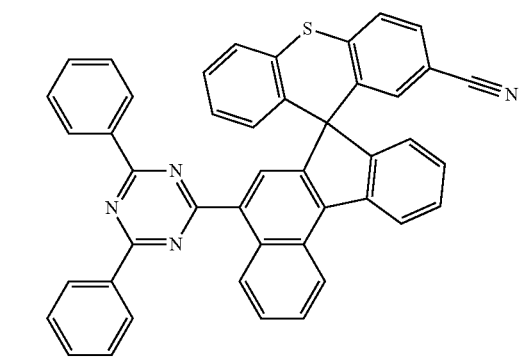
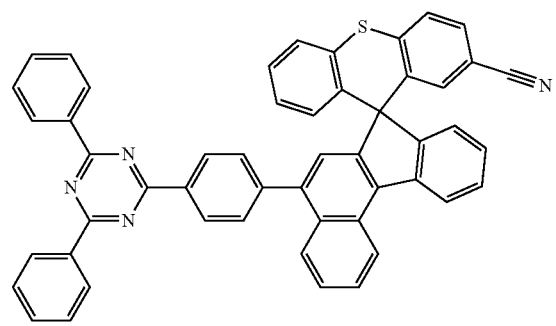
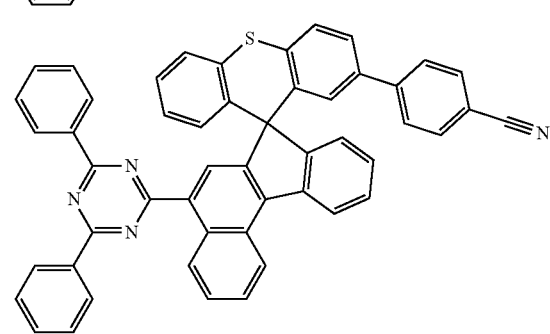
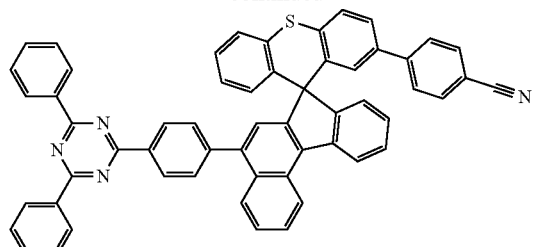
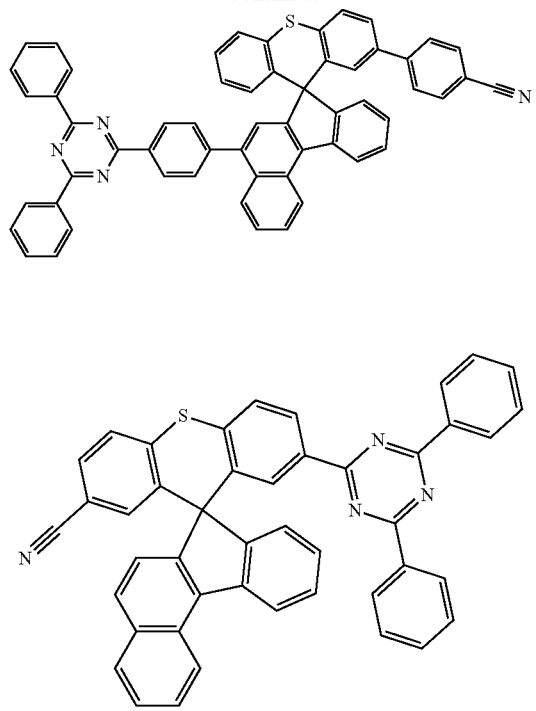
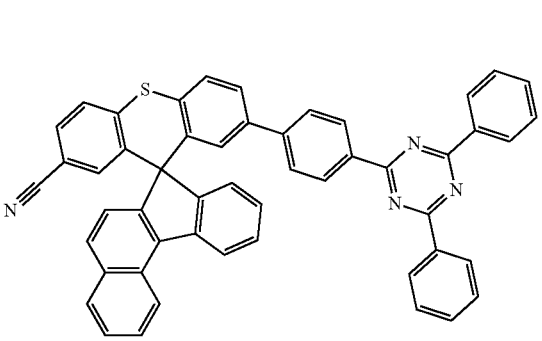
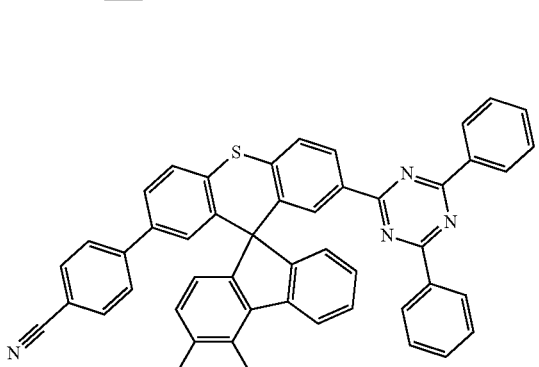
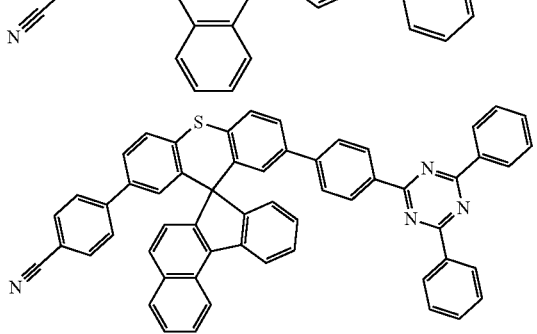

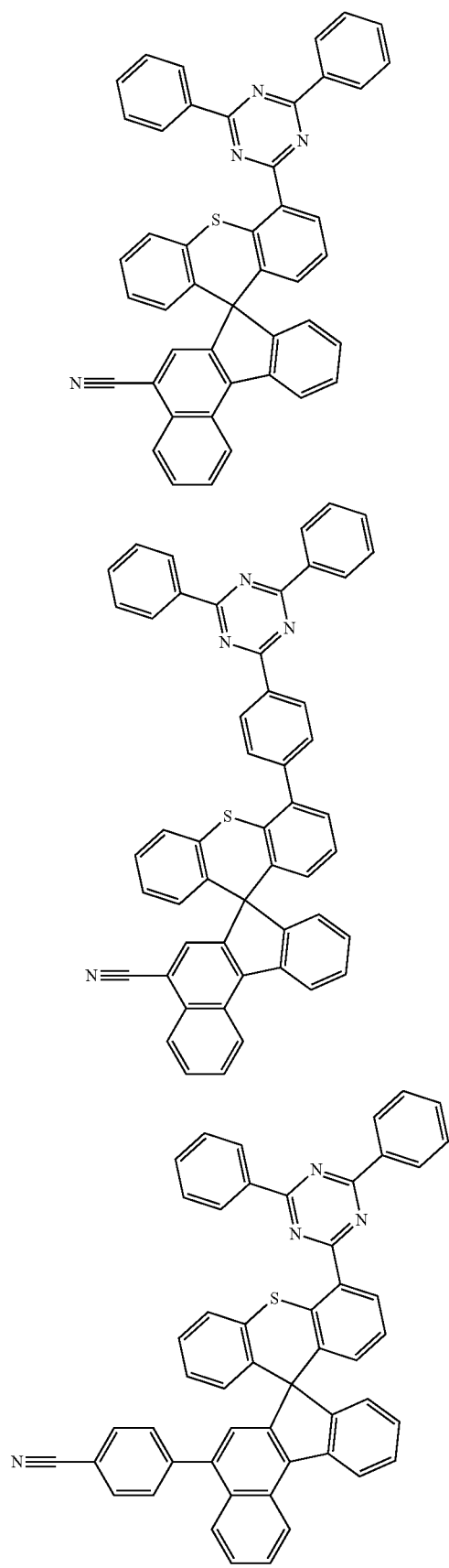
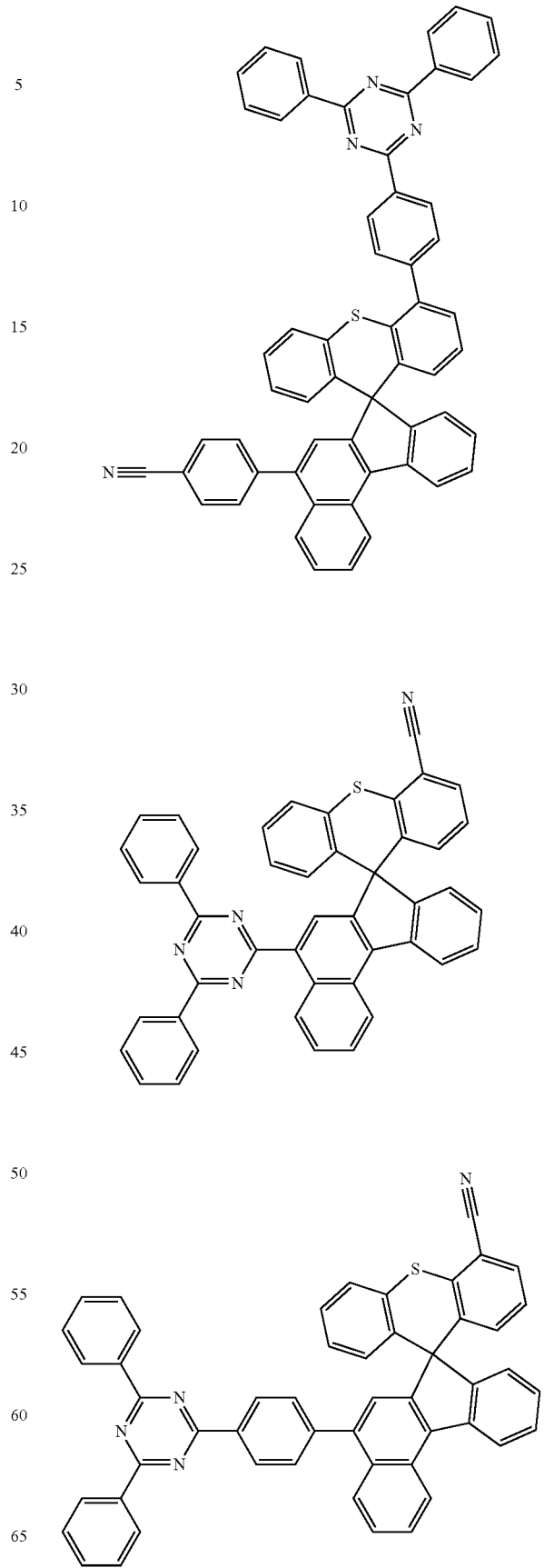

31
-continued
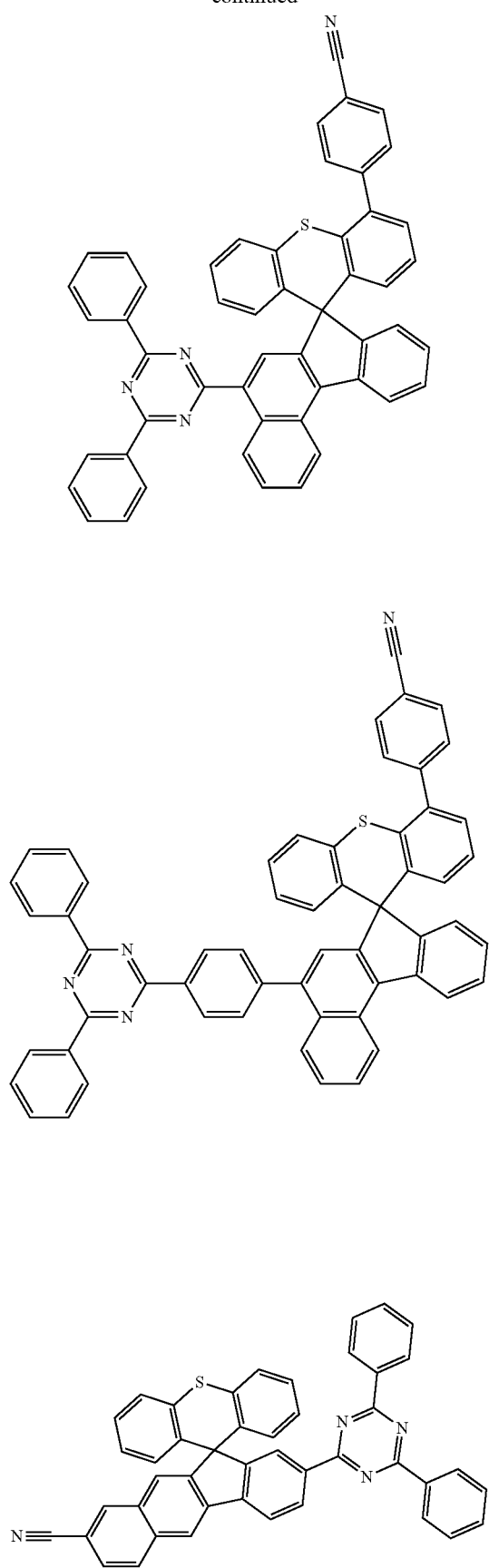
32
-continued
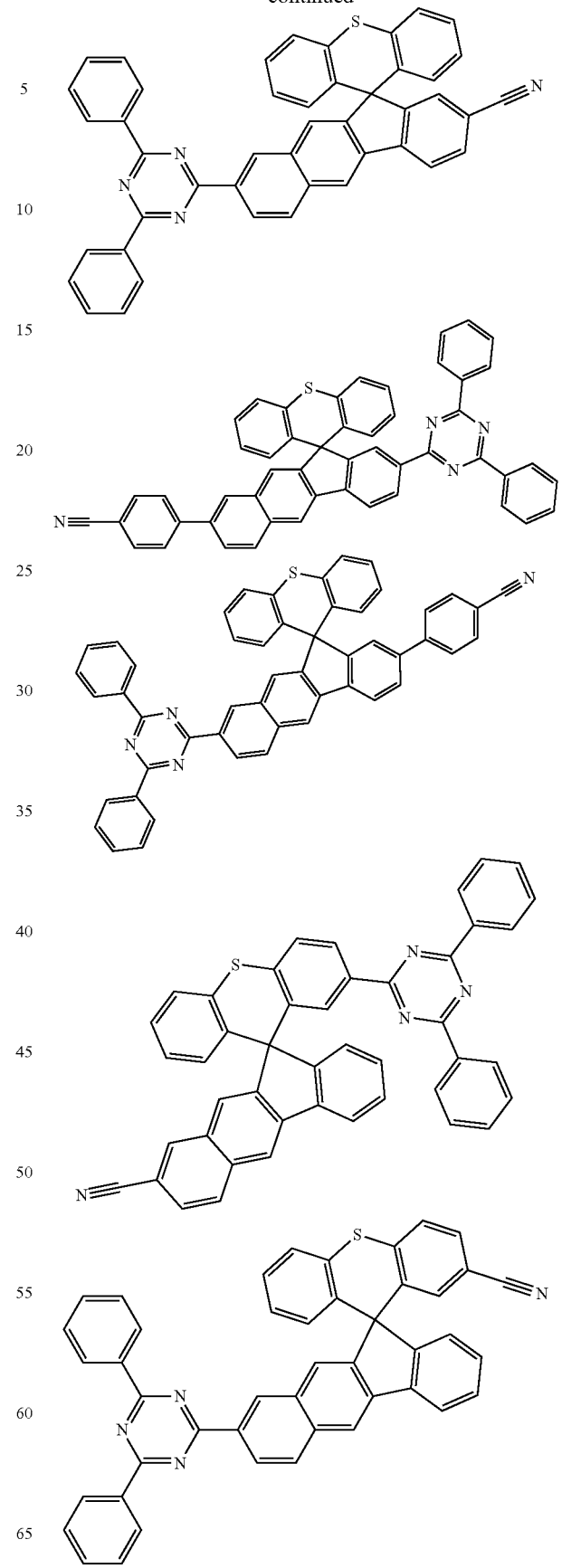

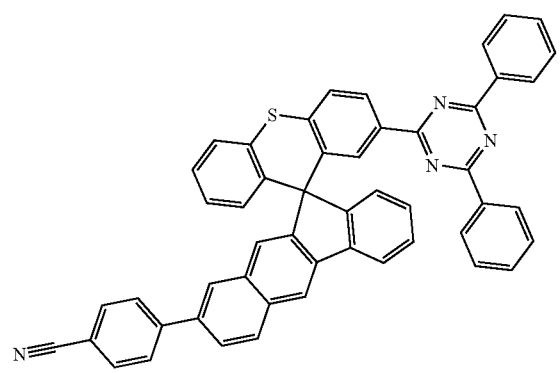
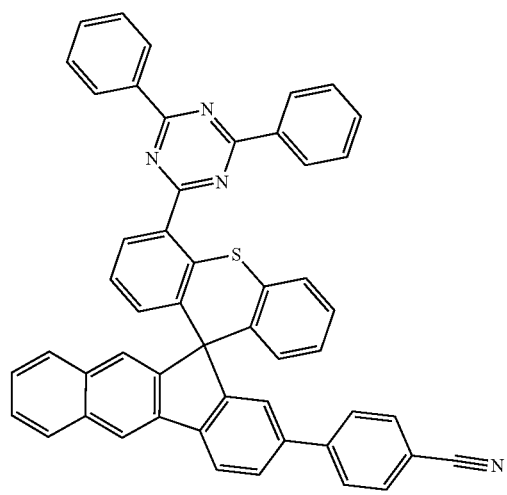
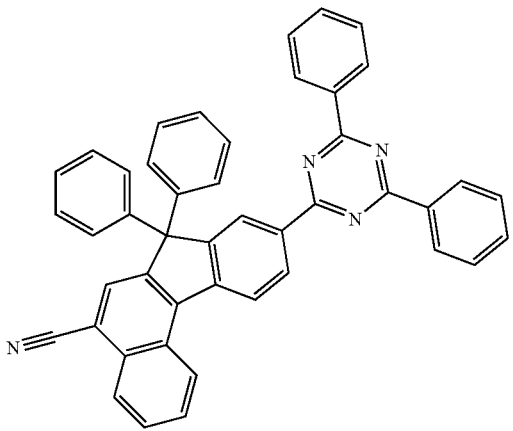
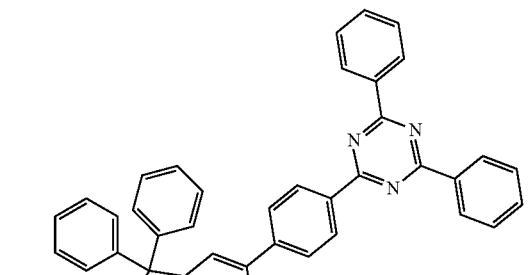

-continued
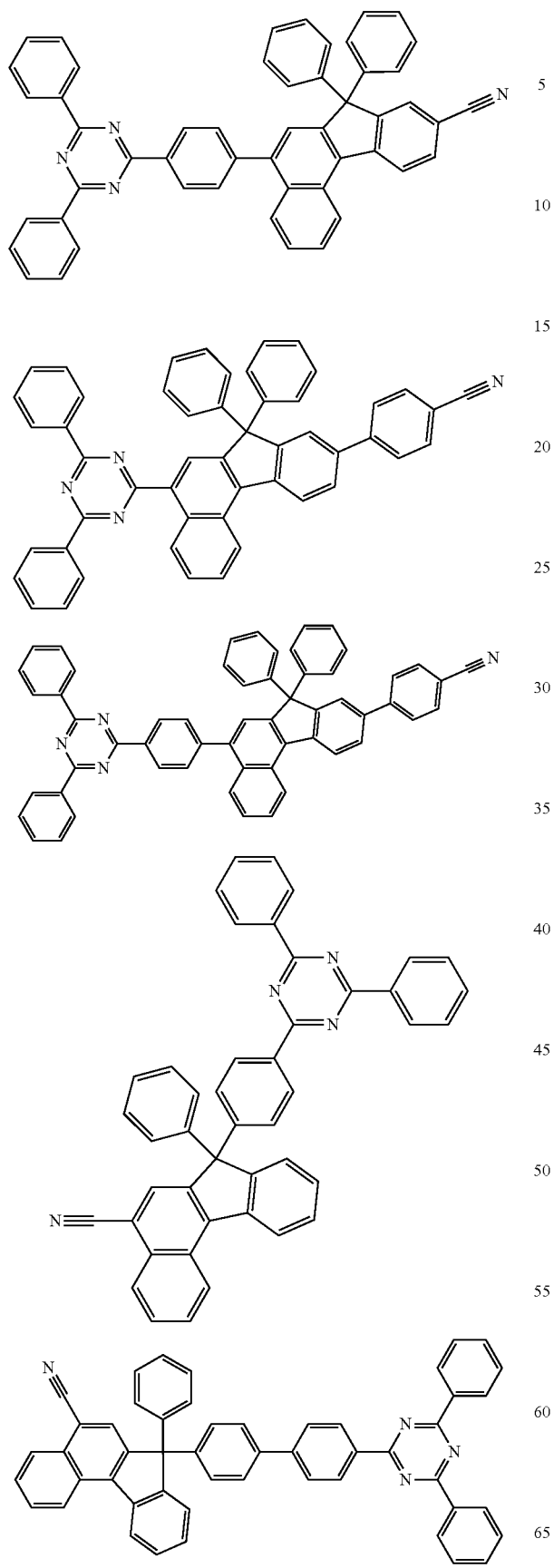
-continued
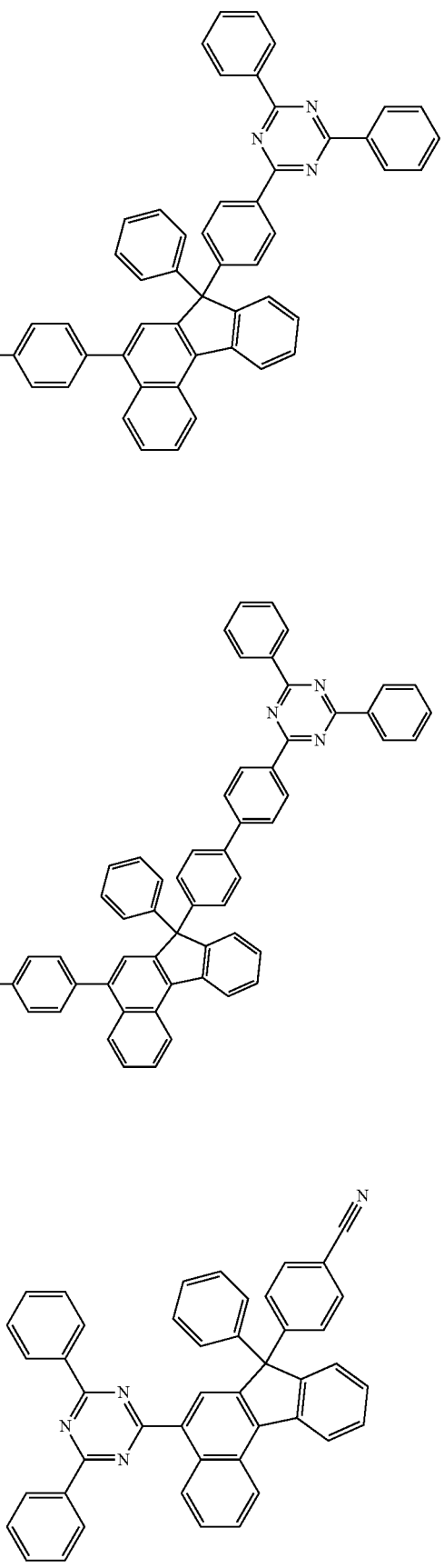

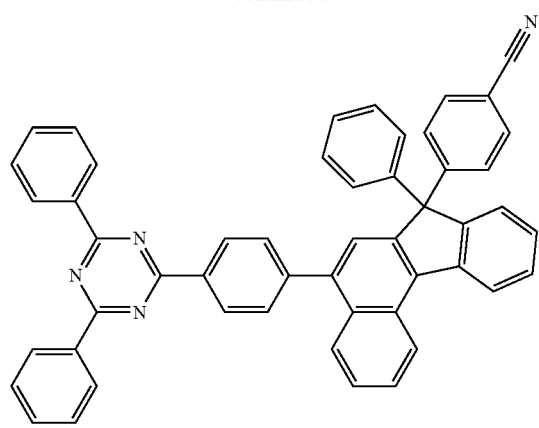
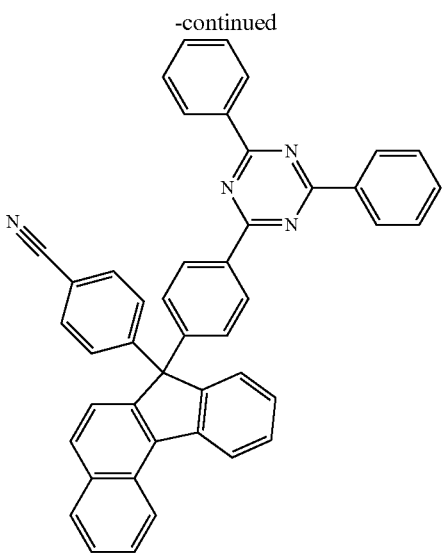
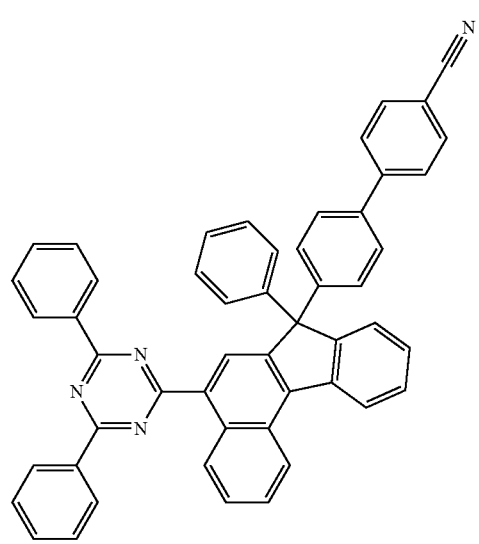
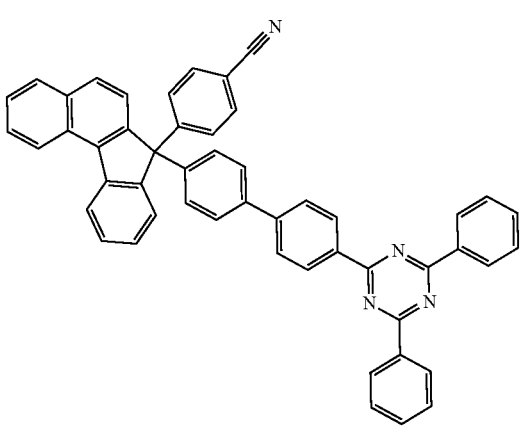
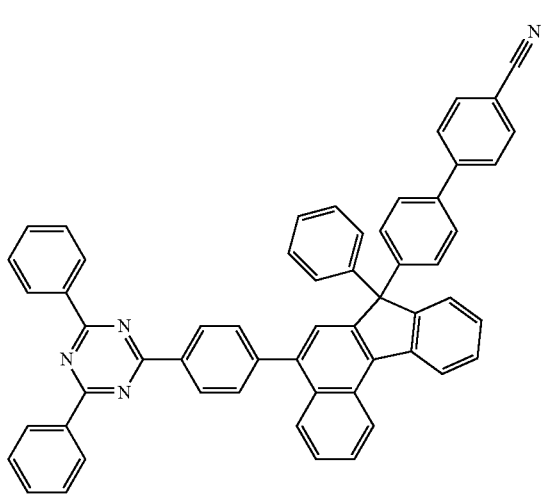
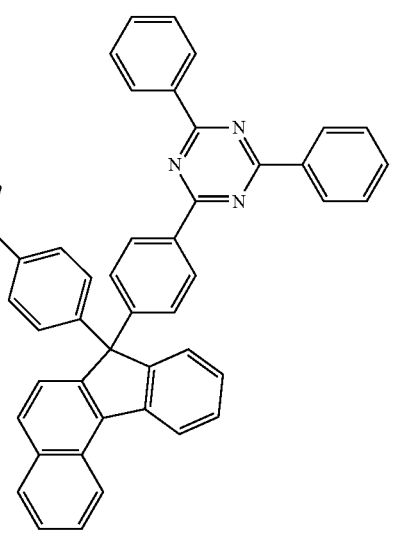

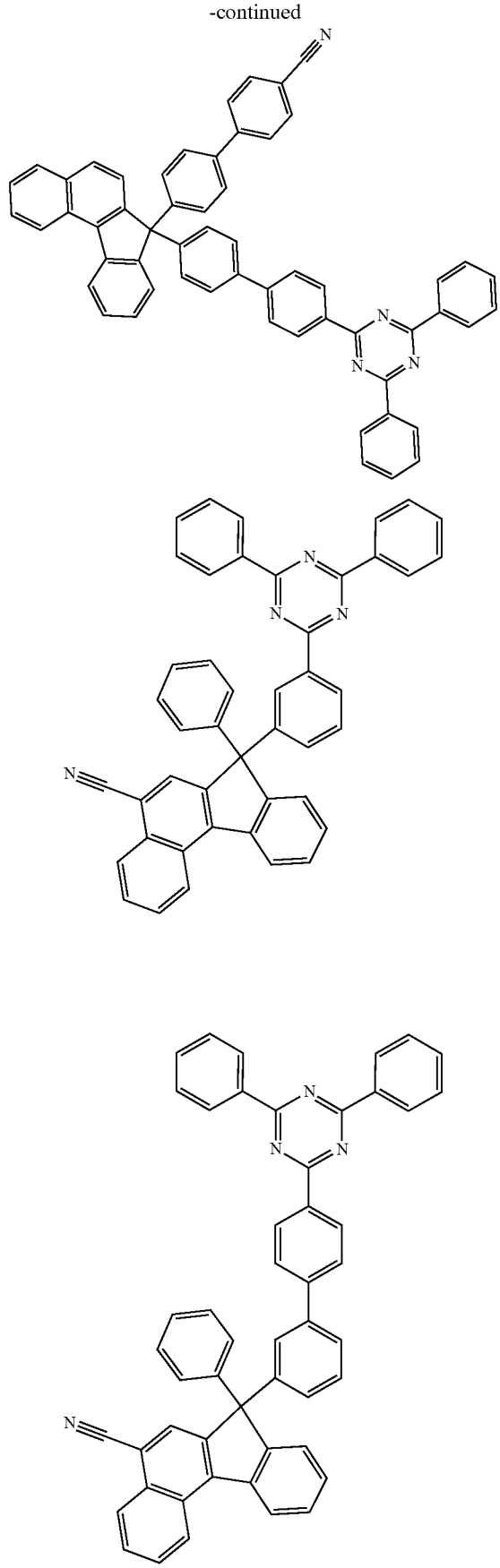
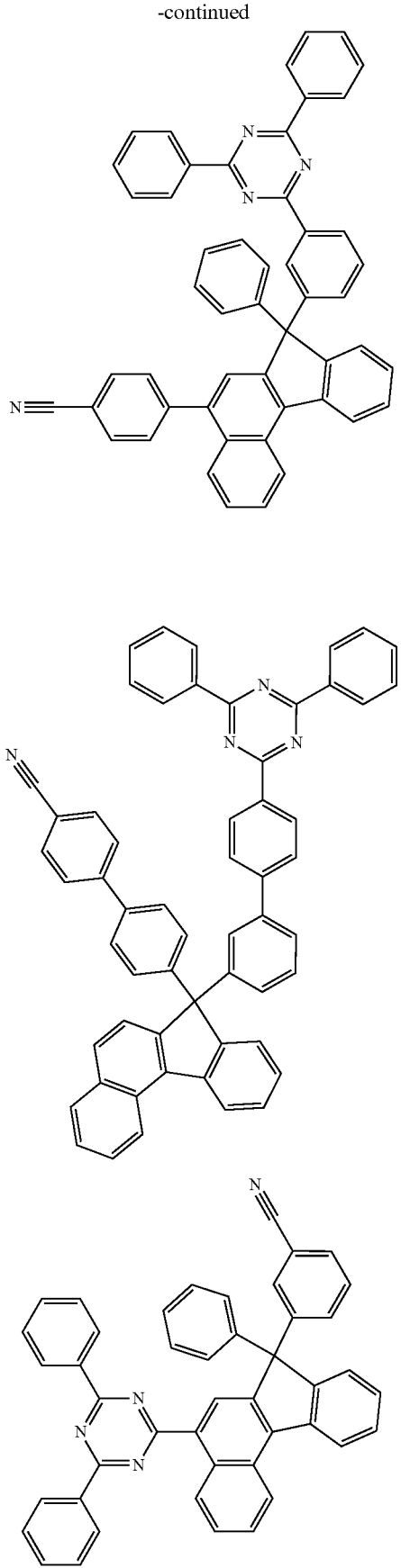

41
-continued
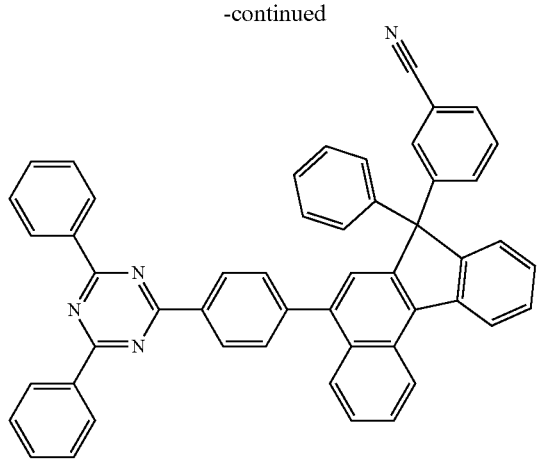
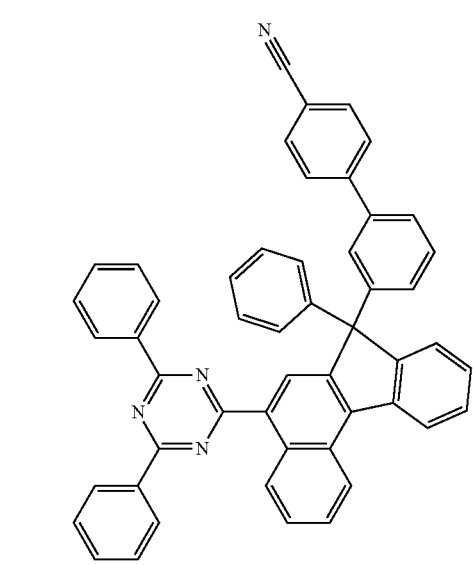
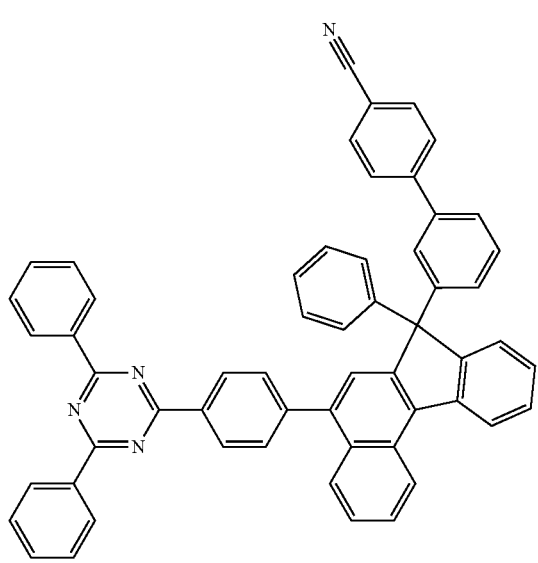
42
-continued
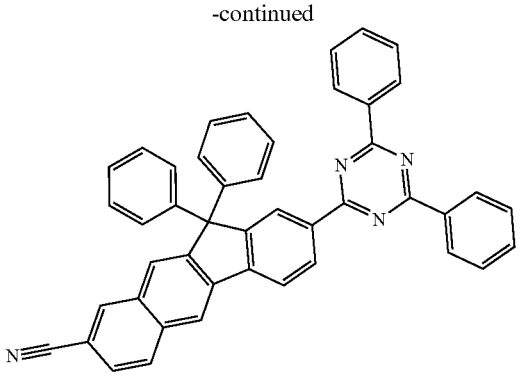
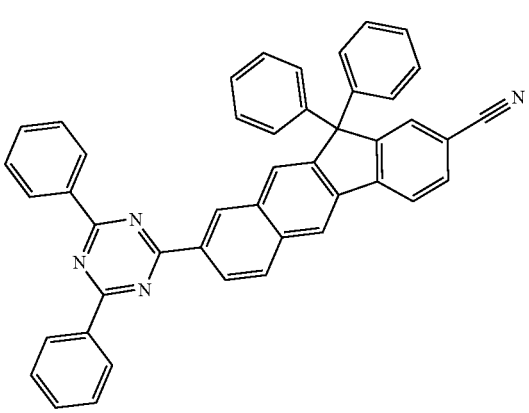
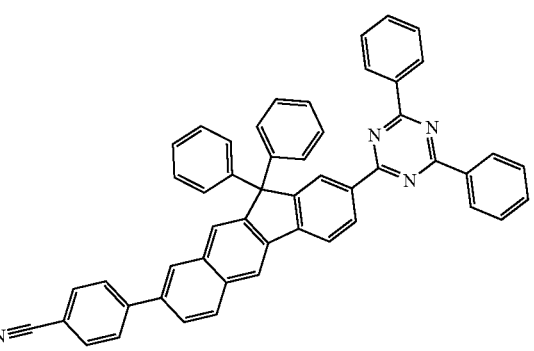
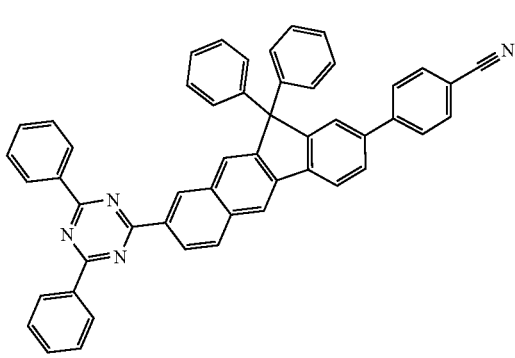

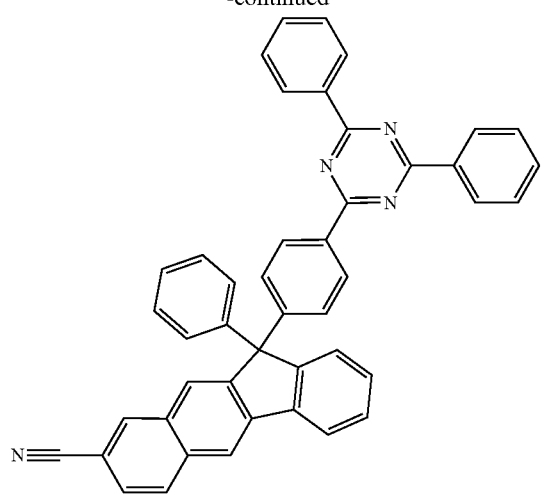
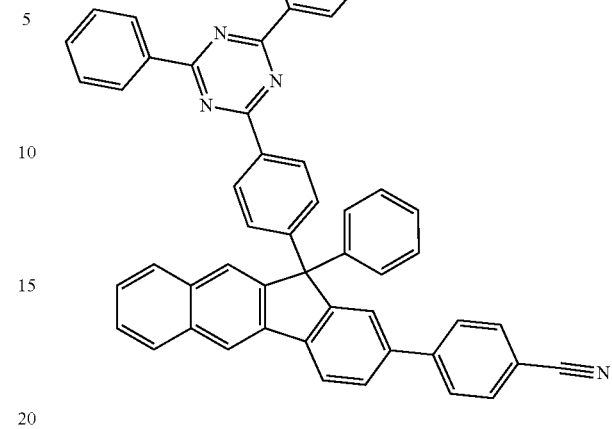
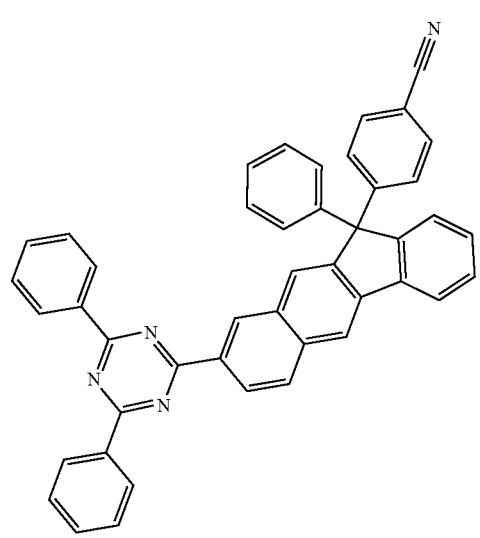
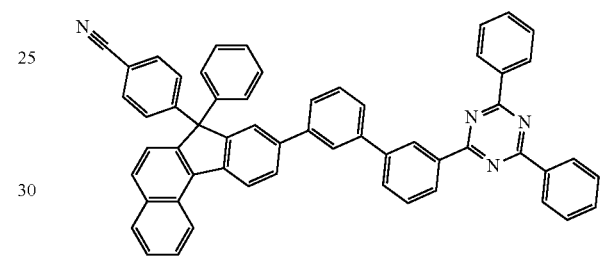
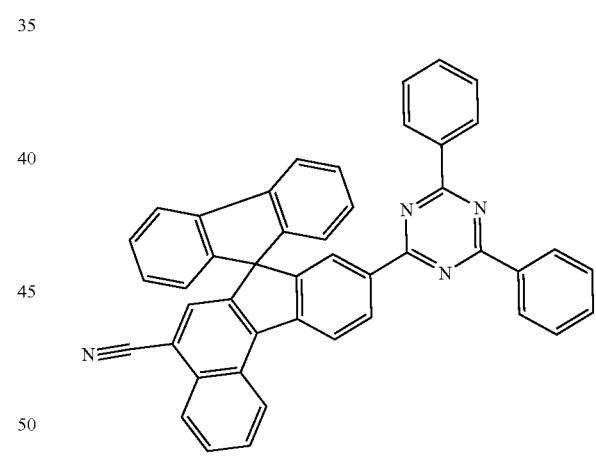
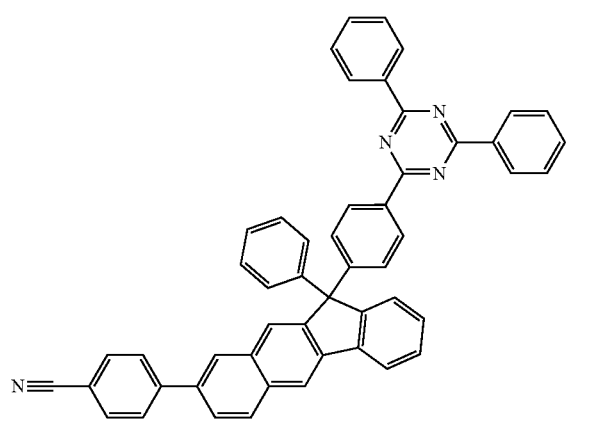
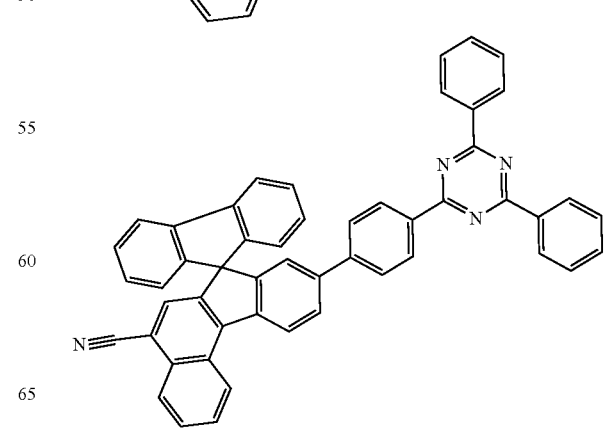

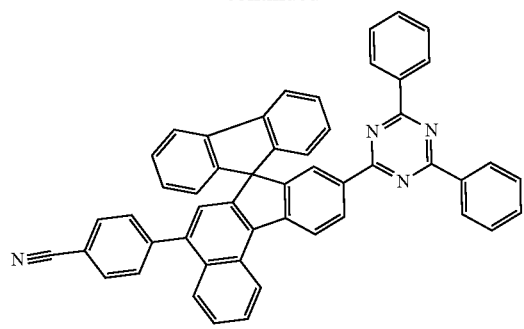
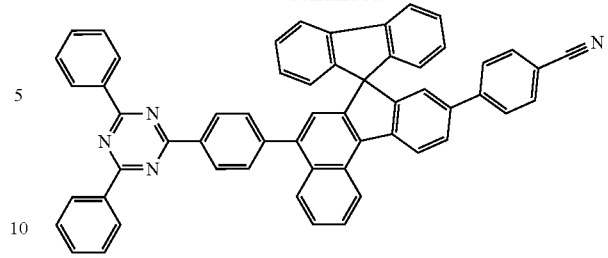
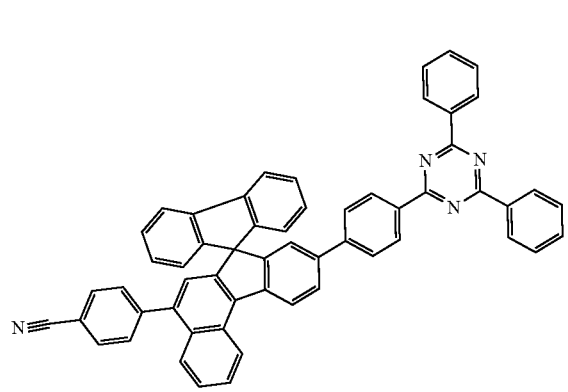
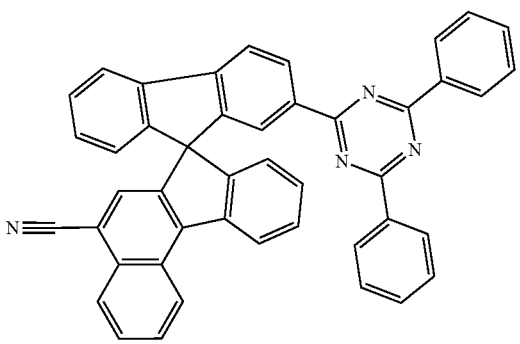
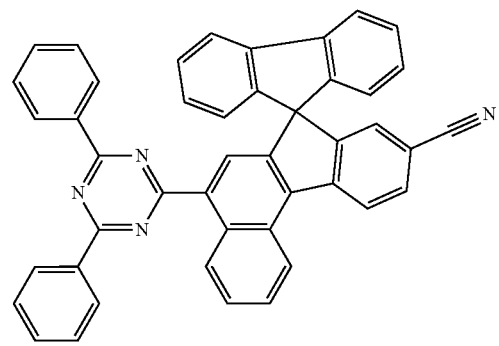
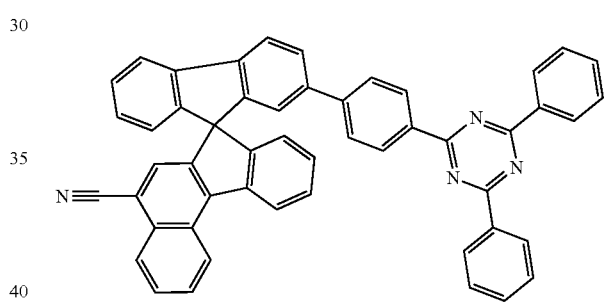
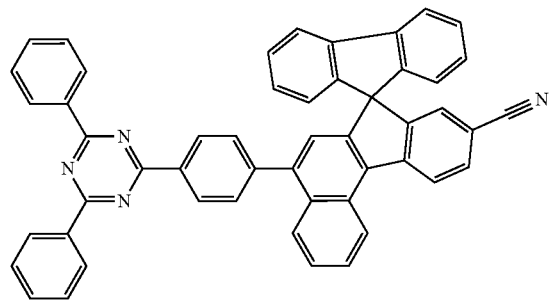
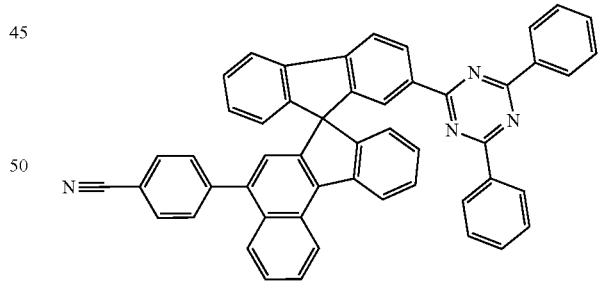
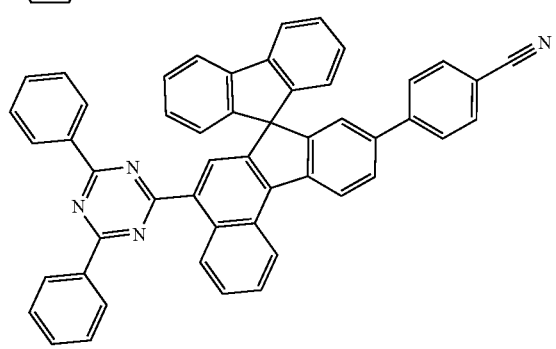
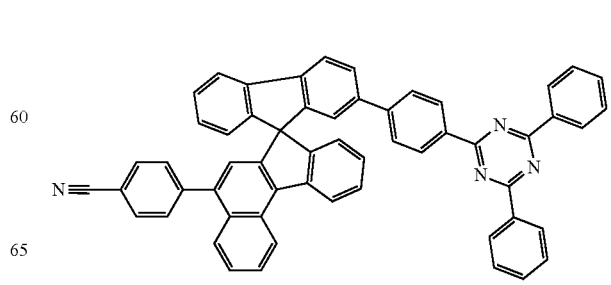

47
-continued
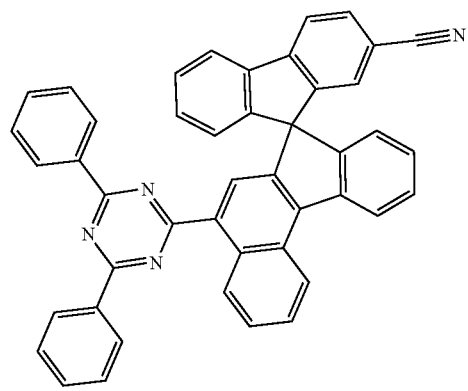
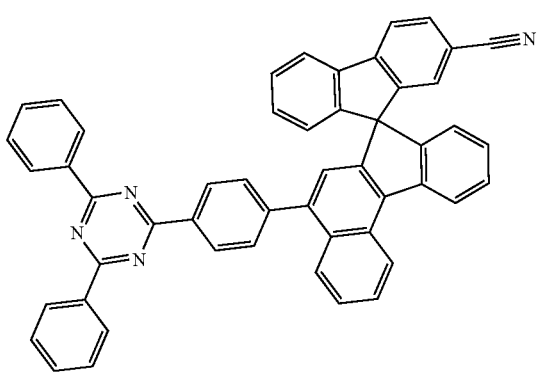
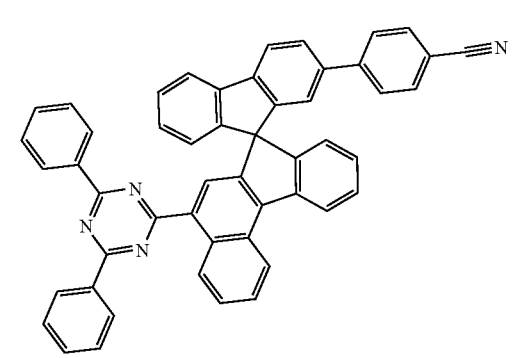
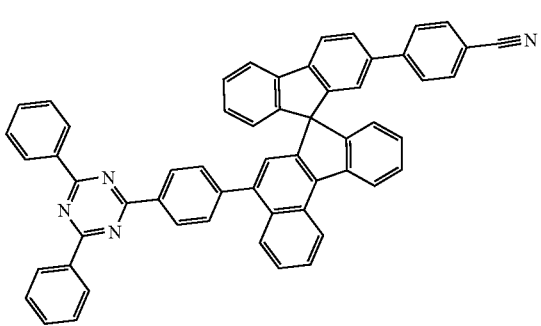
48
-continued
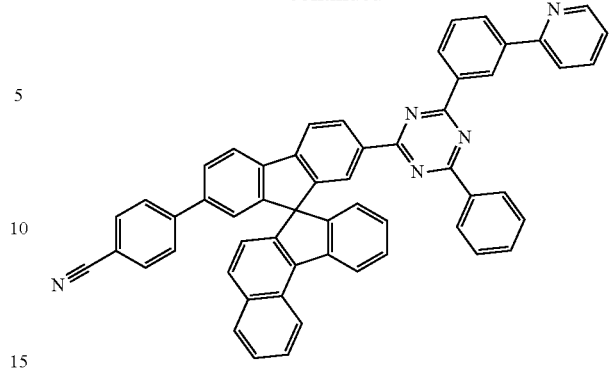
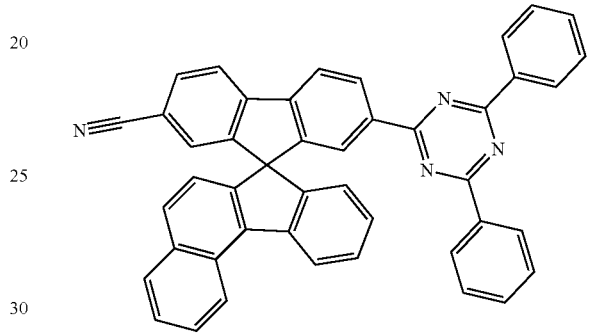
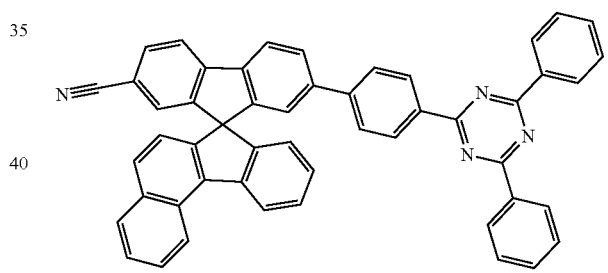
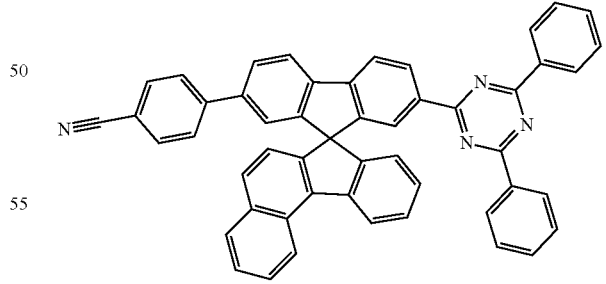
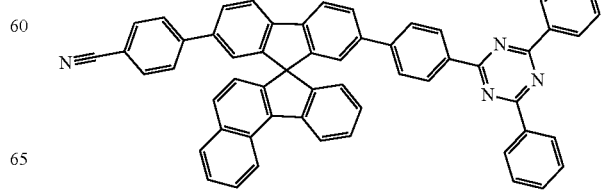

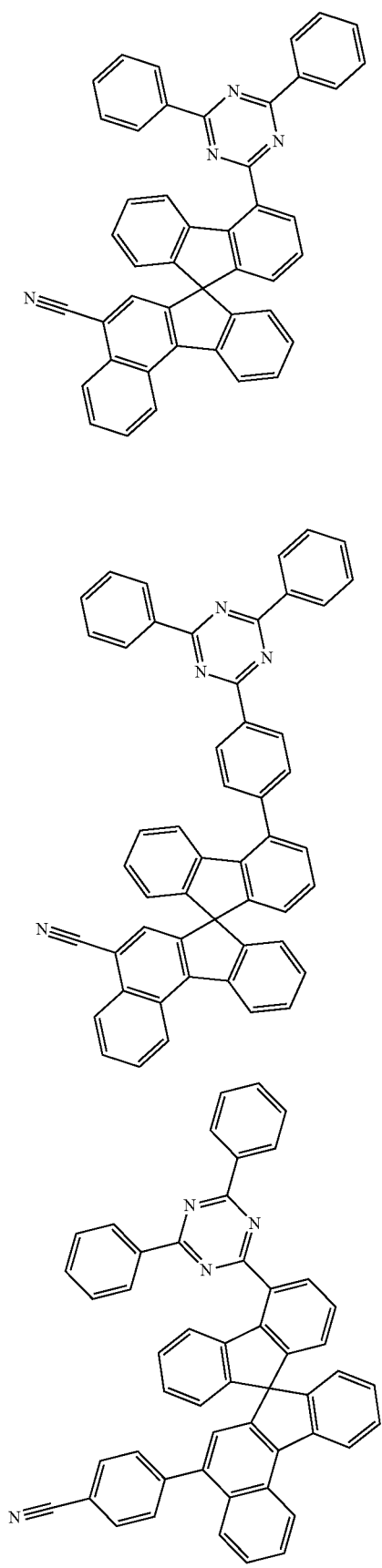
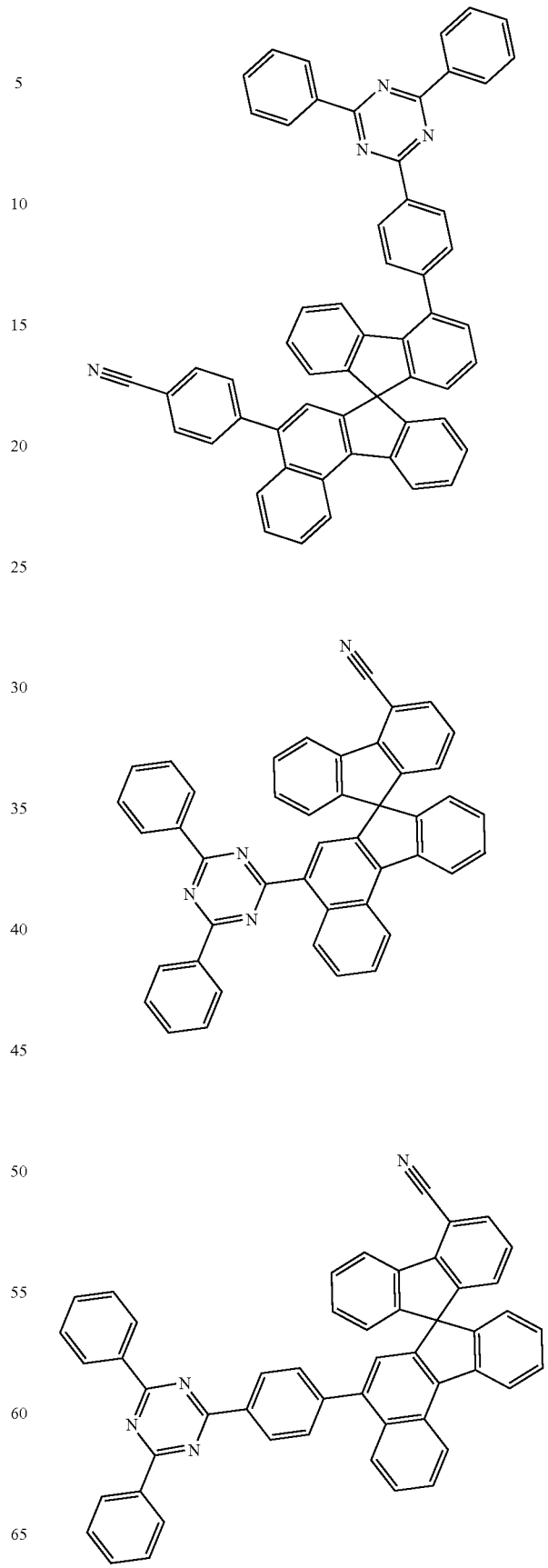

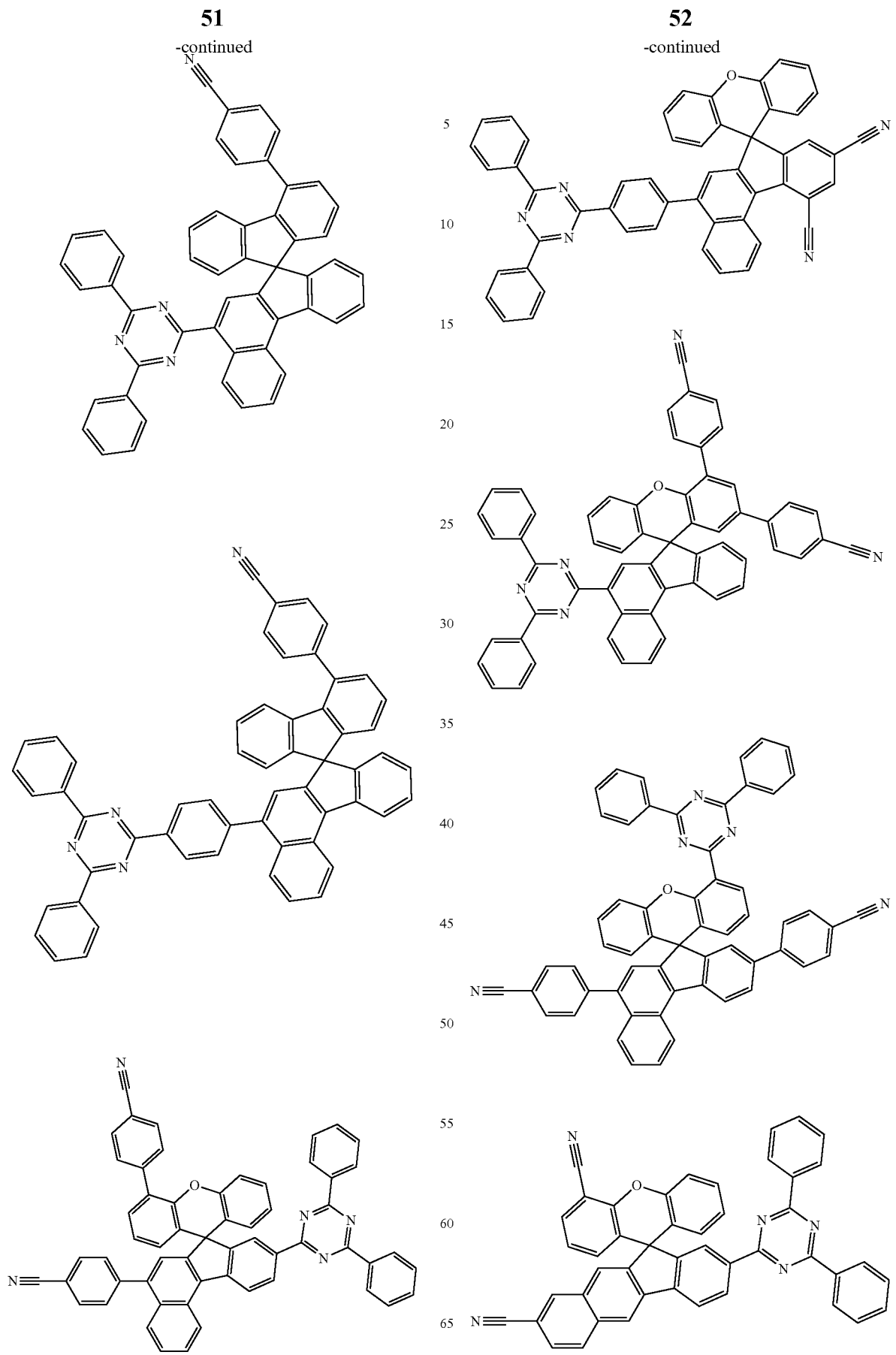

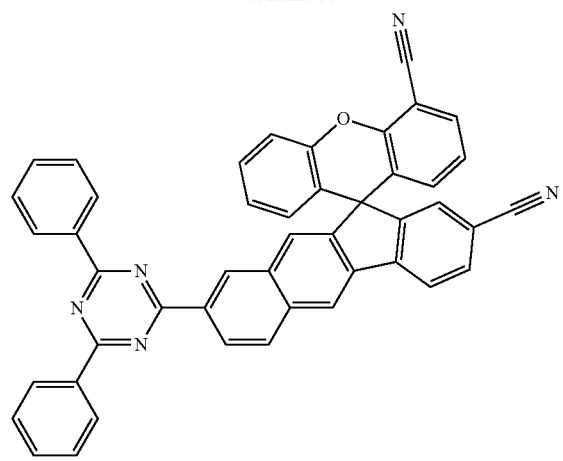
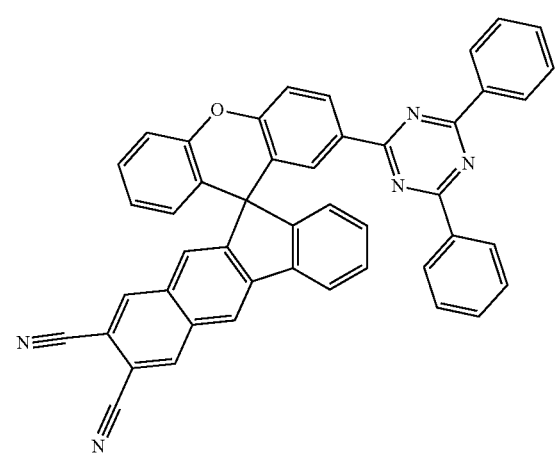
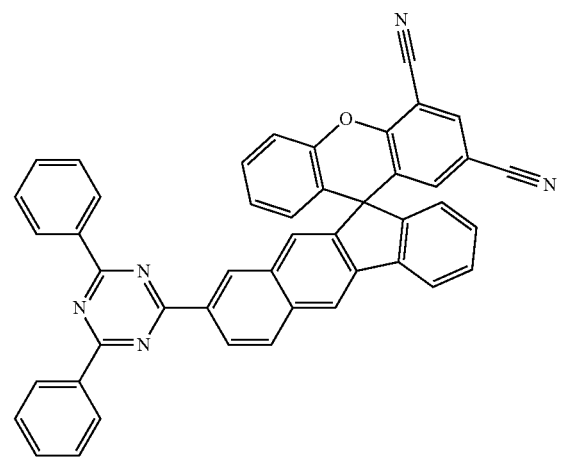
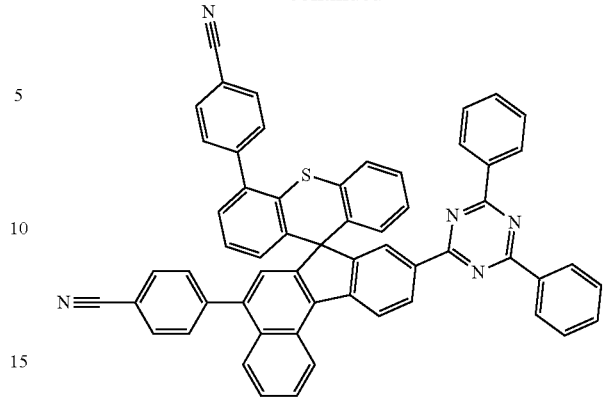
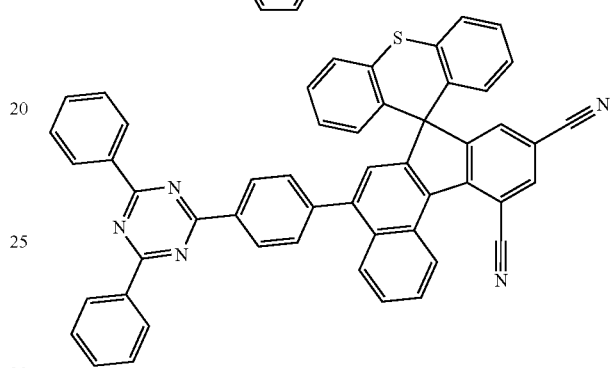
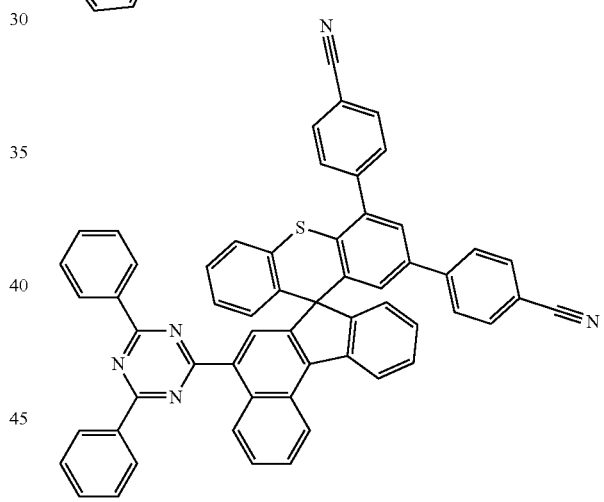
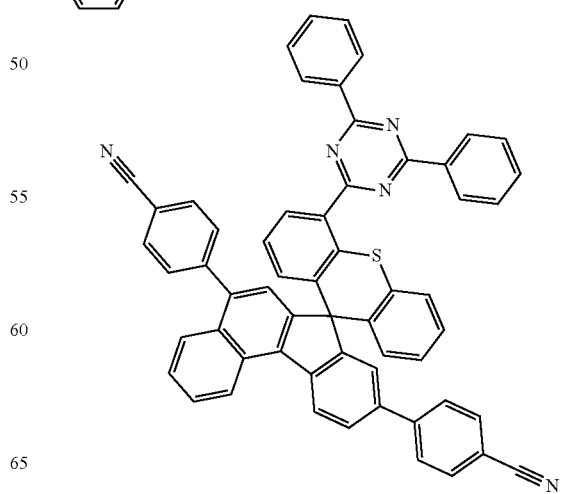

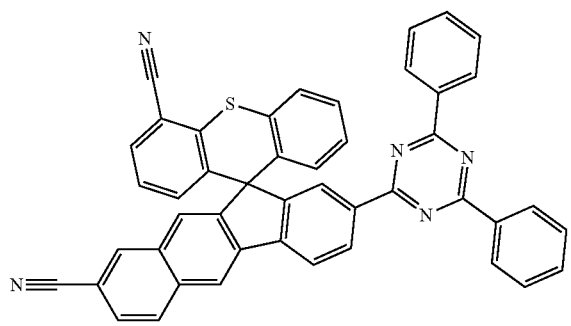
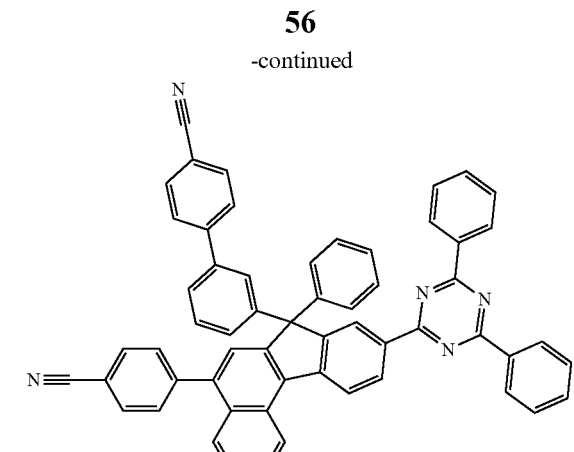
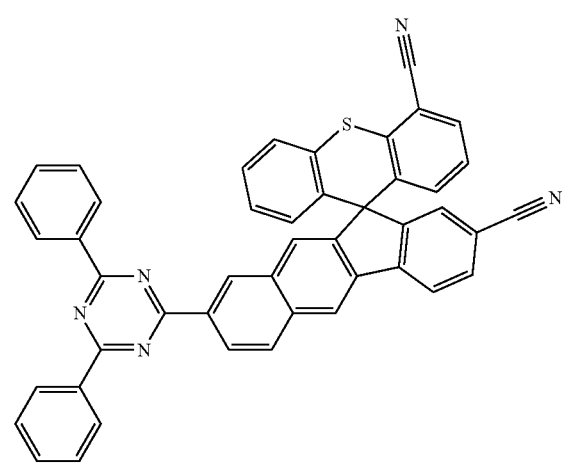
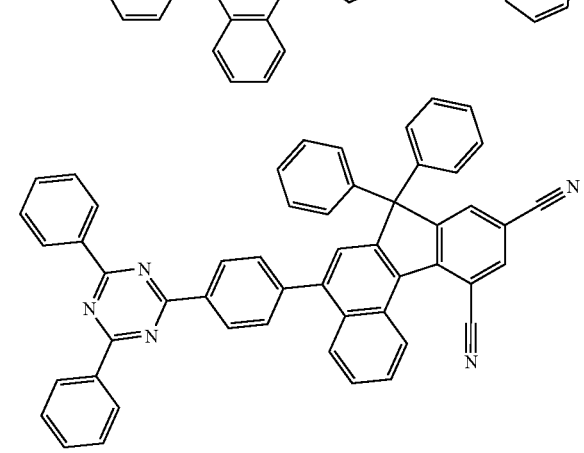
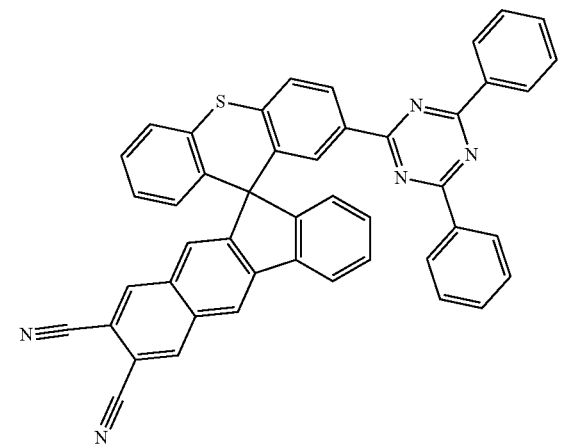
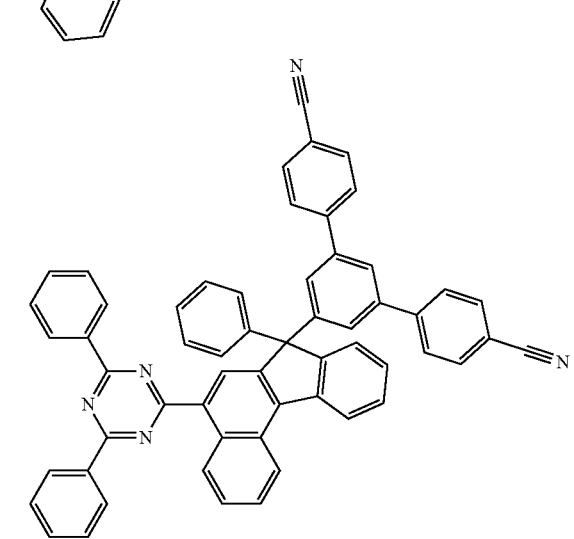
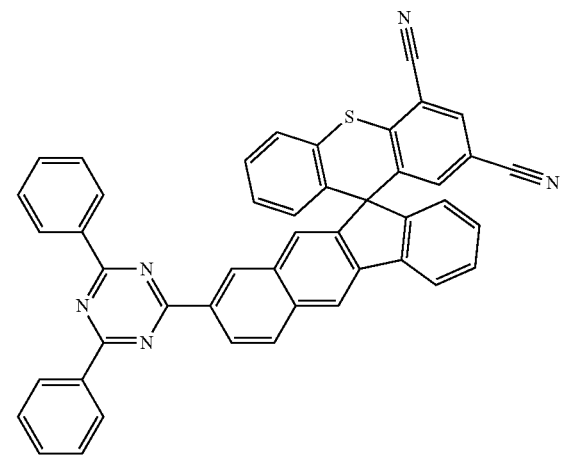
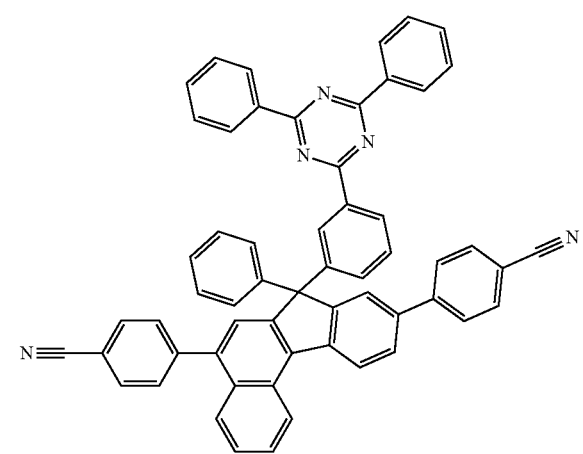

-continued
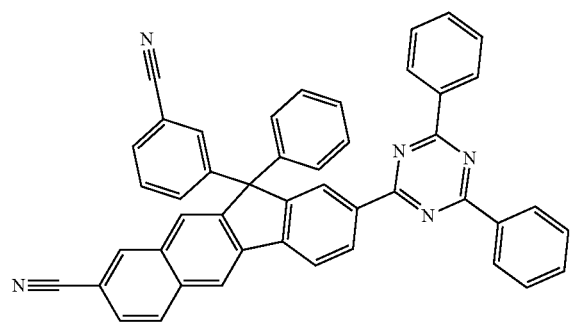
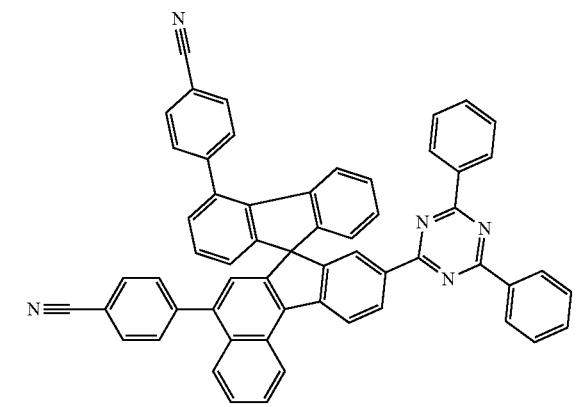
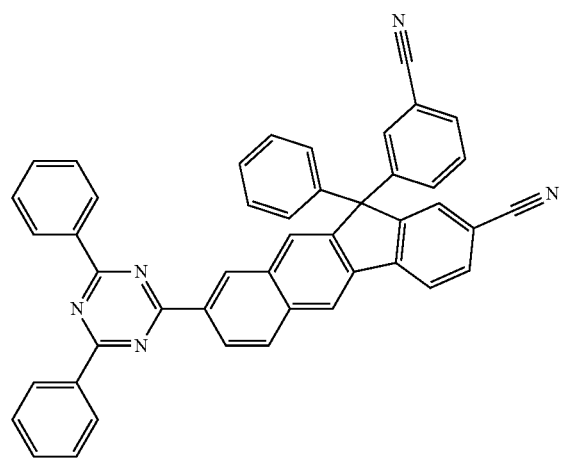
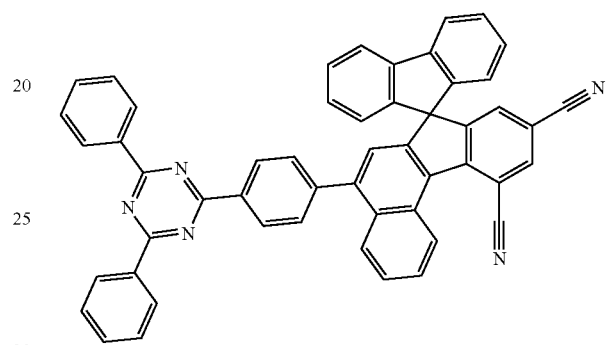
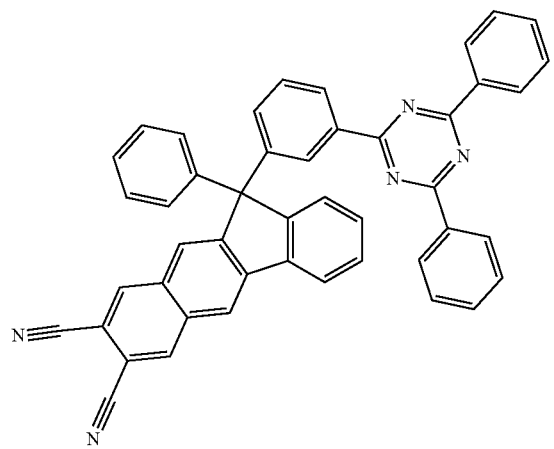
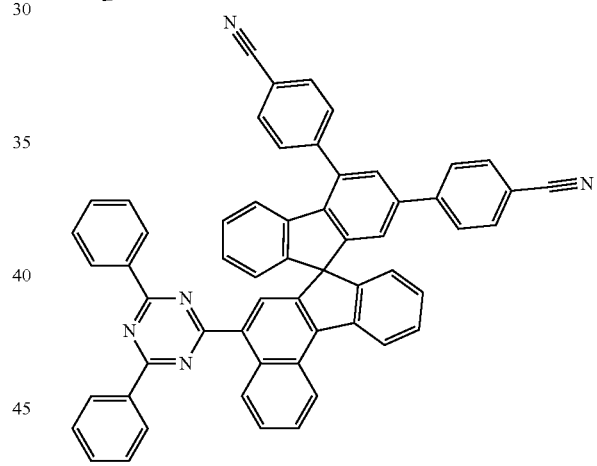
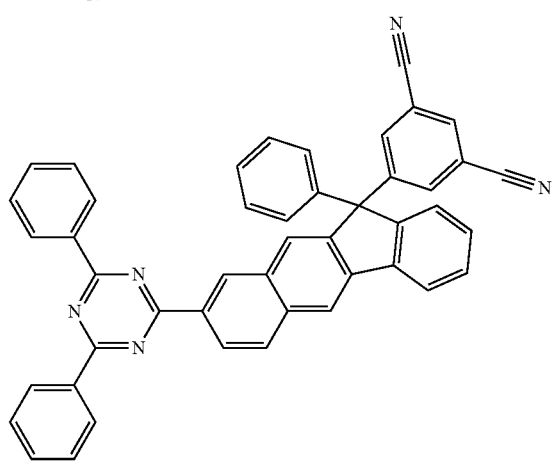
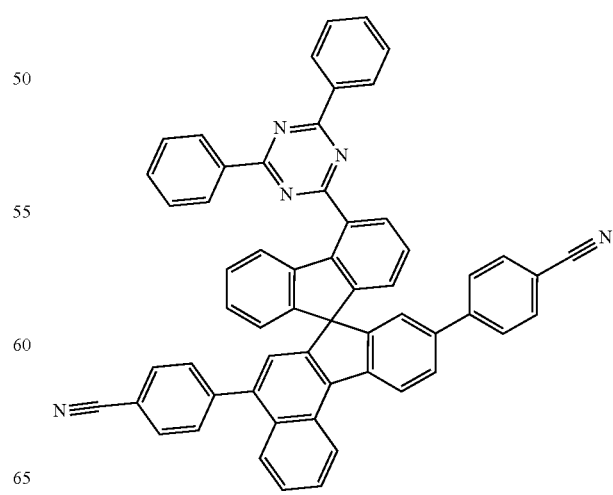

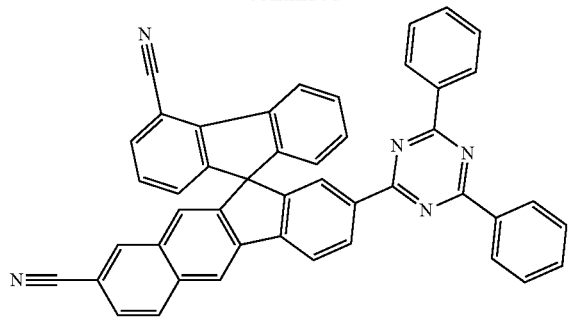

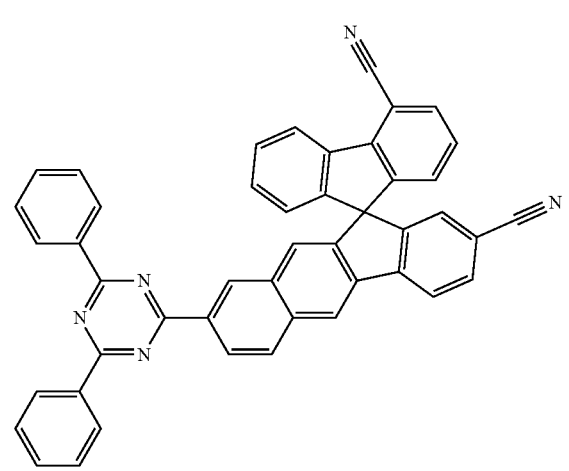

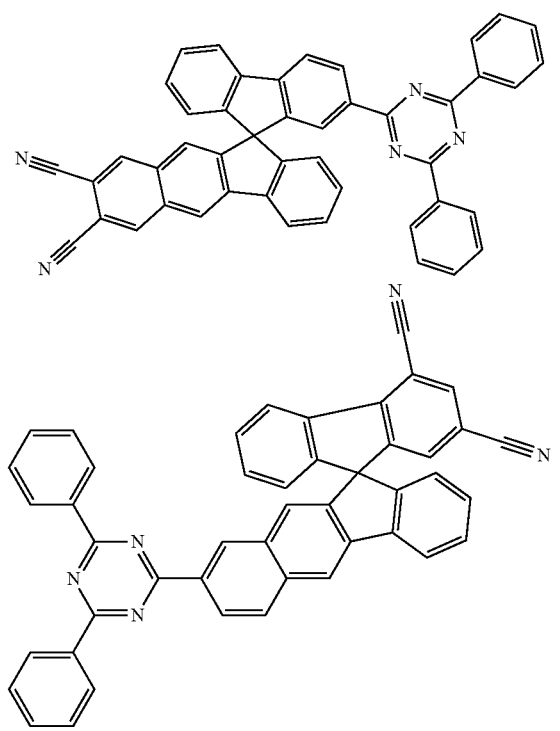

Meanwhile, the compound represented by Chemical Formula 1, wherein n1 and n3 are 1, and n2 and n4 are 0, can be prepared, for example, according to the preparation method as shown in the following Reaction Scheme 1.

Reaction Scheme 1

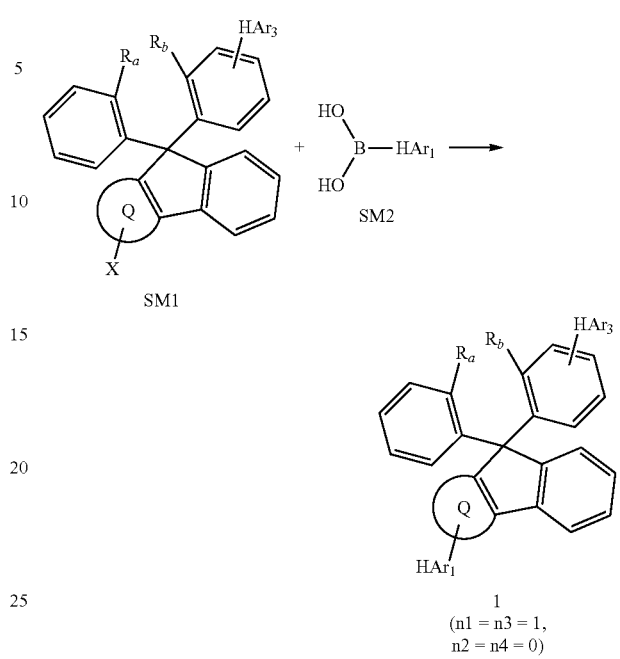

In Reaction Scheme 1, X is a halogen, preferably bromo or chloro, and the definition of each substituent is as defined above.

Specifically, the compound represented by Chemical Formula 1 is prepared by a Suzuki coupling reaction of starting materials SM1 and SM2. At this time, the Suzuki coupling reaction is preferably performed under a palladium catalyst and a base, and the reactive group for the reaction can be modified into a reactive group known in the art. Such a preparation method can be further specified in preparation examples described hereinafter.

In another embodiment of the invention, there is provided an organic light emitting device including the compound represented by Chemical Formula 1 described above. As an example, there is provided an organic light emitting device including: a first electrode; a second electrode provided opposite to the first electrode; and one or more organic material layers provided between the first electrode and the second electrode, wherein one or more layers of the organic material layers includes the compound represented by Chemical Formula 1.

The organic material layer of the organic light emitting device of the present invention may have a single layer structure, or it may have a multilayered structure in which two or more organic material layers are stacked. For example, the organic light emitting device of the present invention may have a structure including a hole injection layer, a hole transport layer, a light emitting layer, an electron transport layer, an electron injection layer, and the like as the organic material layer. However, the structure of the organic light emitting device is not limited thereto, and it may include a smaller number of organic layers.

Further, the organic material layer may include a hole transport layer, a light emitting layer, and an electron transport layer, and the electron transport layer includes the compound represented by Chemical Formula 1.

Further preferably, the organic material layer may include a hole injection layer, a hole transport layer, a light emitting layer, an electron transport layer, and an electron injection layer, and the electron transport layer includes the compound represented by Chemical Formula 1.

Further preferably, the organic material layer may include a hole injection layer, a hole transport layer, a light emitting layer, and an electron injection and transport layer, and the electron injection and transport layer includes the compound represented by Chemical Formula 1.

The organic material layer of the organic light emitting device of the present invention may have a single layer structure, or it may have a multilayered structure in which two or more organic material layers are stacked.

For example, the organic light emitting device of the present invention may have a structure further including a hole injection layer and a hole transport layer provided between the first electrode and the light emitting layer, and an electron transport layer and an electron injection layer provided between the light emitting layer and the second electrode, in addition to the light emitting layer. However, the structure of the organic light emitting device is not limited thereto, and it may include a smaller number of organic layers or a larger number of organic layers.

Further, the organic light emitting device according to the present invention may be a normal type of organic light emitting device in which an anode, one or more organic material layers, and a cathode are sequentially stacked on a substrate. In addition, the organic light emitting device according to the present invention may be an inverted type of organic light emitting device in which a cathode, one or more organic material layers, and an anode are sequentially stacked on a substrate. For example, the structure of an organic light emitting device according to an embodiment of the present disclosure is illustrated in FIGS. 1 and 2.

FIG. 1 shows an example of an organic light emitting device including a substrate 1, an anode 2, a hole transport layer 3, a light emitting layer 4, an electron injection and transport layer 5, and a cathode 6. In such a structure, the compound represented by Chemical Formula 1 may be included in the electron injection and transport layer 5.

FIG. 2 shows an example of an organic light emitting device including a substrate 1, an anode 2, a hole injection layer 7, a hole transport layer 3, a light emitting layer 4, an electron injection and transport layer 5, and a cathode 6. In such a structure, the compound represented by Chemical Formula 1 may be included in the electron injection and transport layer 5.

The organic light emitting device according to the present invention may be manufactured by materials and methods known in the art, except that one or more layers of the organic material layers include the compound represented by Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer, and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming organic material layers including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer, and an anode material on a substrate.

Further, the compound represented by Chemical Formula 1 may be formed into an organic layer by a solution coating method as well as a vacuum deposition method at the time of manufacturing an organic light emitting device. Herein, the solution coating method means spin coating, dip coating, doctor blading, inkjet printing, screen printing, a spray method, roll coating, or the like, but is not limited thereto.

In addition to such a method, the organic light emitting device may be manufactured by sequentially depositing a cathode material, an organic material layer, and an anode material on a substrate (International Publication WO2003/012890). However, the manufacturing method is not limited thereto.

As an example, the first electrode is an anode and the second electrode is a cathode, or alternatively, the first electrode is a cathode and the second electrode is an anode.

As the anode material, generally, a material having a large work function is preferably used so that holes can be smoothly injected into the organic material layer. Specific examples of the anode material include metals such as vanadium, chromium, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline; and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al; and the like, but are not limited thereto.

The hole injection layer is a layer for injecting holes from the electrode, and the hole injection material is preferably a compound which has a capability of transporting the holes, thus has a hole injecting effect in the anode and an excellent hole injecting effect to the light emitting layer or the light emitting material, prevents excitons produced in the light emitting layer from moving to an electron injection layer or the electron injection material, and is excellent in the ability to form a thin film. It is preferable that a HOMO (highest occupied molecular orbital) of the hole injection material is between the work function of the anode material and a HOMO of a peripheral organic material layer. Specific examples of the hole injection material include a metal porphyrin, an oligothiophene, an arylamine-based organic material, a hexanitrilehexaazatriphenylene-based organic material, a quinacridone-based organic material, a perylene-based organic material, anthraquinone, polyaniline, a polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is preferably a material which may receive holes and electrons transported from a hole transport layer and an electron transport layer, respectively, and combine the holes and the electrons to emit light in a visible ray region, and has good quantum efficiency to fluorescence or phosphorescence. Specific examples thereof include an 8-hydroxy-quinoline aluminum complex (Alq3); a carbazole-based compound; a dimerized styryl compound; BAlq; a 10-hydroxybenzoquinoline-metal compound; a benzoxazole-, benzothiazole-, and benzimidazole-based compound; a poly(p-phenylene vinylene) (PPV)-based polymer; a spiro compound; polyfluorene, rubrene, and the like, but are not limited thereto.

The light emitting layer may include a host material and a dopant material as described above. The host material may further include a fused aromatic ring derivative, a heterocyclic-containing compound, or the like. Specific examples of the fused aromatic ring derivatives include anthracene derivatives, pyrene derivatives, naphthalene derivatives, pentacene derivatives, phenanthrene compounds, fluoranthene compounds, and the like. Examples of the heterocyclic-containing compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specifically, the aromatic amine derivative is a substituted or unsubstituted fused aromatic ring derivative having an arylamino group, and examples thereof include pyrene, anthracene, chrysene, periflanthene, and the like, which have an arylamino group. The styrylamine compound is a compound where at least one arylvinyl group is substituted in a substituted or unsubstituted arylamine, in which one or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, the metal complex includes an iridium complex, a platinum complex, and the like, but is not limited thereto.

The electron injection and transport layer is a layer that simultaneously serves as an electron transport layer and an electron injection layer that injects electrons from an electrode and transports the received electrons to the light emitting layer, and is formed on the light emitting layer or the hole blocking layer. As such an electron injecting and transporting material, a compound represented by Chemical Formula 1, which is a material capable of receiving electrons from a cathode well and transferring them to a light emitting layer, is a material having high mobility for electrons. In addition, the electron injection and transport layer may further include a metal complex compound in addition to the compound represented by Chemical Formula 1.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato)beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

In this case, the compound represented by Chemical Formula 1 and the metal complex compound may be used in a weight ratio of 1:9 to 9:1.

Further, the electron injection and transport layer may be formed of separate layers such as an electron injection layer and an electron transport layer. In this case, the electron transport layer is formed on the light emitting layer or the hole blocking layer, and the compound represented by Chemical Formula 1 may be used as the electron transport material included in the electron transport layer. In addition, the electron injection layer is formed on the electron transport layer, and for the electron injection materials included in the electron injection layer, LiF, NaCl, CsF, $Li_2O$, BaO, fluorenone, anthraquinodimethane, diphenoquinone, thiopyran dioxide, oxazole, oxadiazole, triazole, imidazole, perylenetetracarboxylic acid, fluorenylidene methane, anthrone, and the like, and their derivatives, metal complex compounds, nitrogen-containing 5-membered ring derivatives, and the like can be used.

The organic light emitting device according to the present invention may be a front-side emission type, a back-side emission type, or a double-side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device containing the same will be described in detail in the following examples. However, these examples are presented for illustrative purposes only, and are not intended to limit the scope of the present invention.

Preparation Example 1: Preparation of Compound E1

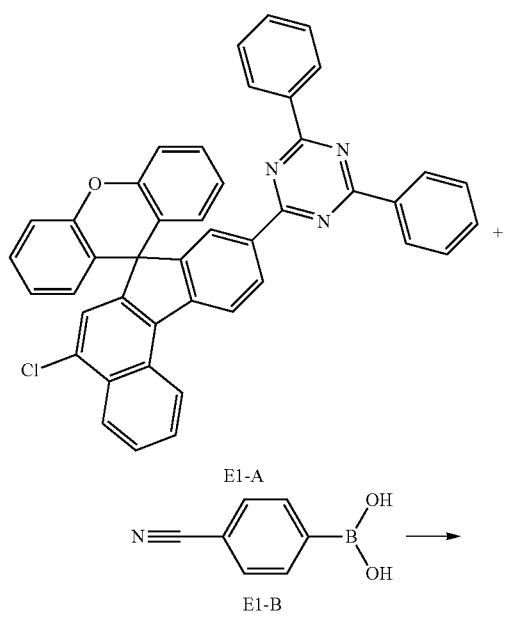

-continued

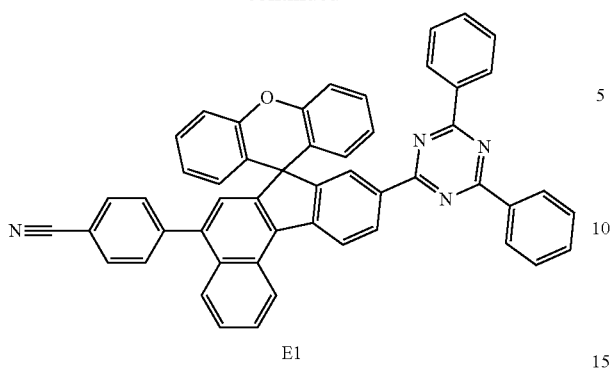

E1

After the compound E1-A (20 g, 15.4 mmol) and the compound E1-B (2.3 g, 15.4 mmol) were completely dissolved in tetrahydrofuran (200 mL), potassium carbonate (6.4 g, 46.2 mmol) dissolved in water (50 mL) was added thereto. After adding tetrakistriphenyl-phosphino palladium (0.53 g, 0.463 mmol), the mixture was heated and stirred for 8 hours. After lowering the temperature to room temperature and terminating the reaction, the potassium carbonate solution was removed to filter a white solid. The filtered white solid was washed twice with each of tetrahydrofuran and ethyl acetate to prepare compound E1 (17.0 g, yield 77%).

MS $[M+H]^+$=715

Preparation Example 2: Preparation of Compound E2

-continued

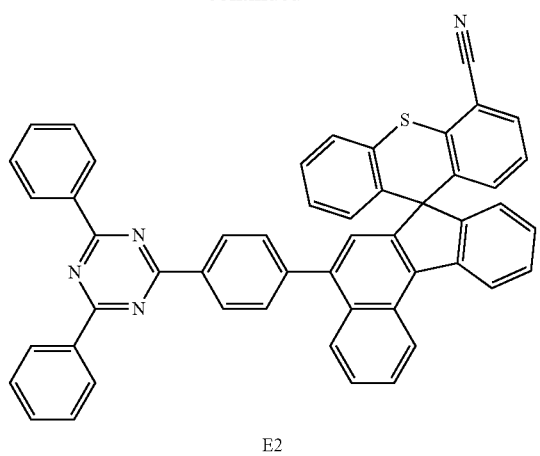

E2

A compound E2 was prepared in the same method as in Preparation Example 1 using E2-A instead of the starting material E1-A and E2-B instead of the starting material E1-B in Preparation Example 1.

MS $[M+H]^+$=731

Preparation Example 3: Preparation of Compound E3

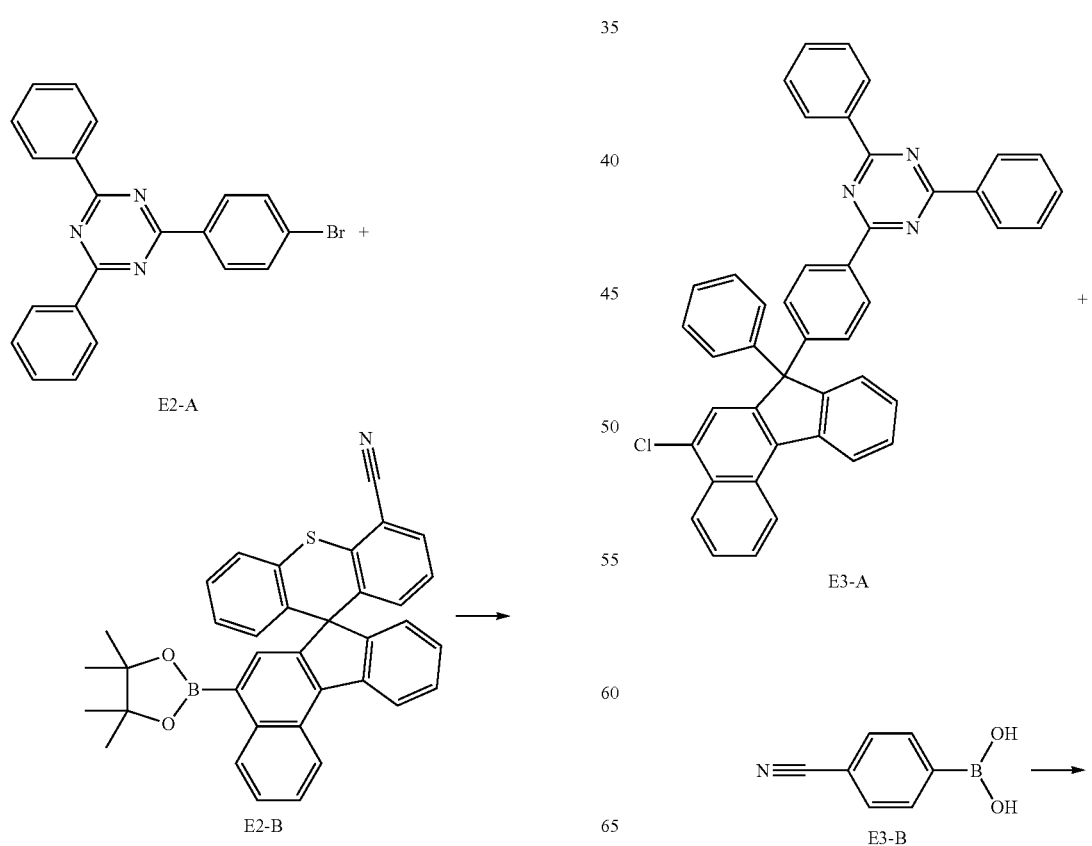

-continued

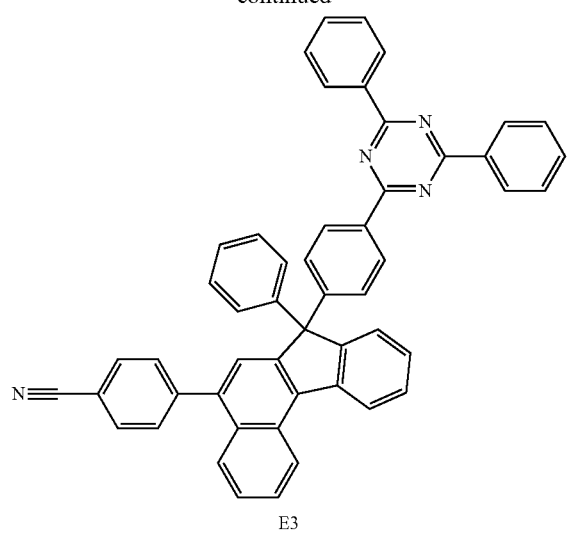

E3

A compound E3 was prepared in the same method as in Preparation Example 1 using E3-A instead of the starting material E1-A and E3-B instead of the starting material E1-B in Preparation Example 1.

MS [M+H]$^+$=701

Preparation Example 4: Preparation of Compound E4

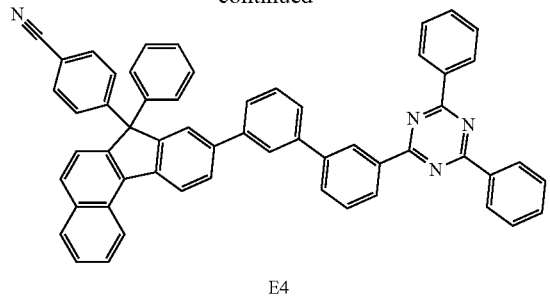

E4-A

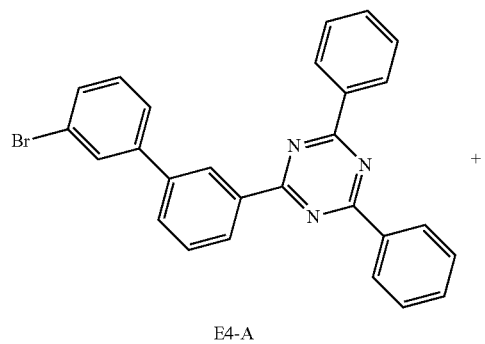

E4-B

-continued

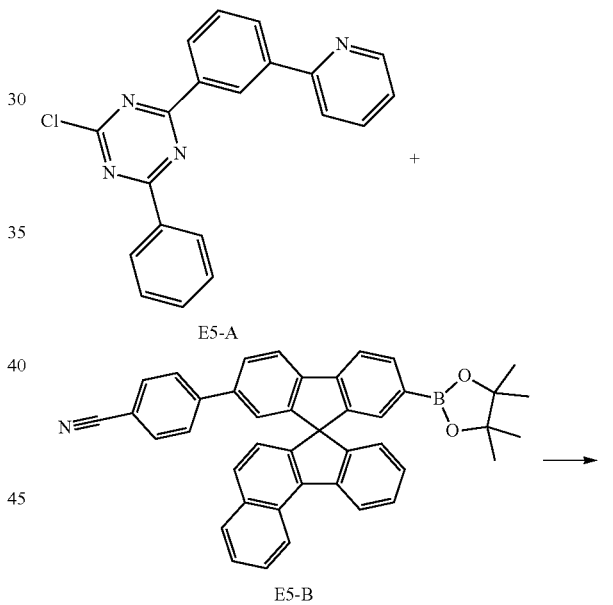

E4

A compound E4 was prepared in the same method as in Preparation Example 1 using E4-A instead of the starting material E1-A and E4-B instead of the starting material E1-B in Preparation Example 1.

MS [M+H]$^+$=777

Preparation Example 5: Preparation of Compound E5

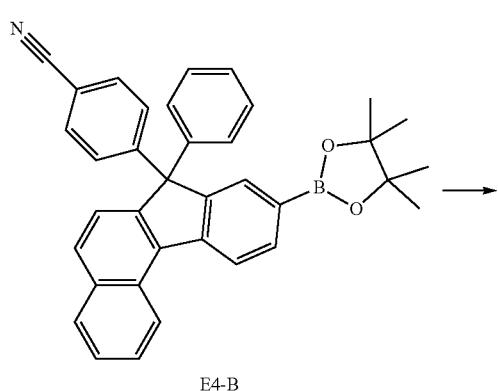

E5-A

E5-B

E5

A compound E5 was prepared in the same method as in Preparation Example 1 using E5-A instead of the starting material E1-A and E5-B instead of the starting material E1-B in Preparation Example 1.

MS [M+H]$^+$=776

Preparation Example 6: Preparation of Compound E6

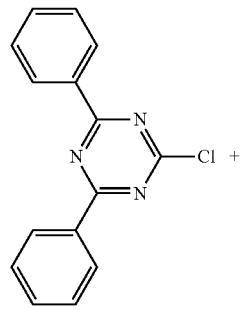

E6-A

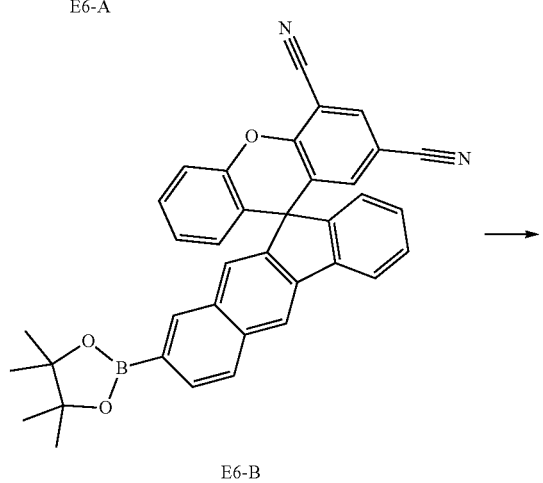

E6-B

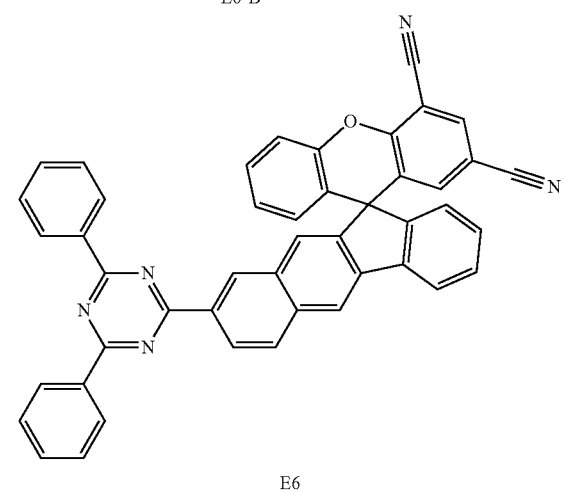

E6

A compound E6 was prepared in the same method as in Preparation Example 1 using E6-A instead of the starting material E1-A and E6-B instead of the starting material E1-B in Preparation Example 1.

MS [M+H]$^+$=664

Example 1

A glass substrate on which ITO (indium tin oxide) was coated as a thin film to a thickness of 1000 Å was put into distilled water in which a detergent was dissolved, and ultrasonically cleaned. In this case, a product manufactured by Fischer Co. was used as the detergent, and as the distilled water, distilled water filtered twice using a filter manufactured by Millipore Co. was used. After the ITO was cleaned for 30 minutes, ultrasonic cleaning was repeated twice using distilled water for 10 minutes. After the cleaning with distilled water was completed, the substrate was ultrasonically cleaned with solvents of isopropyl alcohol, acetone, and methanol, then dried, and then transferred to a plasma cleaner. Subsequently, the substrate was cleaned for 5 minutes using oxygen plasma, and then transferred to a vacuum depositor.

On the prepared ITO transparent electrode, the following HI-A compound was thermally vacuum-deposited to a thickness of 600 Å to form a hole injection layer. The following HAT compound at 50 Å and the following HT-A compound at 60 Å were sequentially vacuum deposited on the hole injection layer to form a first hole transport layer and a second hole transport layer.

Subsequently, a light emitting layer was formed by vacuum-depositing the following BH compound and BD compound at a weight ratio of 25:1 on the hole transport layer with a thickness of 200 Å.

On the light emitting layer, the compound E1 prepared in Preparation Example 1 and the following LiQ compound were vacuum deposited at a weight ratio of 1:1 to form an electron injection and transport layer with a thickness of 350 Å. On the electron injection and transport layer, lithium fluoride (LiF) with a thickness of 10 Å and aluminum with a thickness of 1000 Å were sequentially deposited to form a cathode.

In the above-mentioned process, the vapor deposition rate of the organic material was maintained at 0.4 to 0.9 Å/s, the deposition rate of lithium fluoride of the cathode was maintained at 0.3 Å/sec, the deposition rate of aluminum was maintained at 2 Å/s, and the degree of vacuum during the deposition was maintained at $1\times10^{-7}$ to $5\times10^{-5}$ Torr, thereby manufacturing an organic light emitting device.

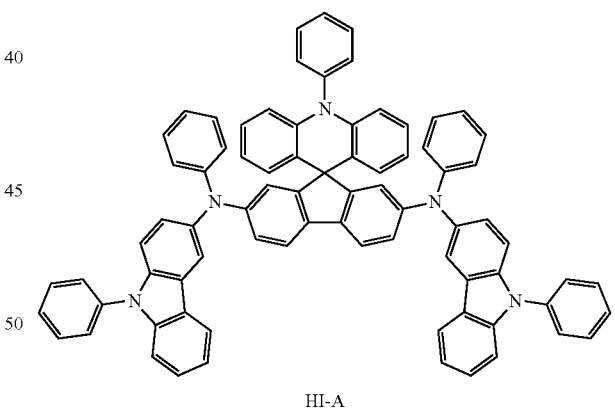

HI-A

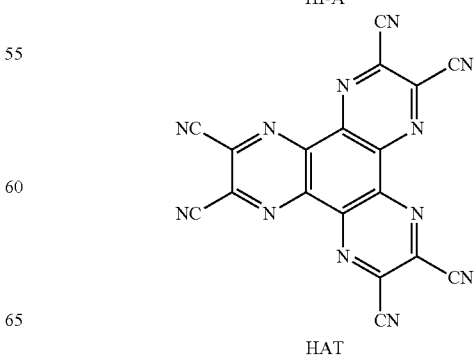

HAT

-continued
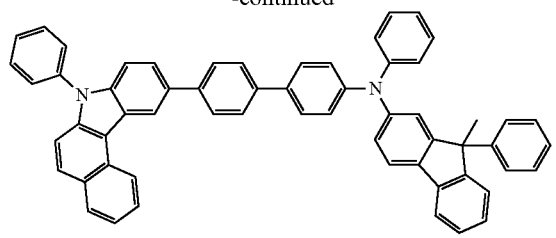
HT-A
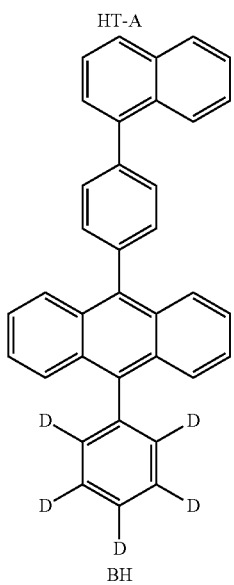
BH
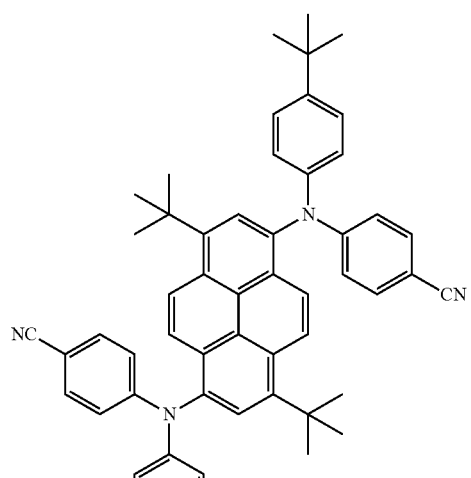
BD
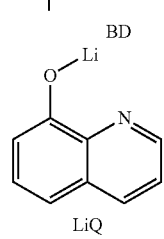
LiQ
Example 2 to 6
An organic light emitting device was manufactured in the same manner as in Example 1, except that the compounds E2 to E6 shown in Table 1 below were used instead of compound E1 in Example 1.
The structures of the compounds used in the Examples 1 to 6 are as follows.
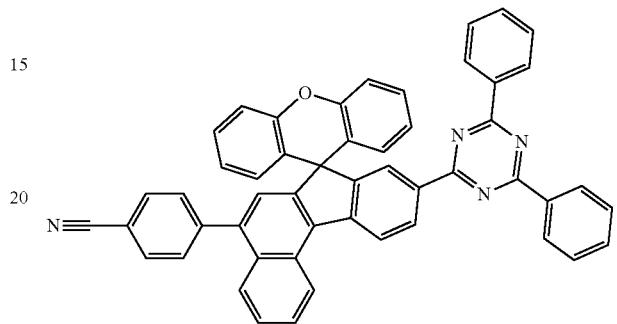
E1
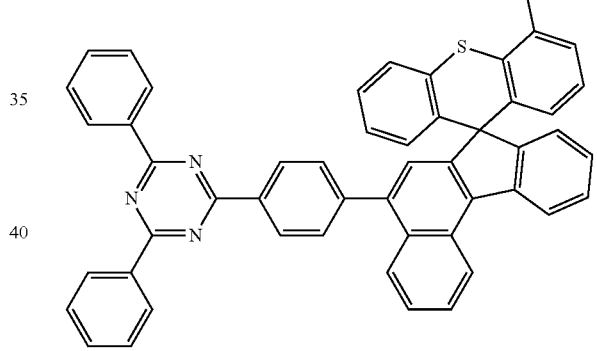
E2
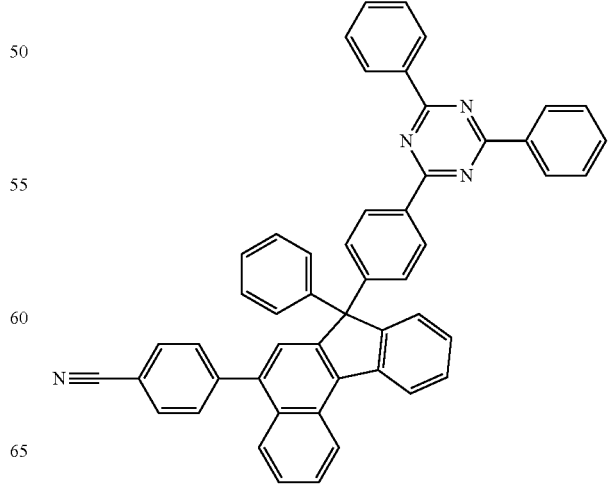
E3

-continued
E4
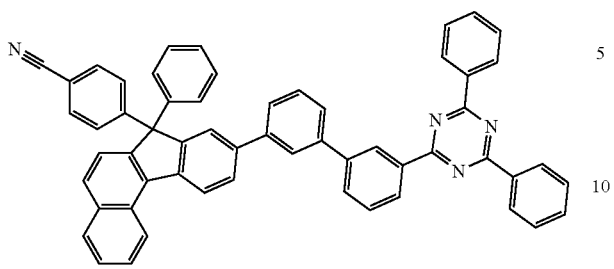
E5
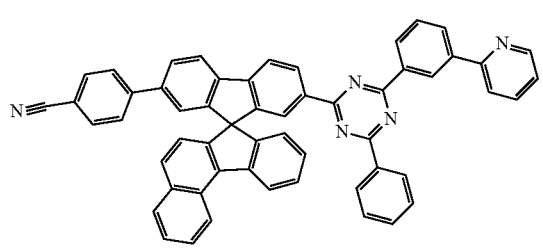
E6
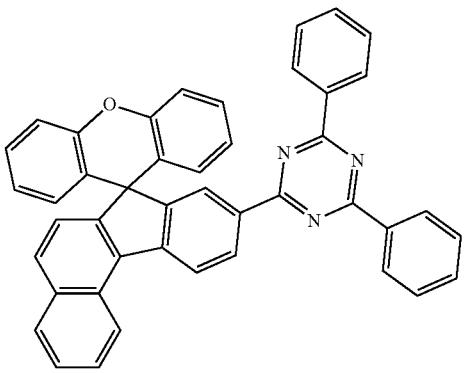
Comparative Examples 1 to 5
An organic light emitting device was manufactured in the same manner as in Example 1, except that the compounds ET-A to ET-E shown in Table 1 below were used instead of Compound E1 in Example 1.
The structures of the compounds ET-A to ET-E used in Comparative Examples 1 to 5 are as follows.
ET-A
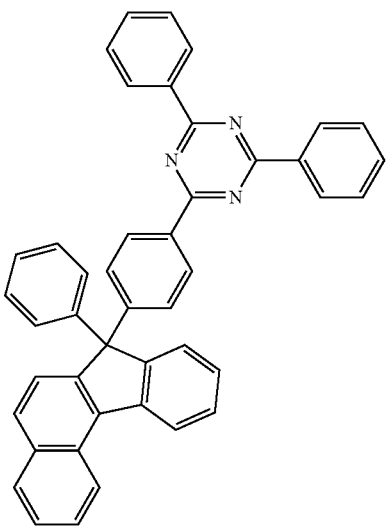
ET-B
ET-C
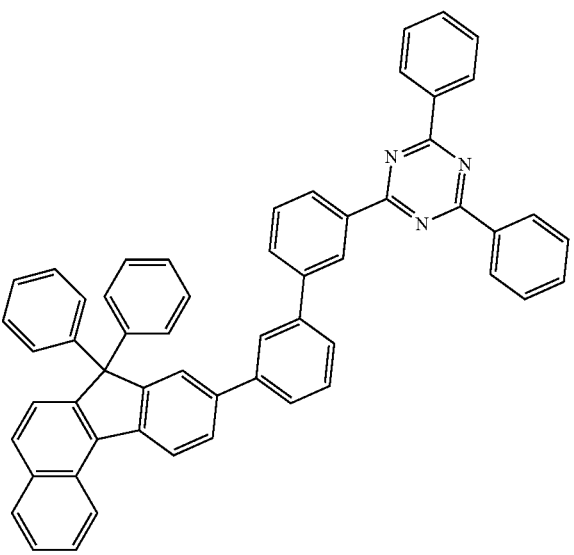

-continued

ET-D

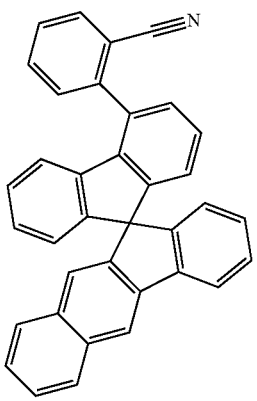

ET-E

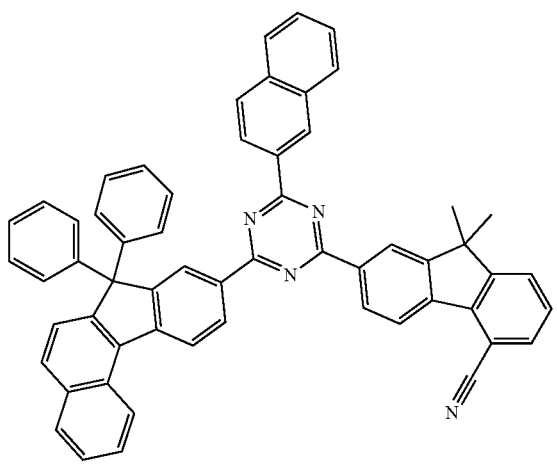

Experimental Example

For the organic light emitting devices manufactured in the Examples 1 to 6 and Comparative Examples 1 to 5 above, the driving voltage and luminous efficiency at a current density of 10 mA/cm² and the time required for the luminance to be reduced to 90% of the initial luminance (T90) at a current density of 20 mA/cm² were measured, and the results are shown in Table 1 below.

TABLE 1

| Compound (Electron injection and transport layer) | Voltage (V @20 mA/cm²) | Efficiency (cd/A @10 mA/cm²) | Color coordinates (x, y) | Lifespan (T90) (h @20 mA/cm²) |
|---|---|---|---|---|
| Example 1 | E1 | 4.54 | 5.14 | (0.142, 0.096) | 275 |
| Example 2 | E2 | 4.40 | 5.45 | (0.142, 0.096) | 204 |
| Example 3 | E3 | 4.38 | 5.51 | (0.142, 0.096) | 193 |
| Example 4 | E4 | 4.45 | 5.55 | (0.142, 0.096) | 176 |
| Example 5 | E5 | 4.59 | 5.06 | (0.142, 0.096) | 281 |
| Example 6 | E6 | 4.68 | 4.92 | (0.142, 0.097) | 322 |
| Comparative Example 1 | ET-A | 4.34 | 5.45 | (0.142, 0.096) | 33 |
| Comparative Example 2 | ET-B | 4.40 | 5.50 | (0.142, 0.096) | 39 |
| Comparative Example 3 | ET-C | 4.49 | 5.06 | (0.142, 0.096) | 69 |
| Comparative Example 4 | ET-D | 5.04 | 3.75 | (0.142, 0.096) | 154 |
| Comparative Example 5 | ET-E | 4.60 | 4.46 | (0.142, 0.096) | 169 |

As shown in Table 1, the organic light-emitting devices of the examples using the compound of the present disclosure as a layer material capable of electron injection and electron transport at the same time, exhibited excellent device properties, as compared with an organic light emitting device of the comparative example using compounds not included in Chemical Formula 1.

Specifically, it can be confirmed that the organic light-emitting devices of the examples show significantly superior lifespan characteristics compared to the organic light-emitting devices of Comparative Examples 1 to 3 employing a compound having no cyano group, and show significantly higher efficiency than that of the organic light emitting device of Comparative Example 4 employing a compound having no triazinyl group.

In addition, it can be confirmed that the organic light-emitting devices of the examples show superior efficiency and lifespan characteristics compared to the organic light-emitting device of Comparative Example 5 employing a compound which has a triazinyl group and a cyano group with a different substitution position from the compound represented by Chemical Formula 1. In general, considering that the luminous efficiency and lifespan characteristics of the organic light emitting devices have a trade-off relationship with each other, it can be seen that the organic light emitting devices employing the compound represented by Chemical Formula 1 exhibit significantly improved device characteristics as compared with the devices of the comparative examples.

DESCRIPTION OF REFERENCE NUMBERS

1: substrate 2: anode
3: hole transport layer 4: light emitting layer
5: electron injection and transport layer 6: cathode
7: hole injection layer

What is claimed is:
1. A compound represented by the following Chemical Formula 1:

Chemical Formula 1

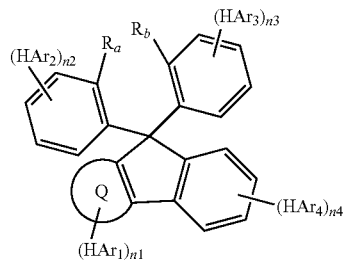

wherein in Chemical Formula 1,
Q is naphthalene, $R_a$ and $R_b$ are each hydrogen, or are bonded to each other to form Y,
where Y is single bond, O, or S,
one of $HAr_1$ to $HAr_4$ is the following Chemical Formula 2, one of the others is the following Chemical Formula 3, and the rest are each independently Chemical Formula 2 or 3, Chemical Formula 2

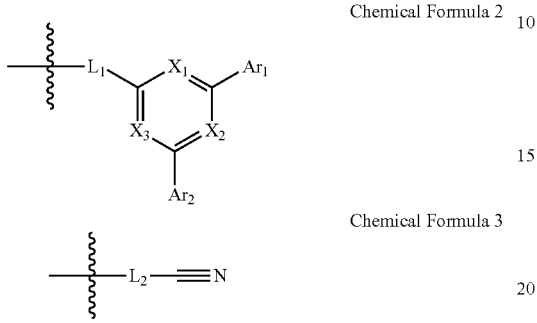

Chemical Formula 3

$$\text{─}\!\!\!\!\!\xi\ L_2\text{─}\!\!\equiv\!\!N$$

wherein, in Chemical Formula 2 and 3,
$L_1$ and $L_2$ are each independently a single bond; or a substituted or unsubstituted $C_{6-60}$ arylene,
$X_1$ to $X_3$ are each independently N or CR, and at least two of $X_1$ to $X_3$ are N,
$Ar_1$ and $Ar_2$ are each independently a $C_{6-60}$ aryl unsubstituted, or substituted with pyridinyl,
R is hydrogen or deuterium,
n1 to n4 are each an integer of 0 to 2,
n1+n2+n3+n4 is an integer of 2 to 8,
provided that when $R_a$ and $R_b$ are each hydrogen, one of $HAr_1$ to $HAr_4$ is Chemical Formula 2, and the rest are Chemical Formula 3, and
provided that when $R_a$ and $R_b$ are bonded to each other to form O or S, and when n1 to n4 are each 0 or 1 and n1+n2+n3+n4 is 2, $HAr_1$ to $HAr_3$ are each independently Chemical Formula 2 or 3, and at least one of $HAr_1$ to $HAr_3$ is Chemical Formula 2, and $HAr_4$ is Chemical Formula 3.

2. The compound according to claim 1,
wherein $L_1$ and $L_2$ are each independently single bond, phenylene, or biphenylene.

3. The compound according to claim 1,
wherein $X_1$ to $X_3$ are N.

4. The compound according to claim 1,
wherein $Ar_1$ and $Ar_2$ are each independently phenyl or pyridinylphenyl.

5. The compound according to claim 1,
wherein the compound is represented by the following Chemical Formula 1-1:

[Chemical Formula 1-1]

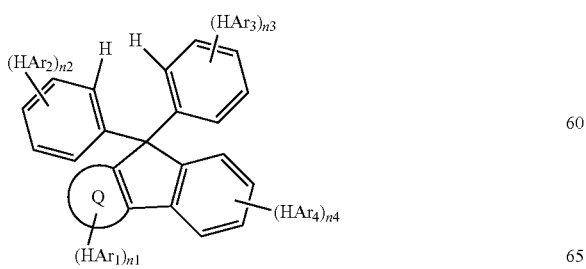

wherein, in Chemical Formula 1-1,
Q is naphthalene,
one of $HAr_1$ and $HAr_2$ is Chemical Formula 2, and the rest is Chemical Formula 3,
$HAr_3$ and $HAr_4$ are each independently Chemical Formula 3,
n1 to n4 are each 0 or 1, and
n1+n2+n3+n4 is 2.

6. The compound according to claim 1,
wherein the compound is represented by the following Chemical Formula 1-2A:

Chemical Formula 1-2A

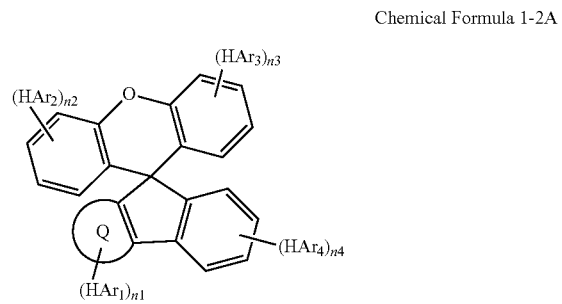

wherein, in Chemical Formula 1-2A,
Q is naphthalene,
$HAr_1$ to $HAr_3$ are each independently Chemical Formula 2 or 3, and at least one of $HAr_1$ to $HAr_3$ is Chemical Formula 2,
$HAr_4$ is Chemical Formula 3,
n1 to n4 are each 0 or 1, and
n1+n2+n3+n4 is 2.

7. The compound according to claim 1,
wherein the compound is represented by Chemical Formula 1-2B:

Chemical Formula 1-2B

wherein, in Chemical Formula 1-2B,
Q is naphthalene,
Y' is single bond, or S,
n1 to n4 are each 0 or 1,
n1+n2+n3+n4 is 2, and
$HAr_1$ to $HAr_4$ are as defined in claim 1.

8. The compound according to claim 1,
wherein n1 and n3 are 1, and n2 and n4 are 0;
n1 and n4 are 1, and n2 and n3 are 0; or
n2 and n3 are 1, and n1 and n4 are 0.

9. The compound according to claim 1,
wherein the compound represented by Chemical Formula 1 is represented by any one of the following Chemical Formulae 4-1 to 4-7:

4-1

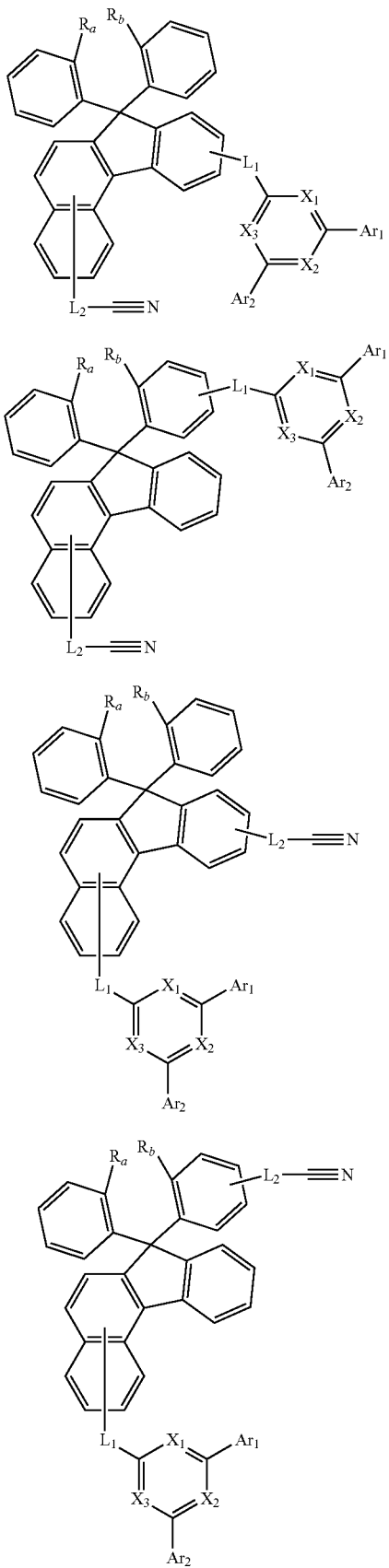

4-2

4-3

4-4

4-5

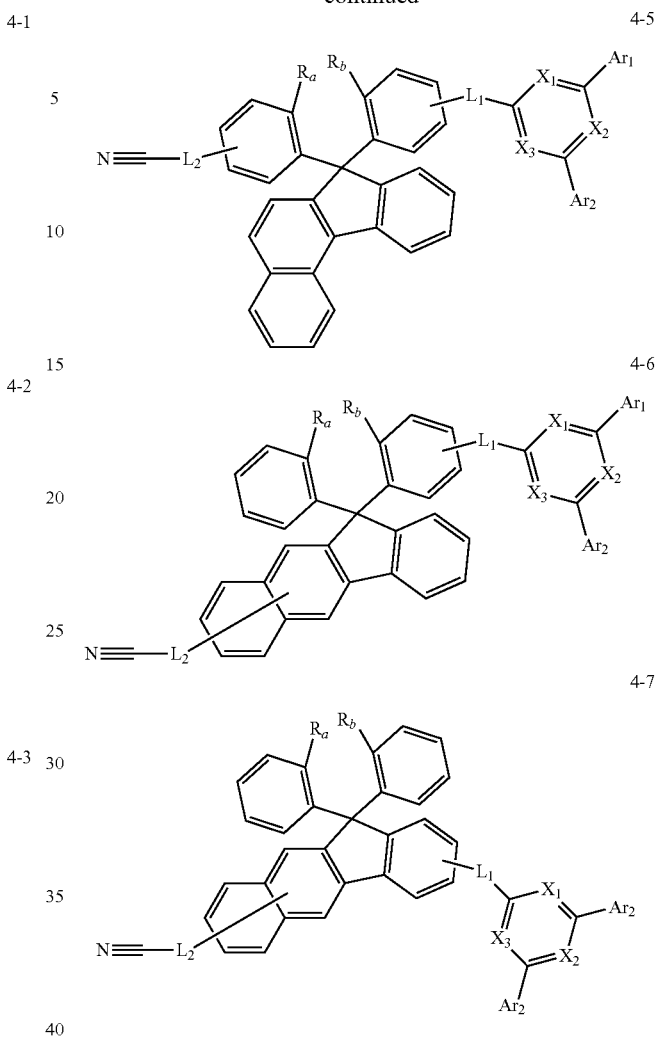

4-6

4-7 wherein, in Chemical Formulae 4-1 to 4-7, $R_a$, $R_b$, $L_1$, $L_2$, $X_1$ to $X_3$, $Ar_1$, and $Ar_2$ are as defined in claim 1, and provided that when $R_a$ and $R_b$ are bonded to each other to form O or S, the compound is represented by one of Chemical Formulae 4-2 to 4-6.

10. The compound according to claim 1, wherein one of $HAr_1$ to $HAr_4$ is Chemical Formula 2, two of the others are Chemical Formula 3, n1 to n4 are each 0, 1, or 2, and n1+n2+n3+n4 is 3.

11. The compound according to claim 1, wherein n1, n2, and n4 are 1, and n3 is 0;

n1, n3, and n4 are 1, and n2 is 0;

n1 is 2, n3 is 1, and n2 and n4 are 0;

n3 is 2, n1 is 1, and n2 and n4 are 0; or n4 is 2, n1 is 1, and n2 and n3 are 0.

12. The compound according to claim 1, wherein the compound represented by Chemical Formula 1 is represented by any one of the following Chemical Formulae 5-1 to 5-7:

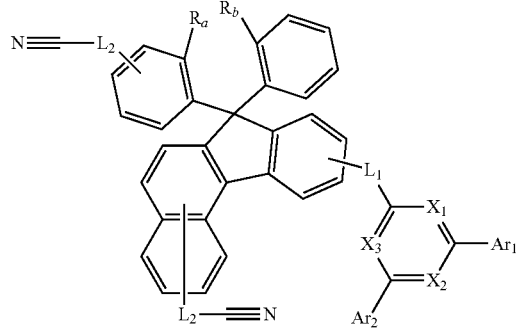
5-1
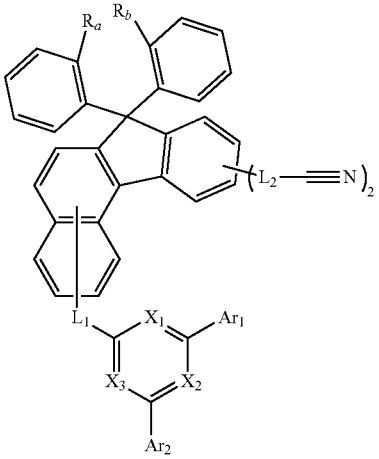
5-5
5-2
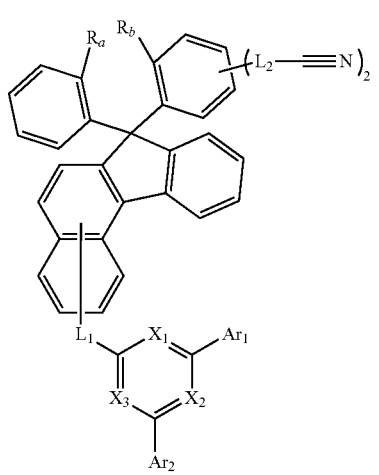
5-6
5-3
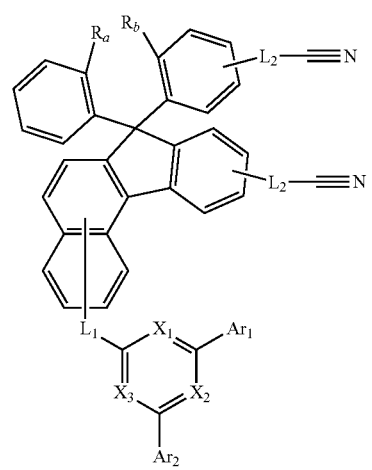
5-7
5-4
wherein, in Chemical Formulae 5-1 to 5-7,
$R_a$, $R_b$, $L_1$, $L_2$, $X_1$ to $X_3$, $Ar_1$, and $Ar_2$ are as defined in claim 1.

13. The compound according to claim 1, wherein the compound is any one selected from the group consisting of the following compounds:
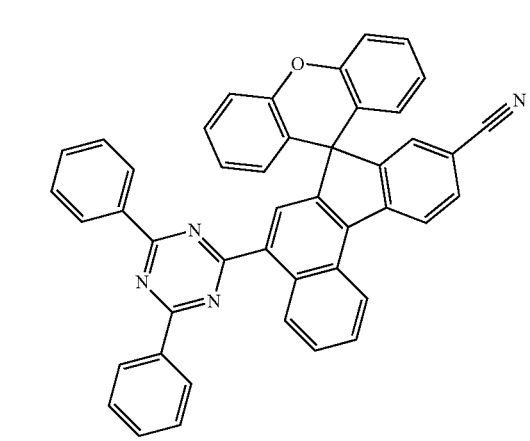
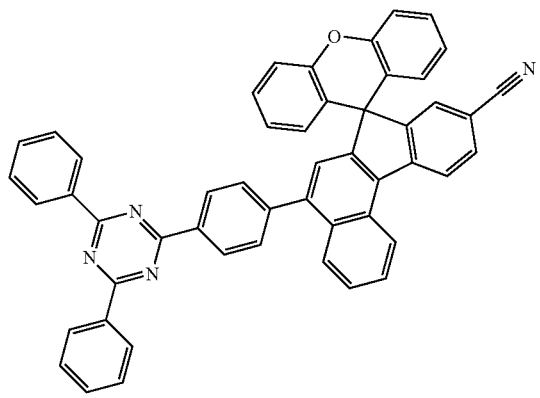
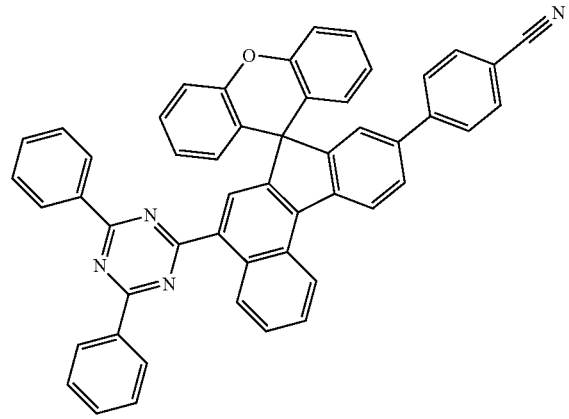
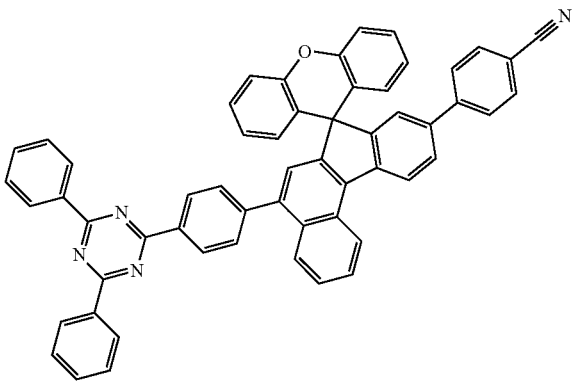
-continued
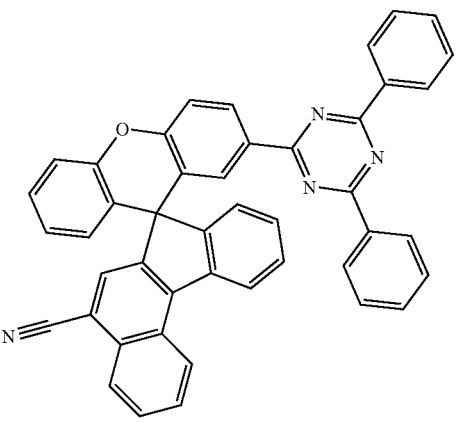
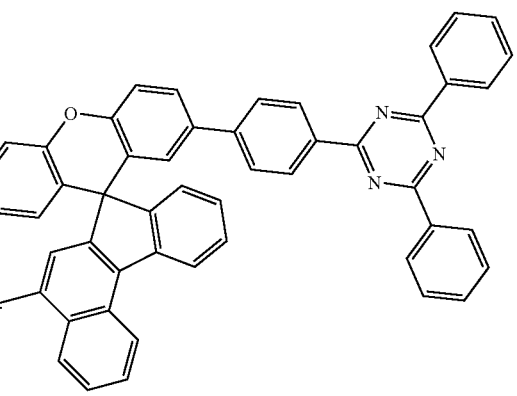

85
-continued
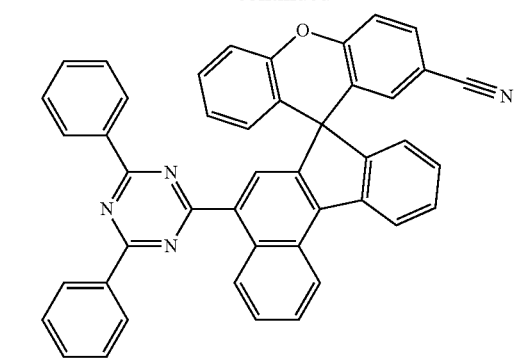
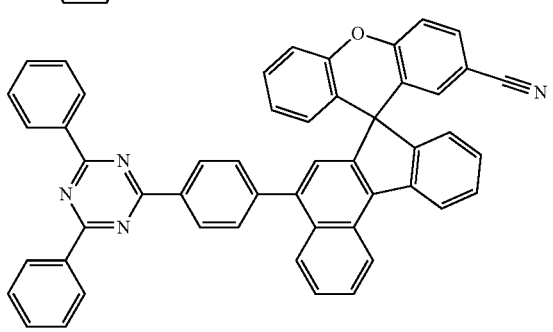
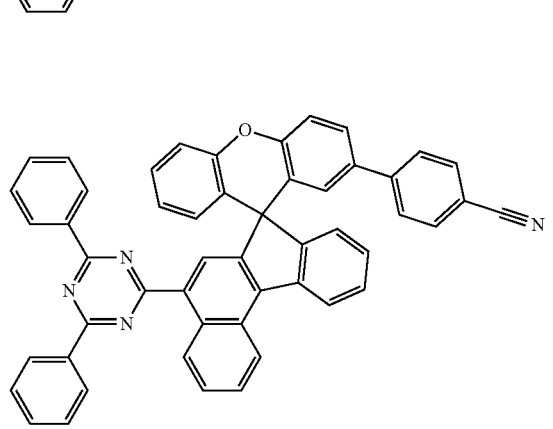
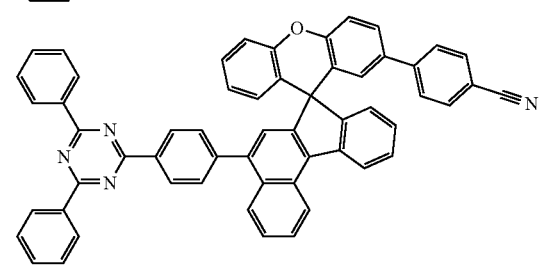
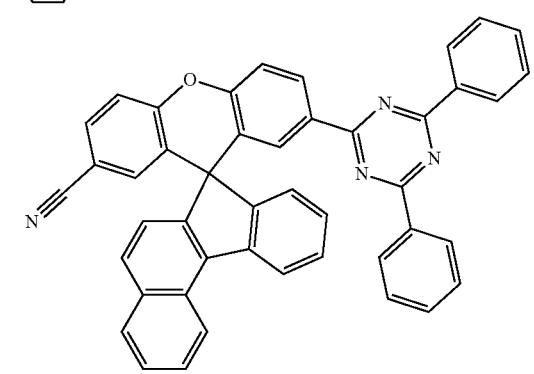
86
-continued
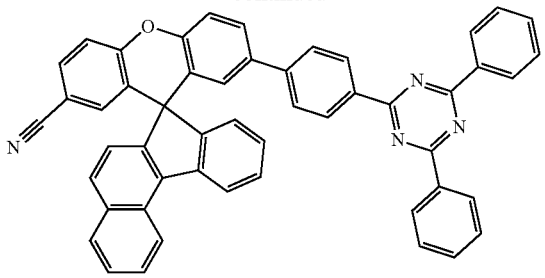
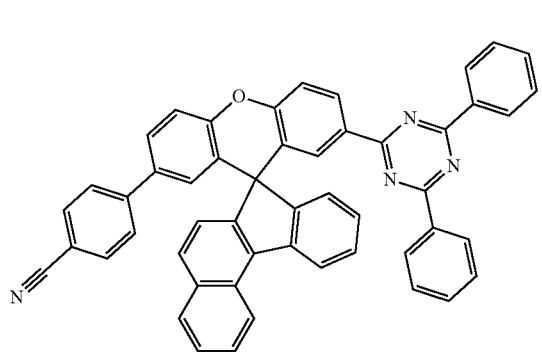
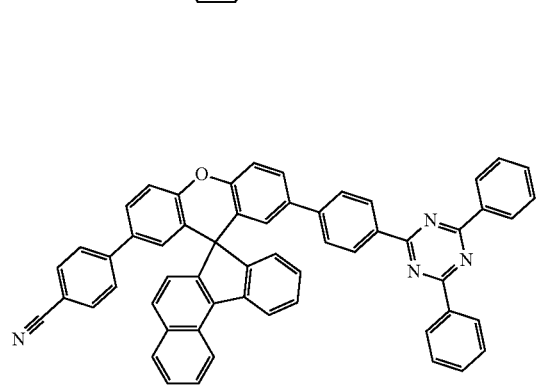

87
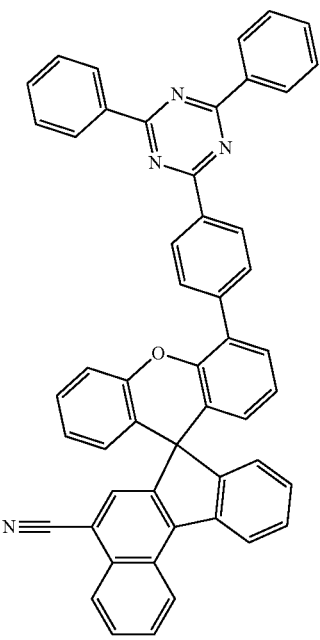
88
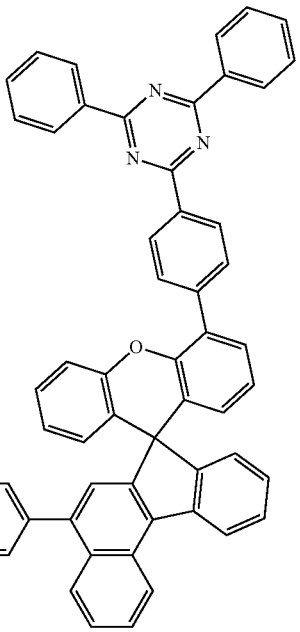
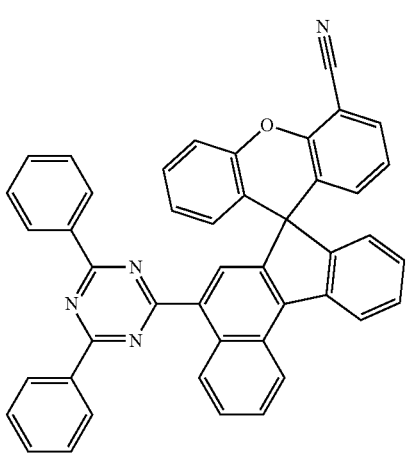
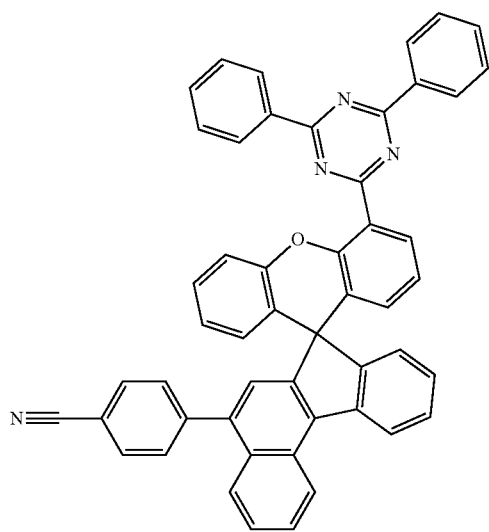

89
-continued
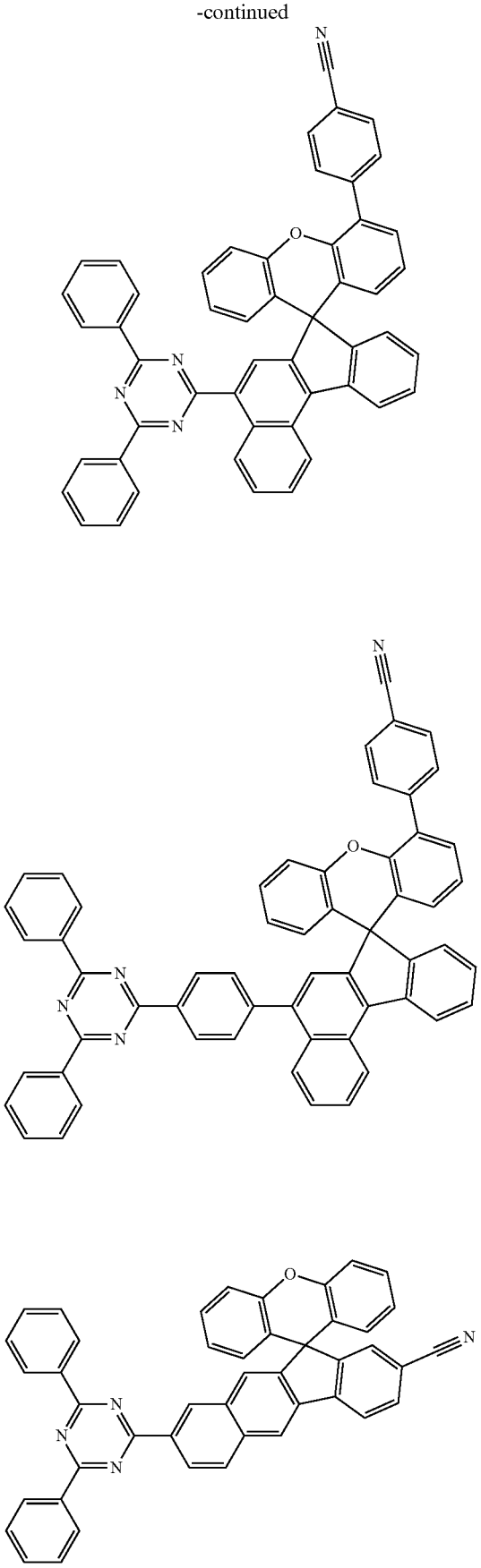
90
-continued
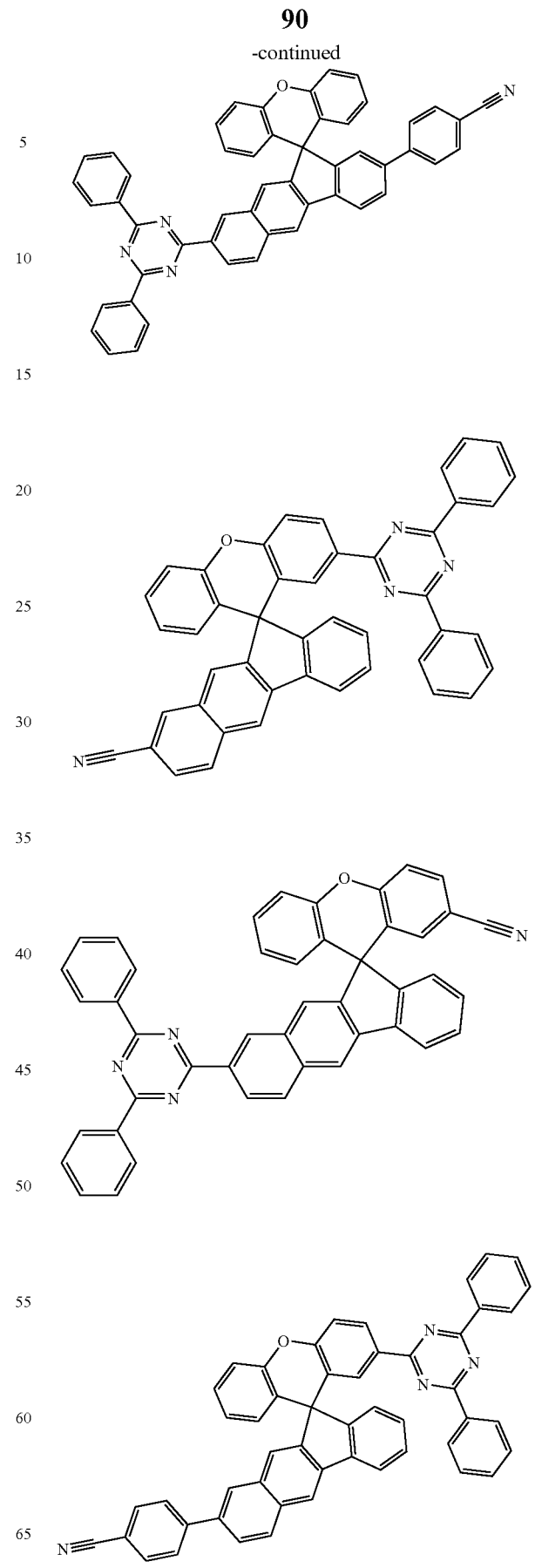

-continued
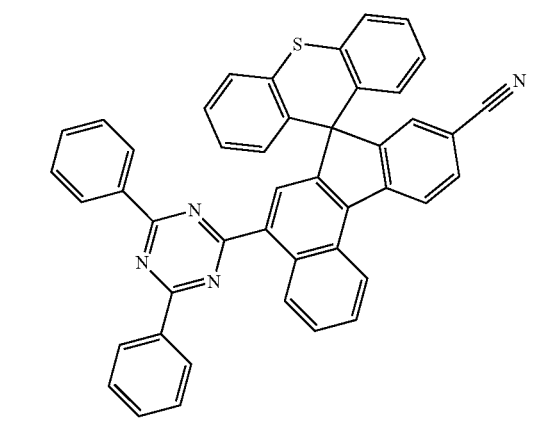
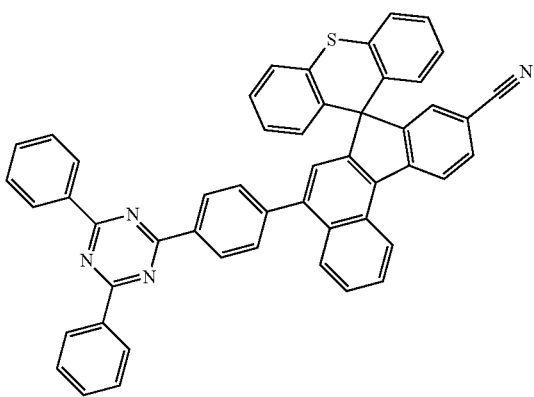
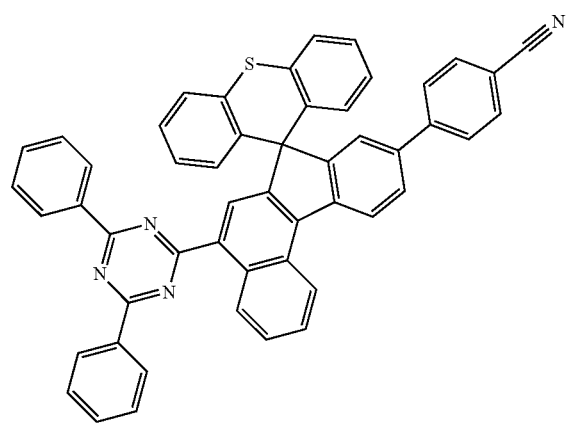
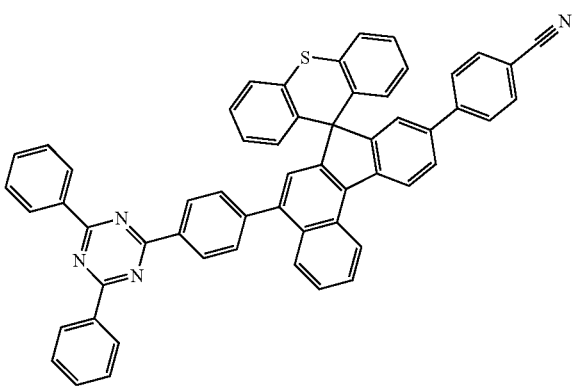
-continued
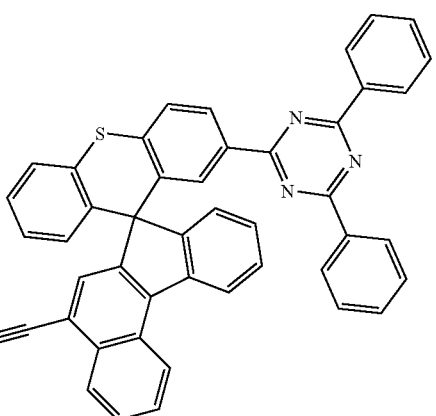
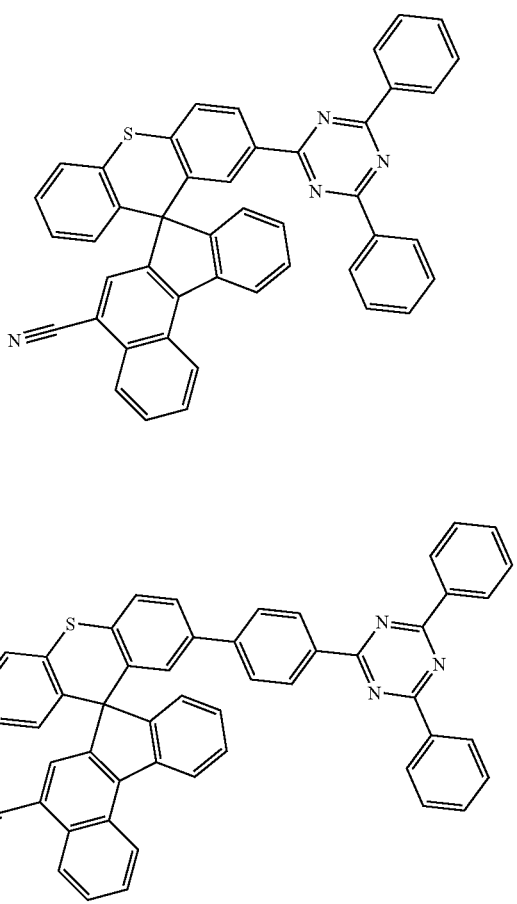
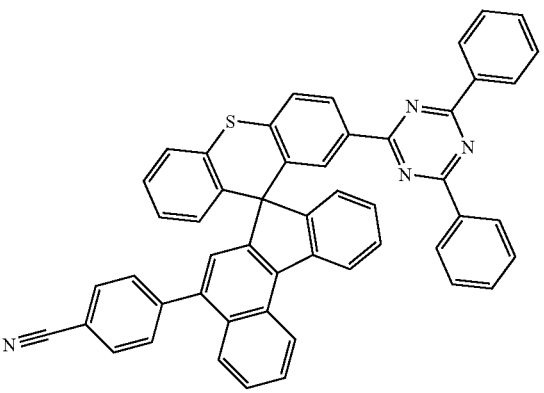
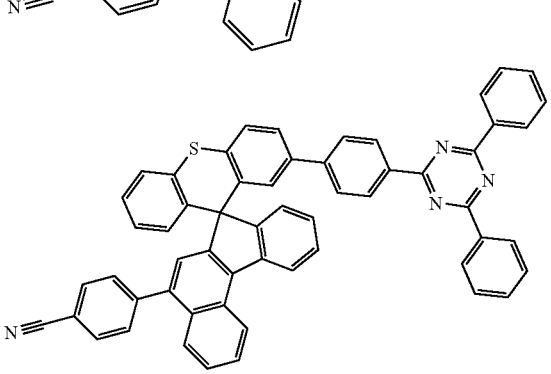

93
-continued
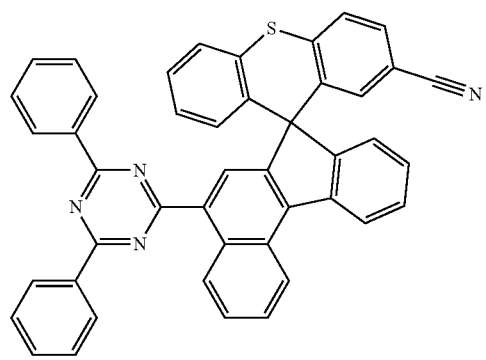
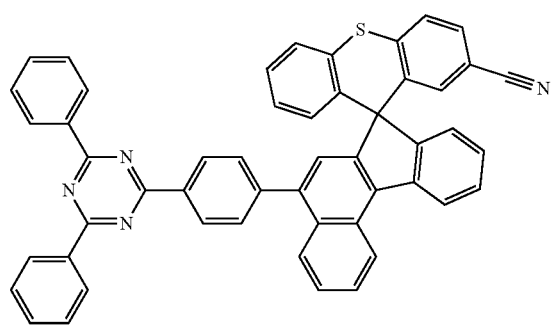
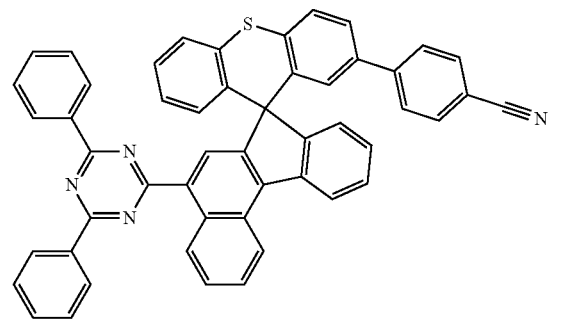
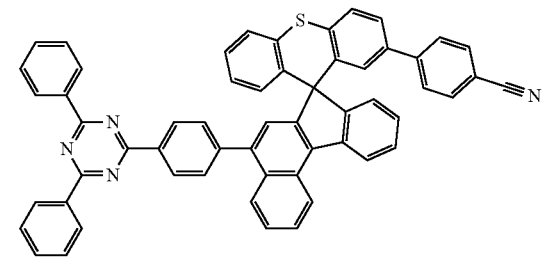
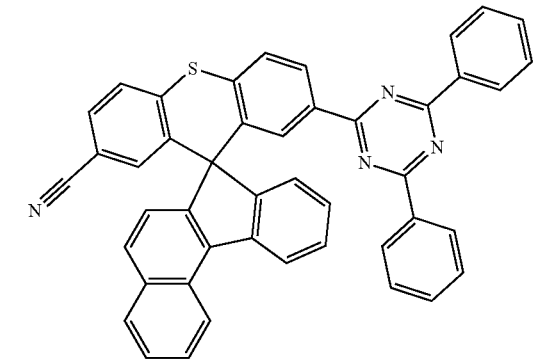
94
-continued
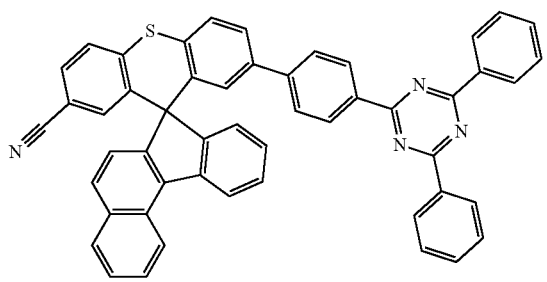
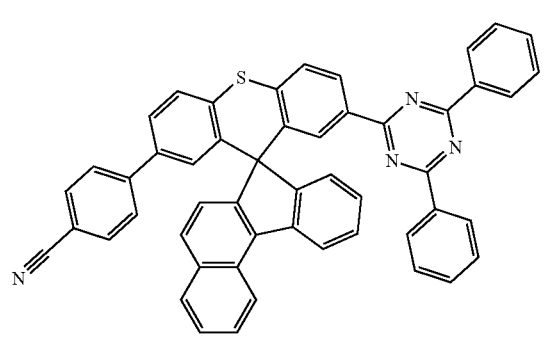
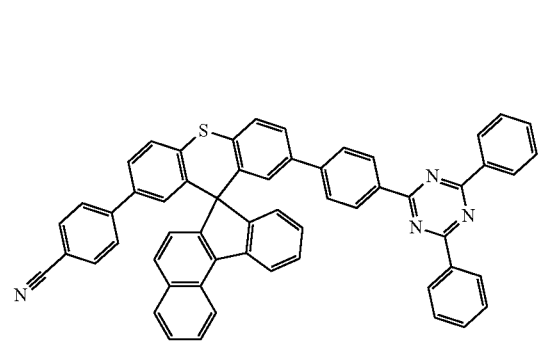
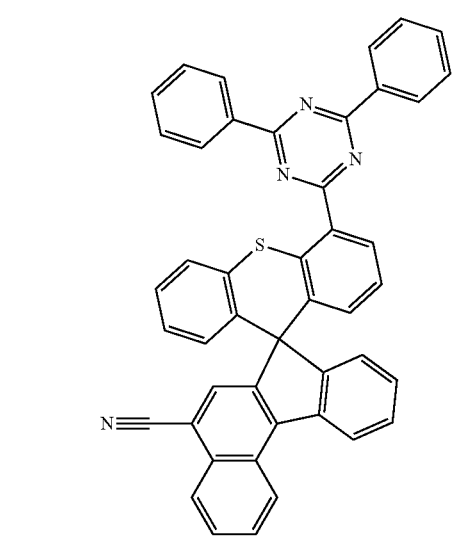

95
-continued
96
-continued
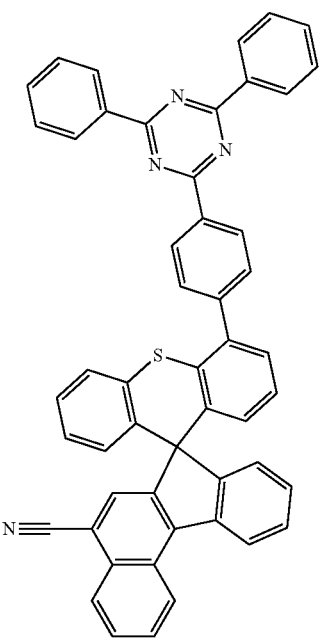
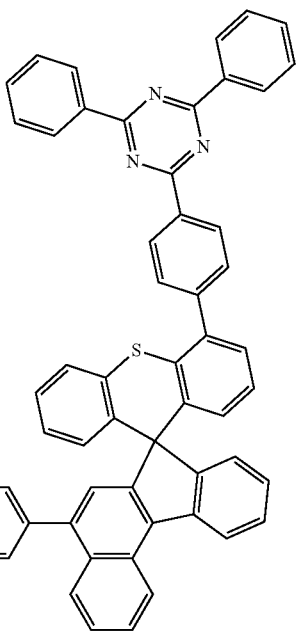
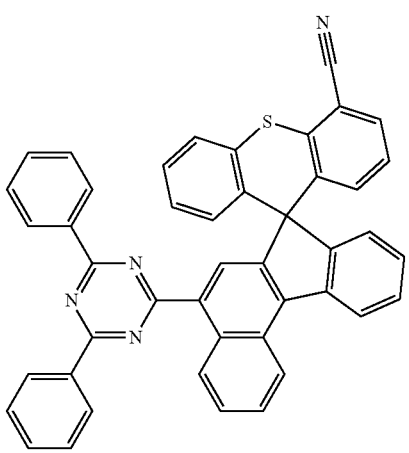
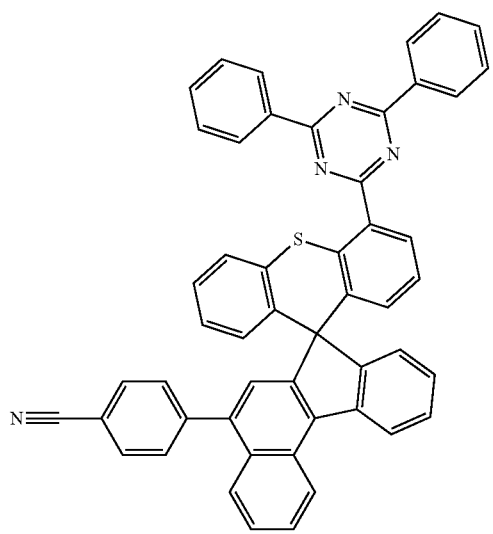

97
-continued
98
-continued
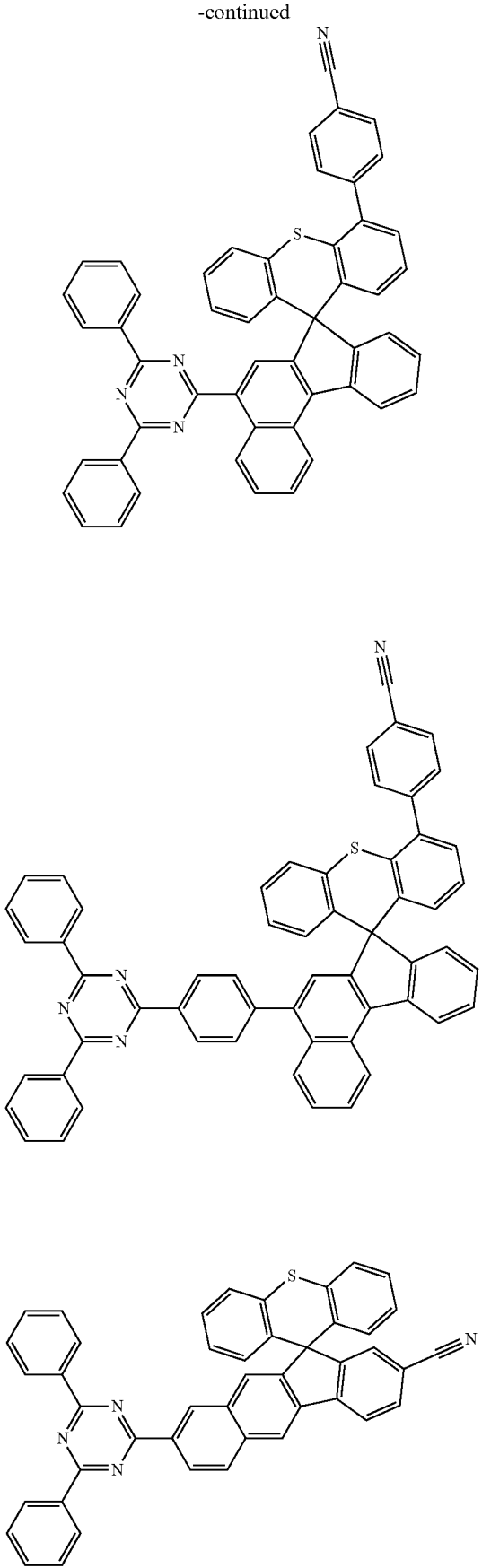
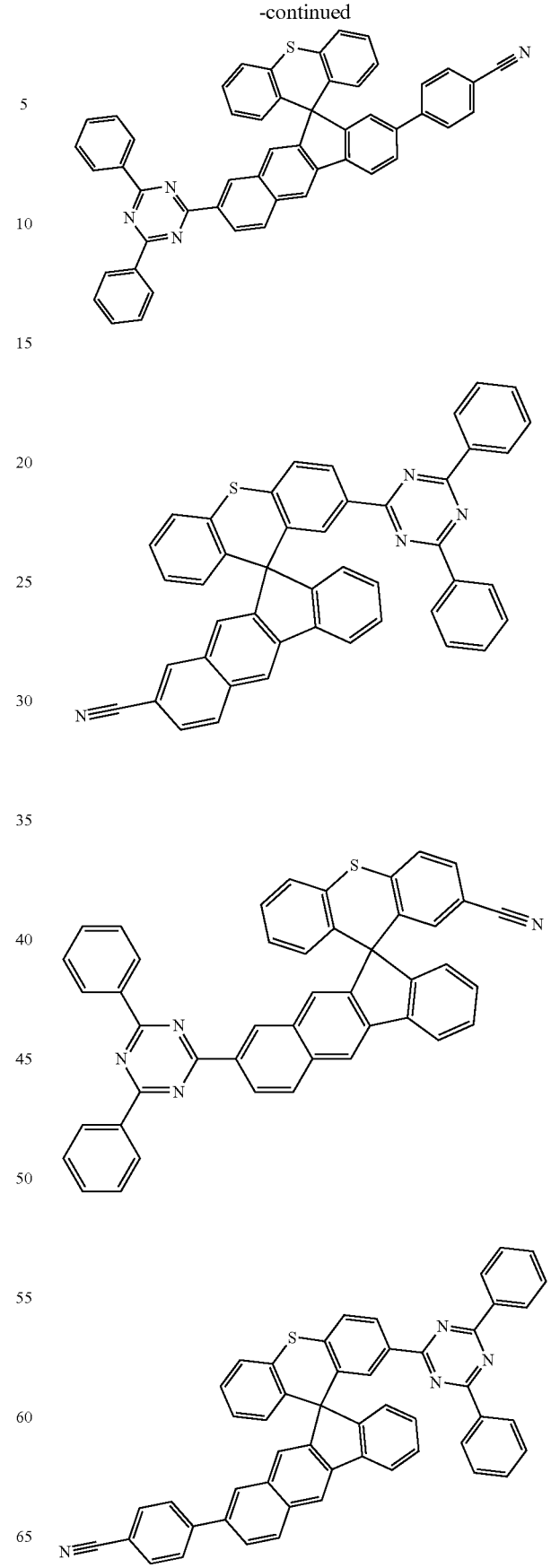

99
-continued
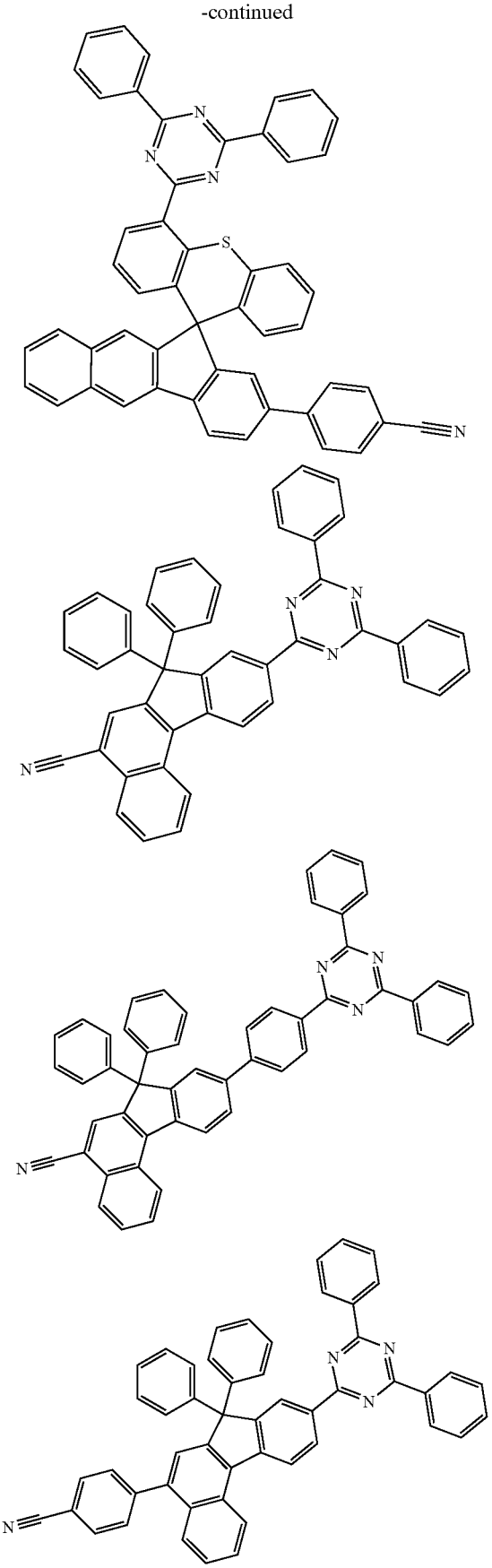
100
-continued
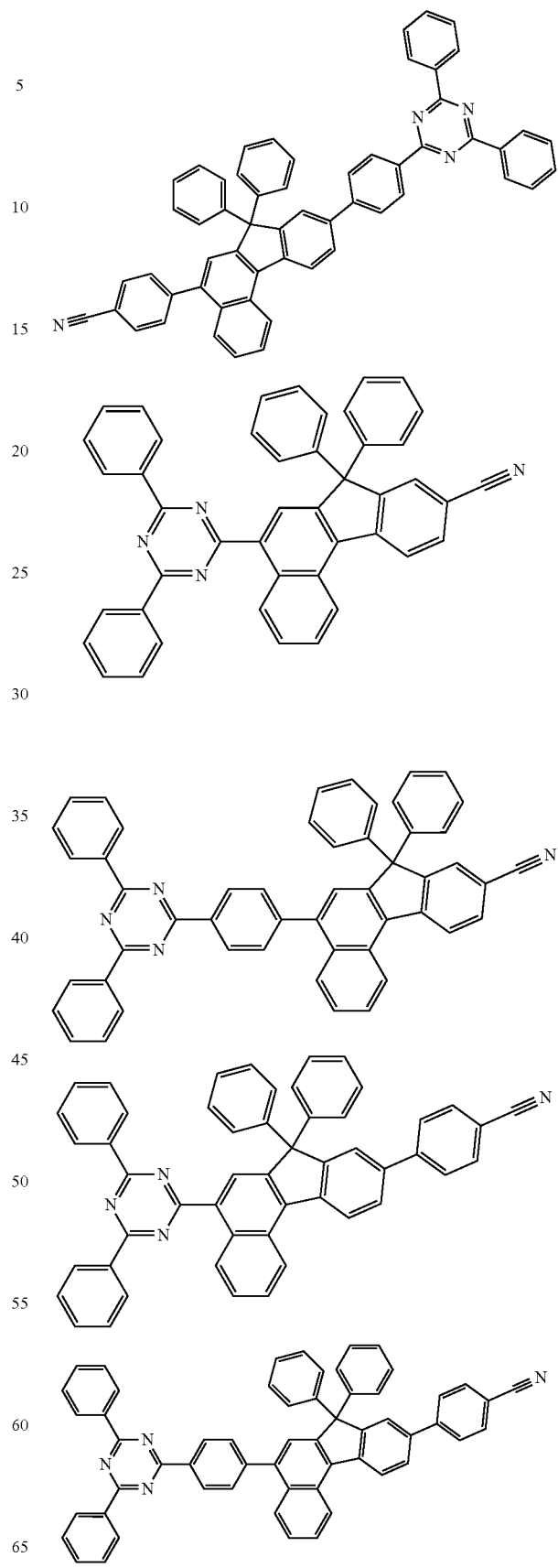

101
-continued
102
-continued
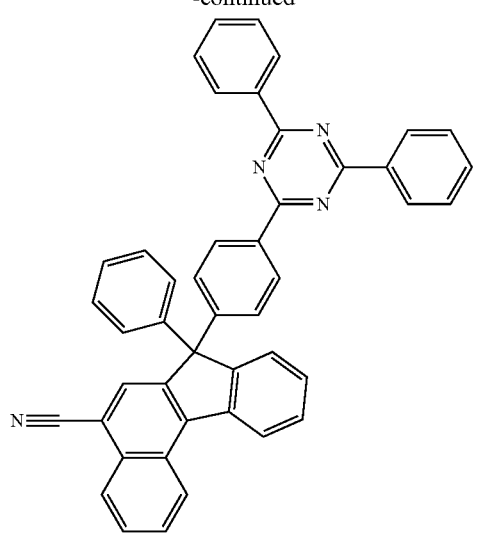
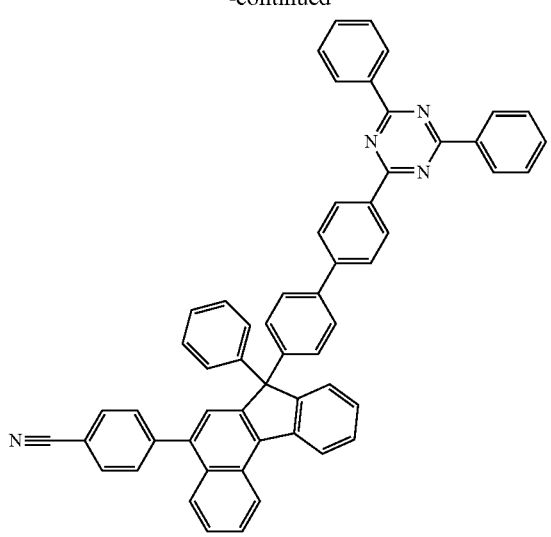
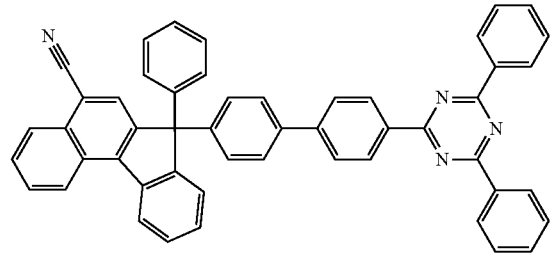
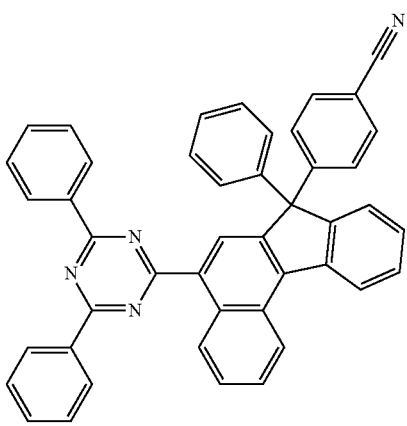
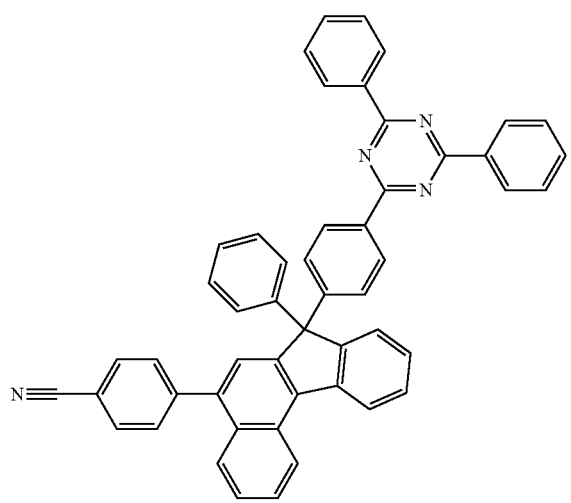
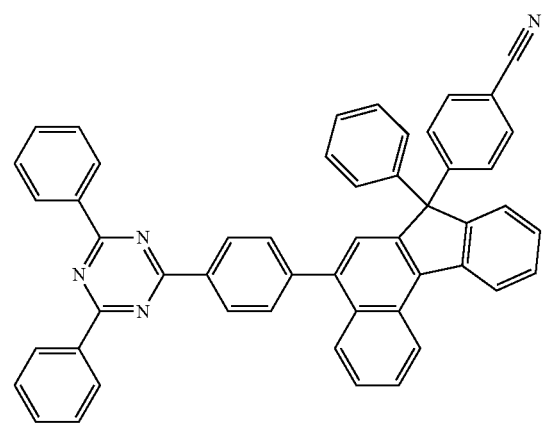

103
-continued
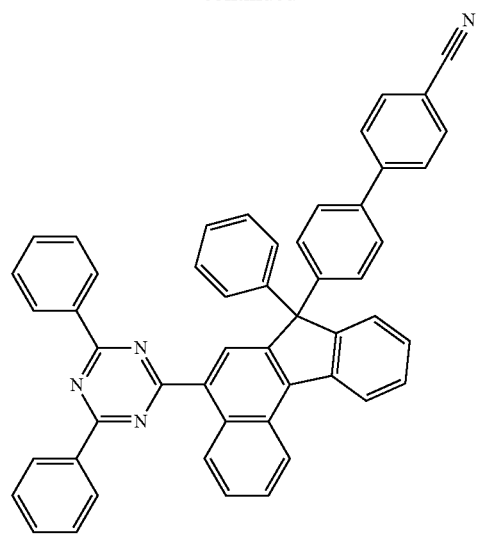
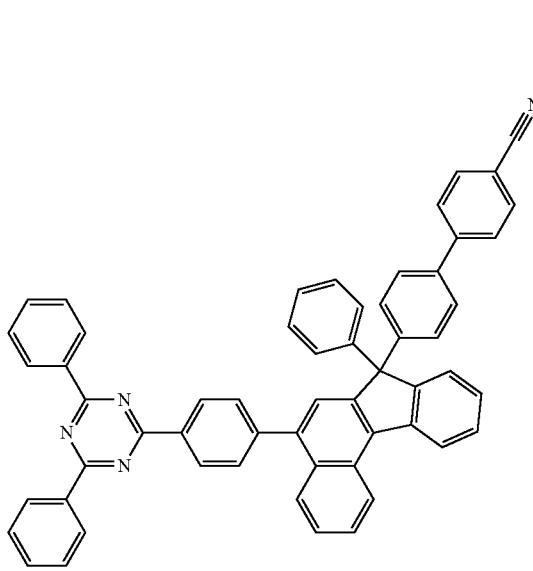
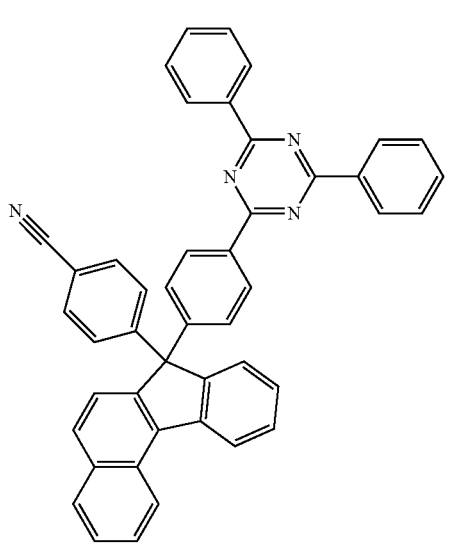
104
-continued
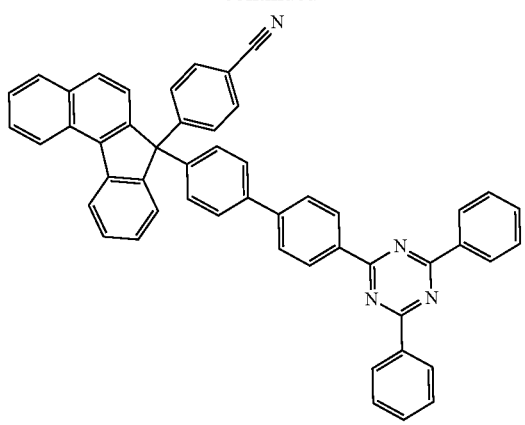
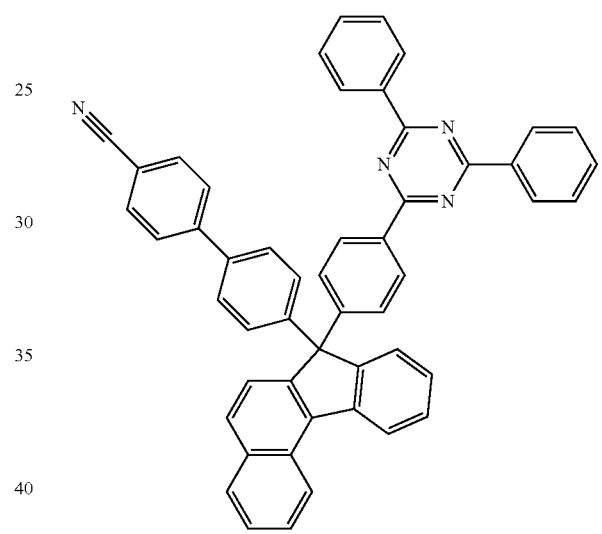
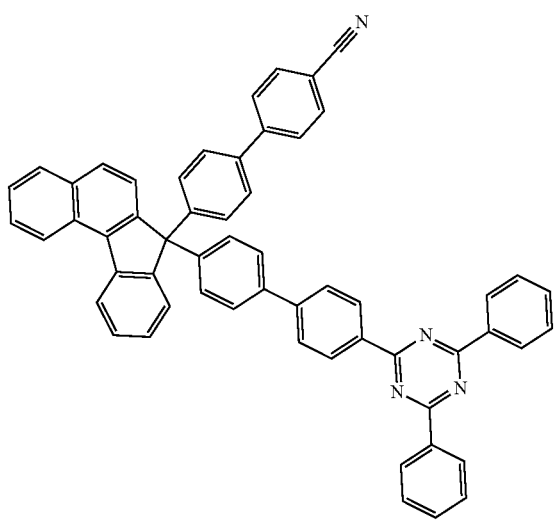

105
-continued
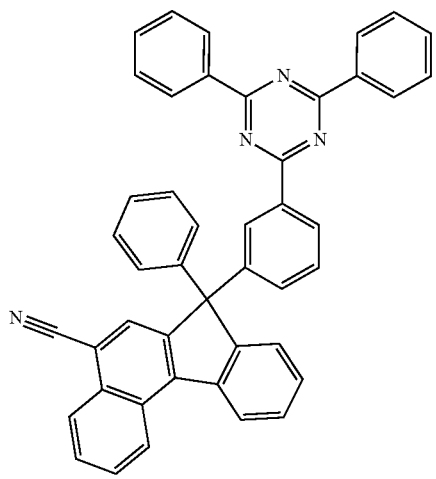
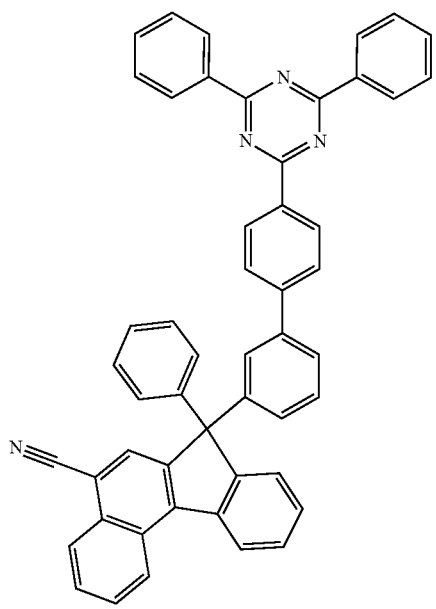
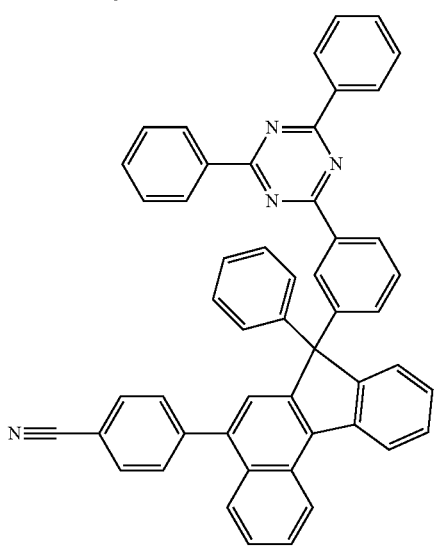
106
-continued
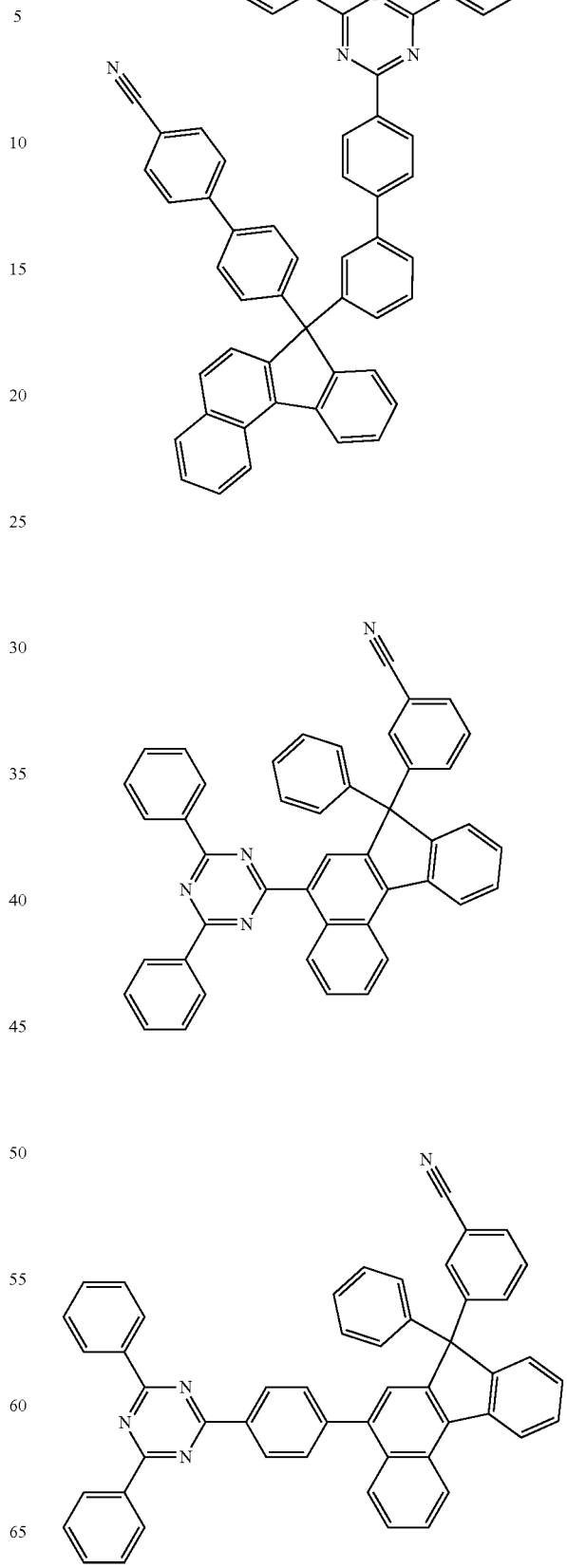

107
-continued
108
-continued
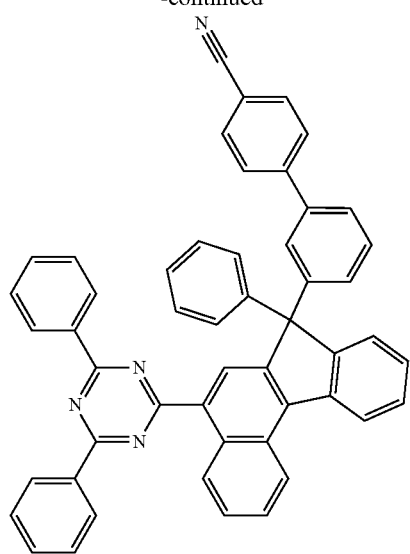
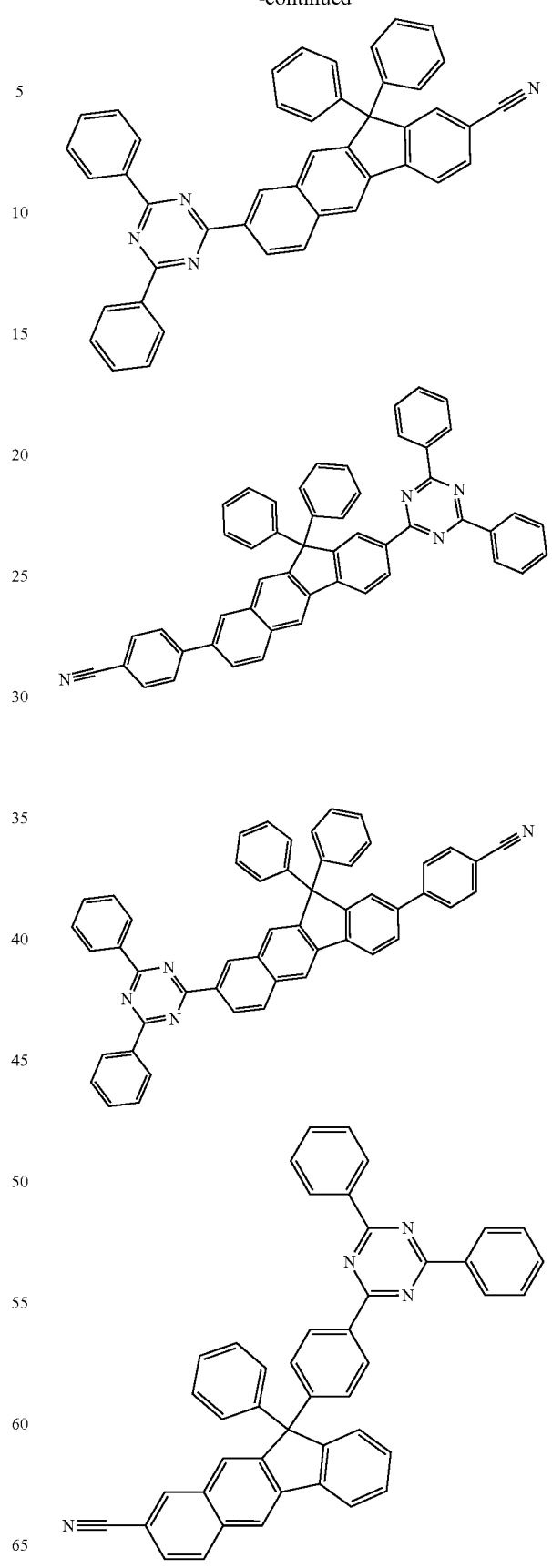

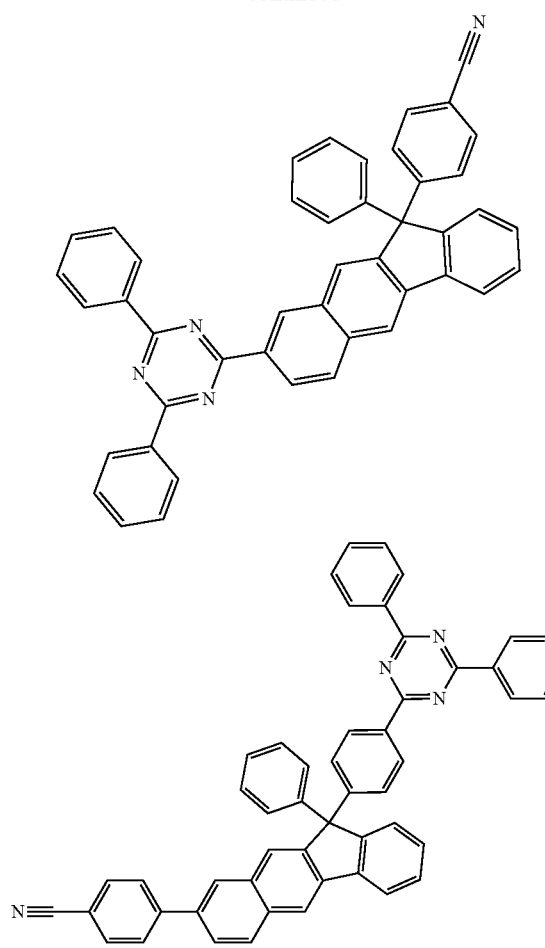
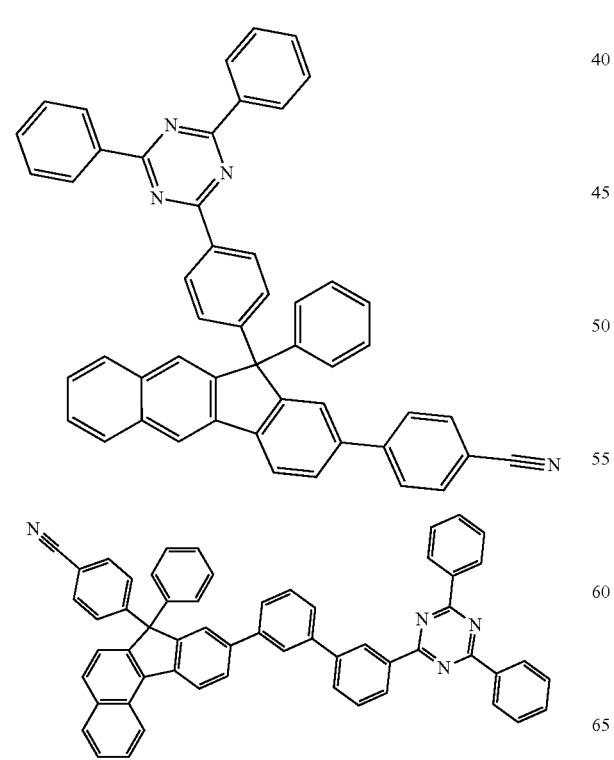
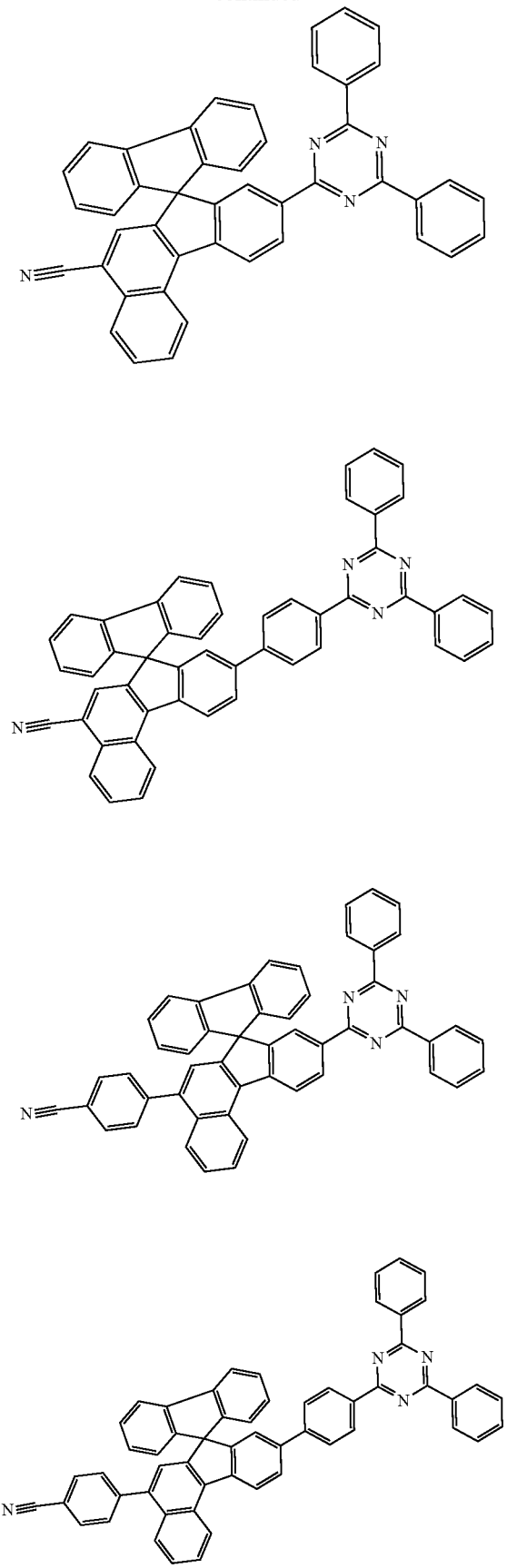

111
-continued
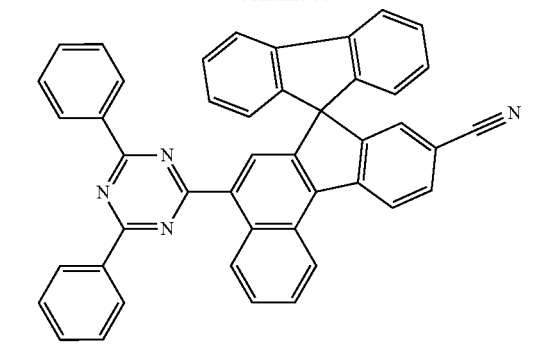
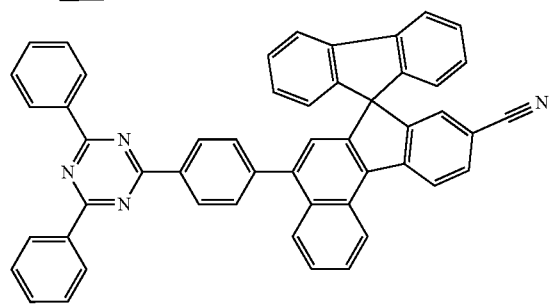
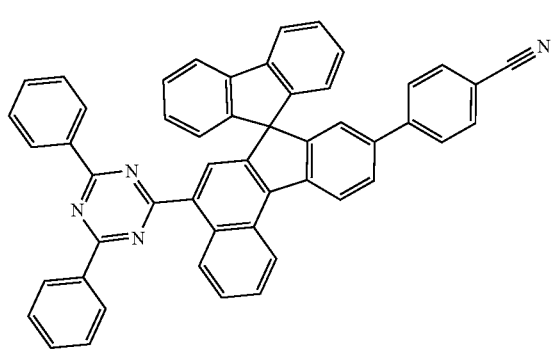
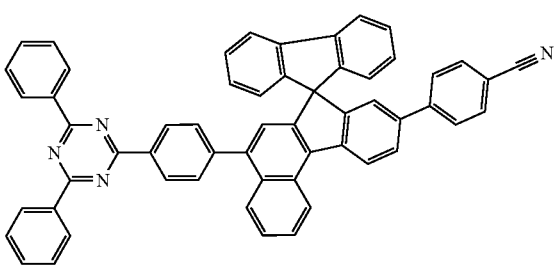
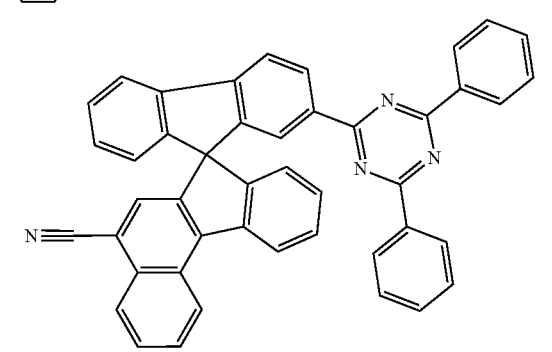
112
-continued
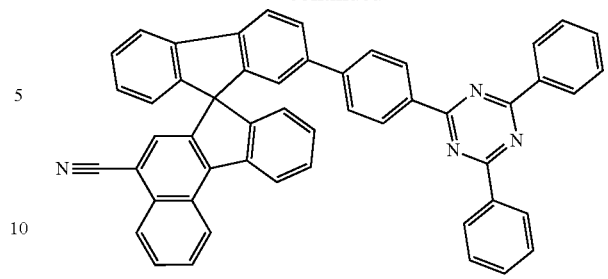
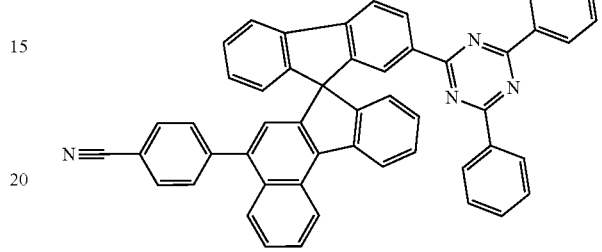
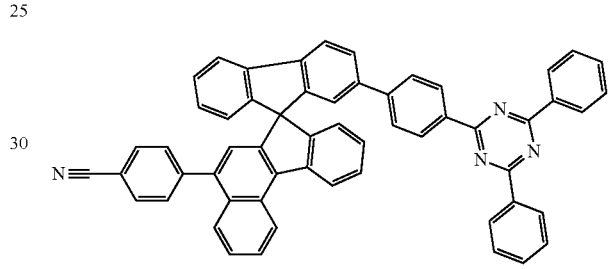
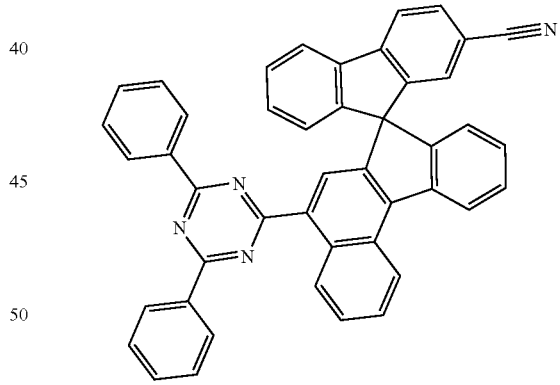
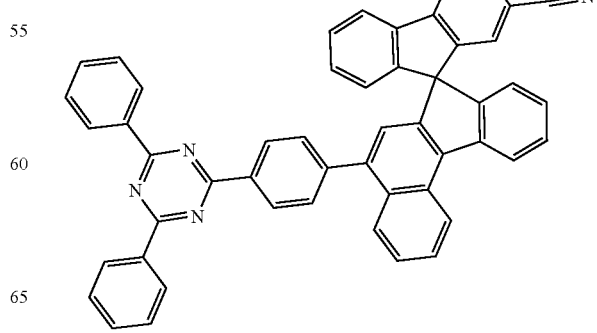

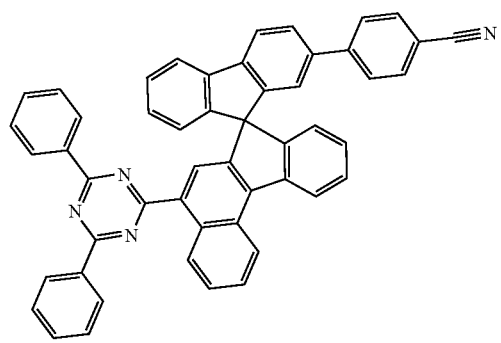
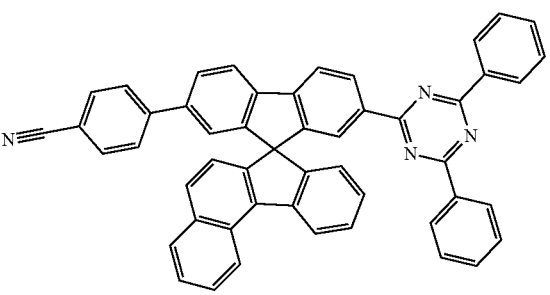

115
-continued
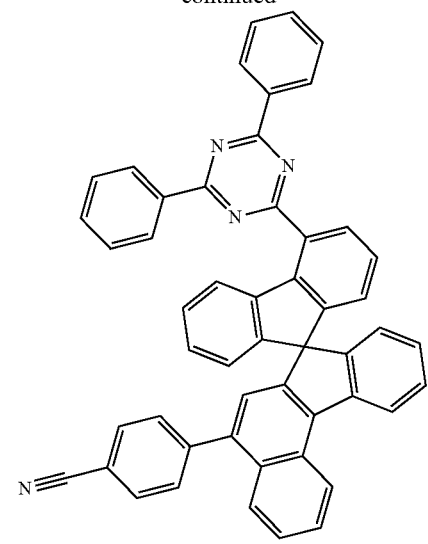
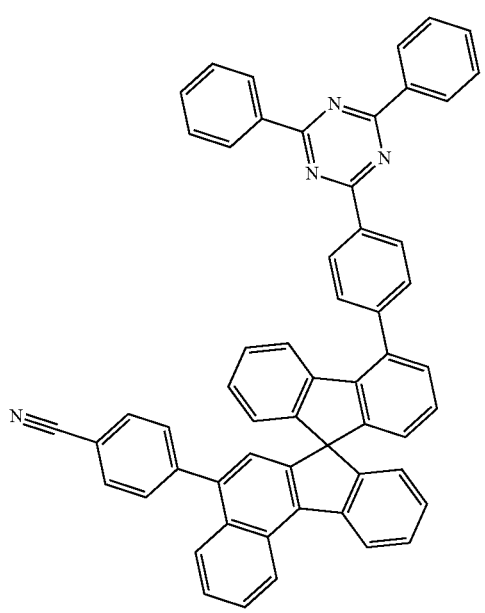
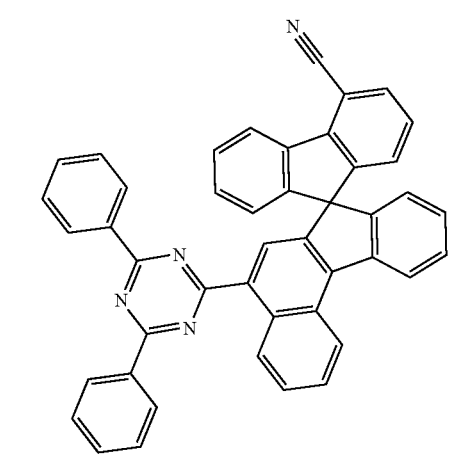
116
-continued
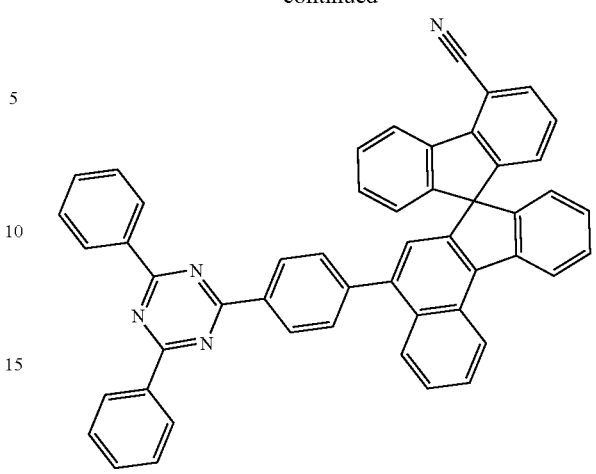
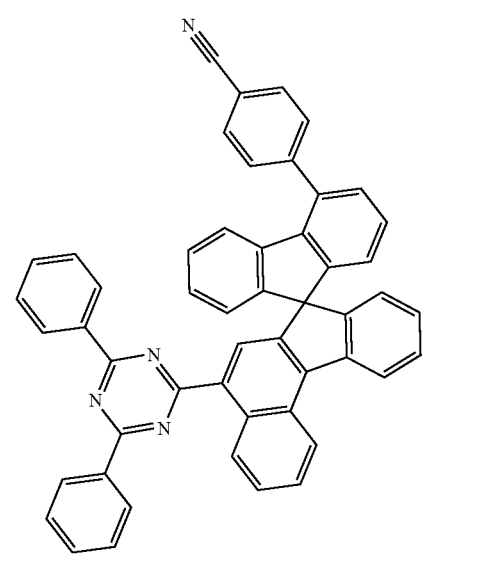
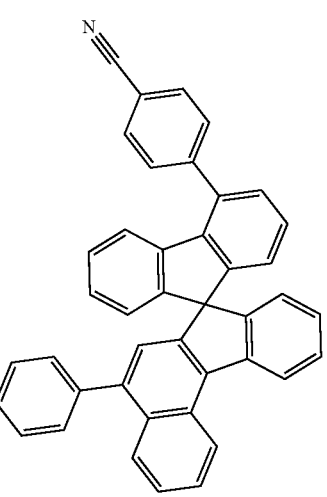

117
-continued
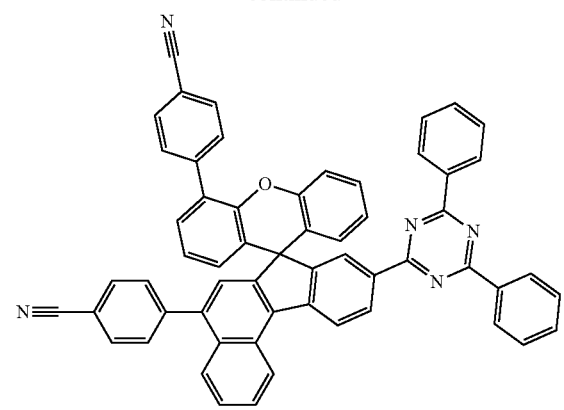
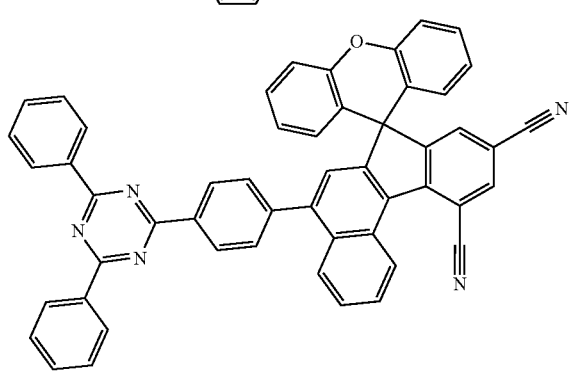
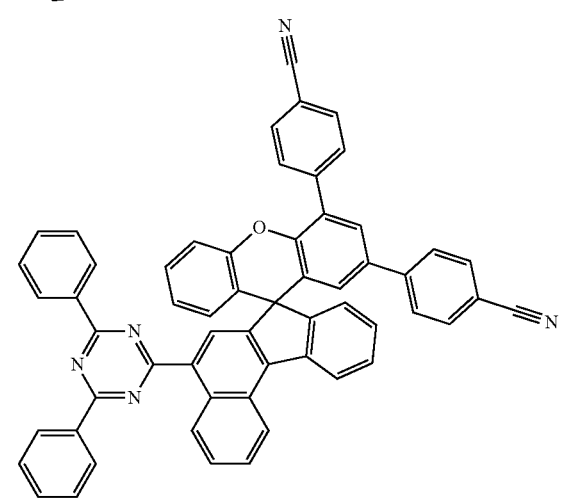
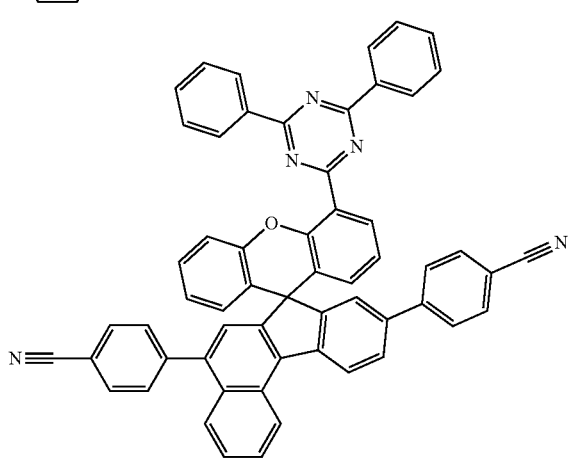
118
-continued
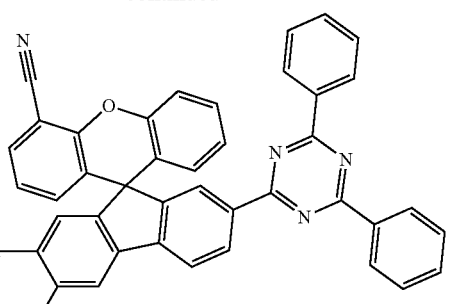
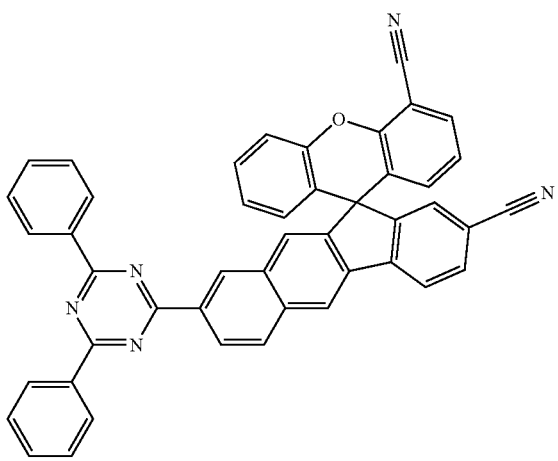
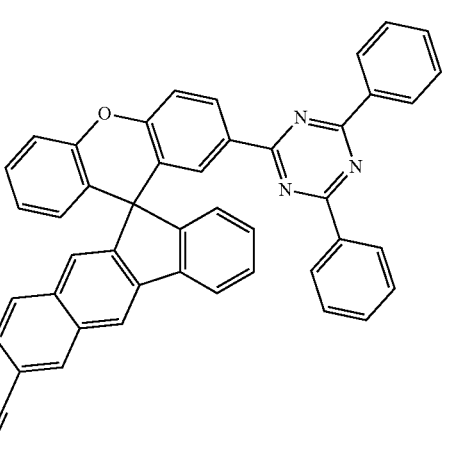
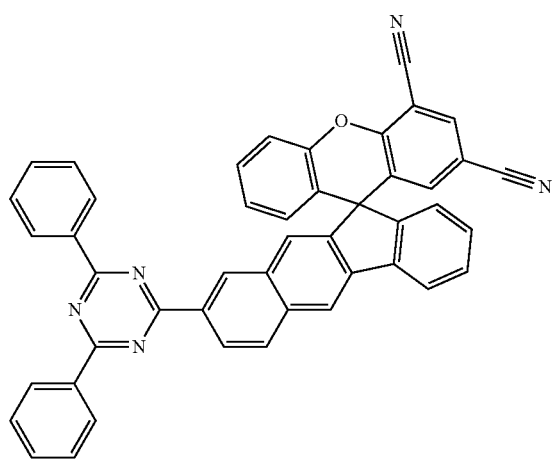

119
-continued
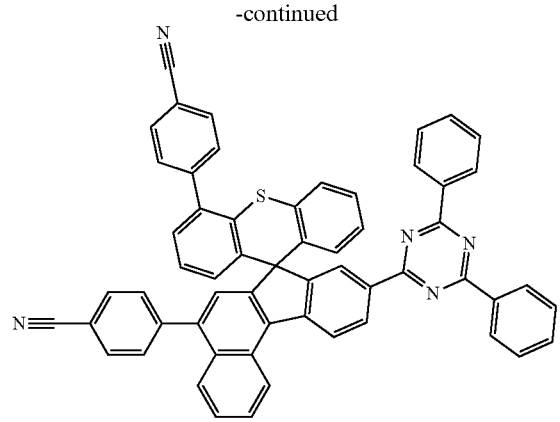
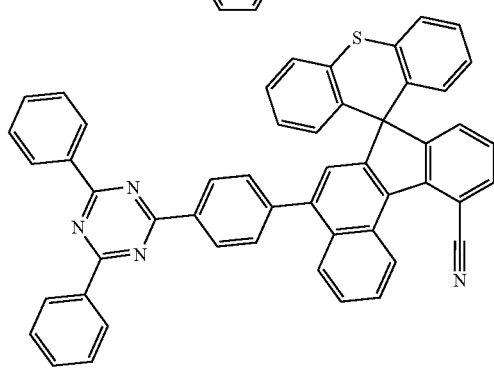
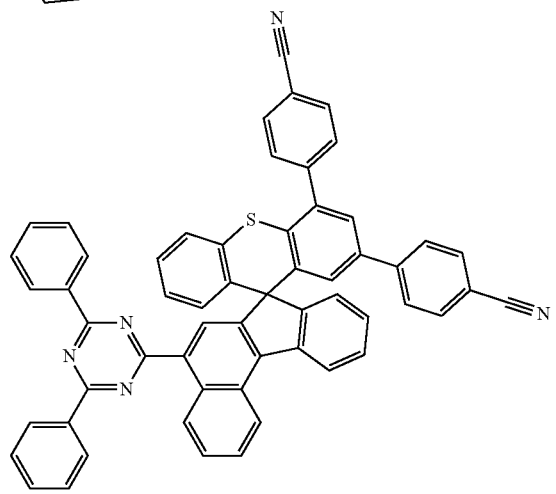
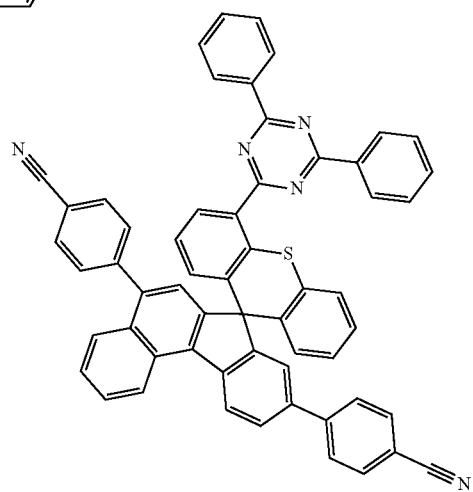
120
-continued
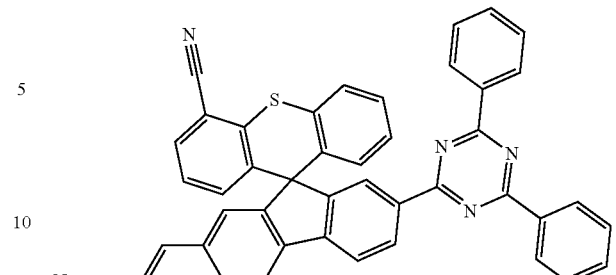
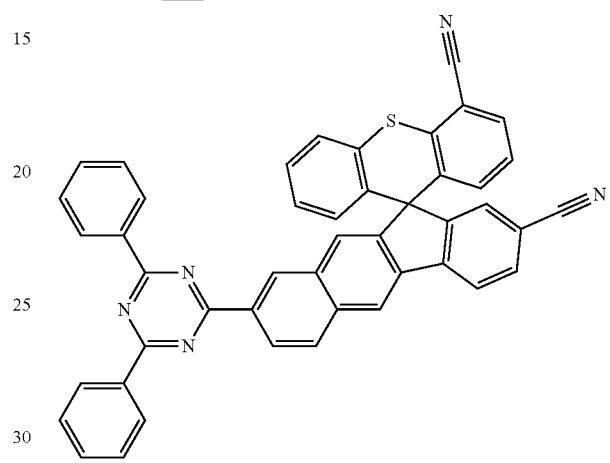
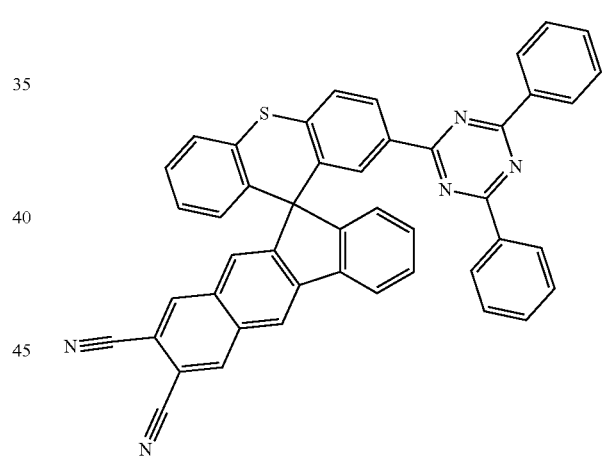
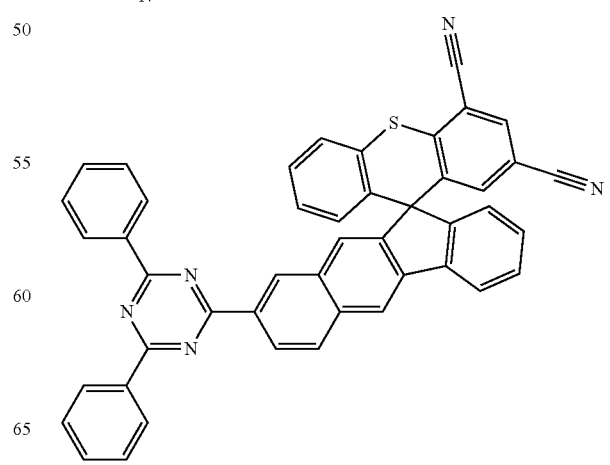

121
-continued
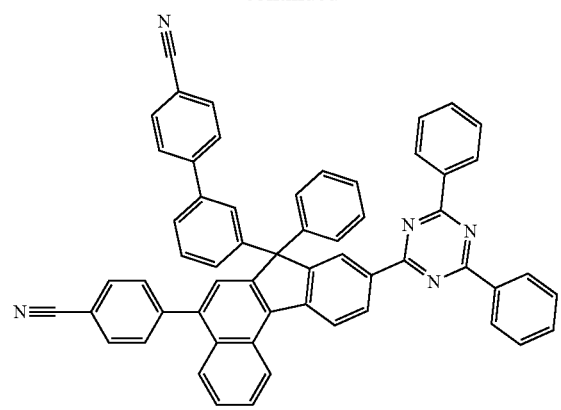
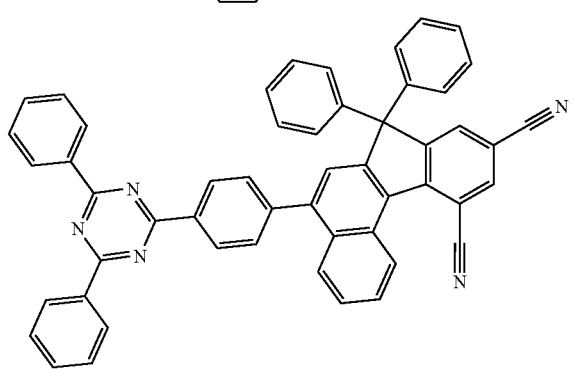
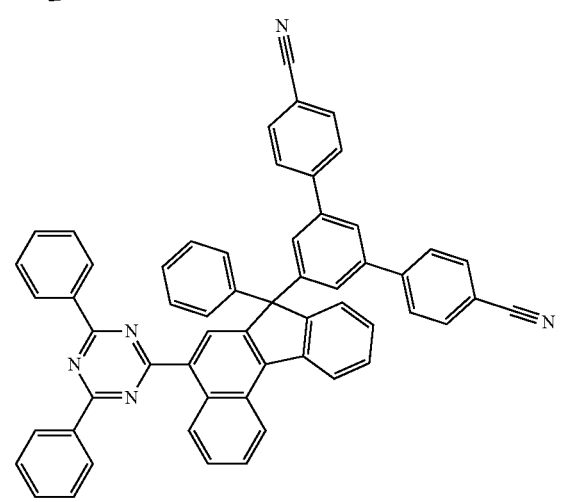
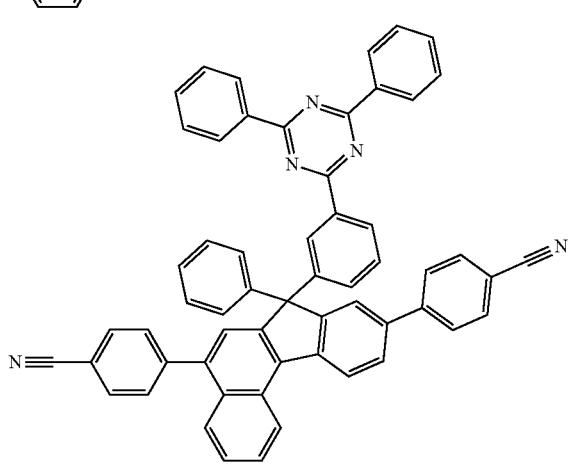
122
-continued
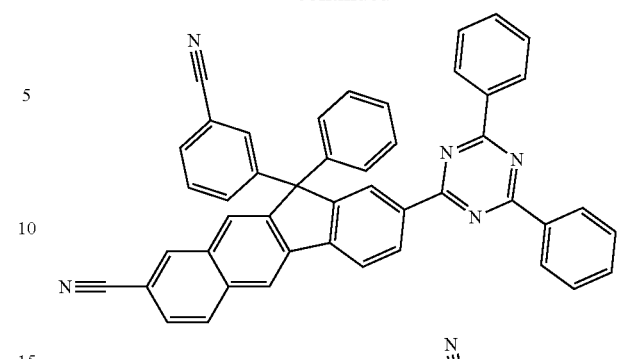
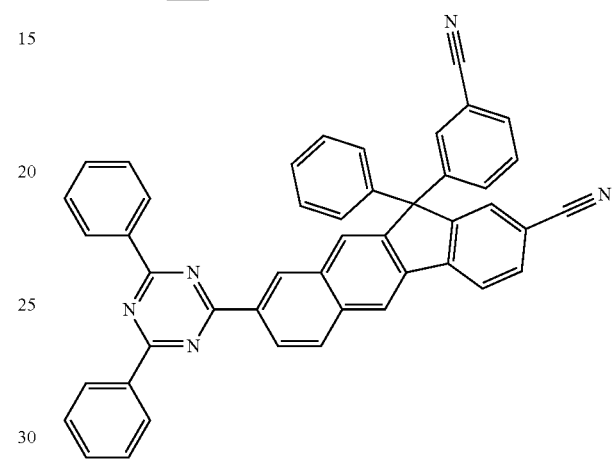
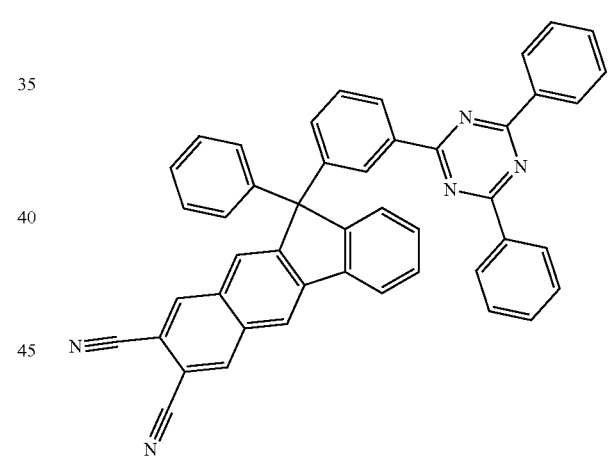
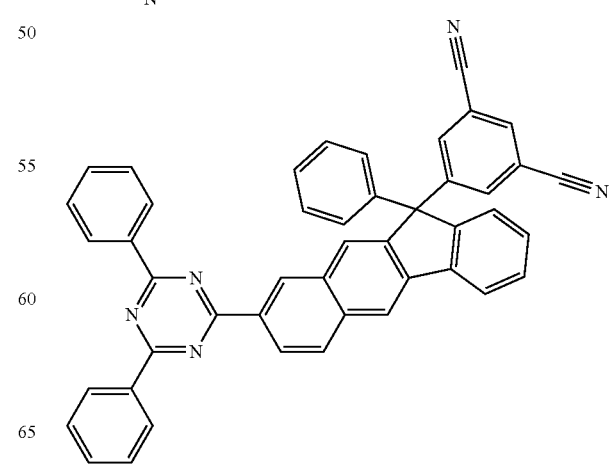

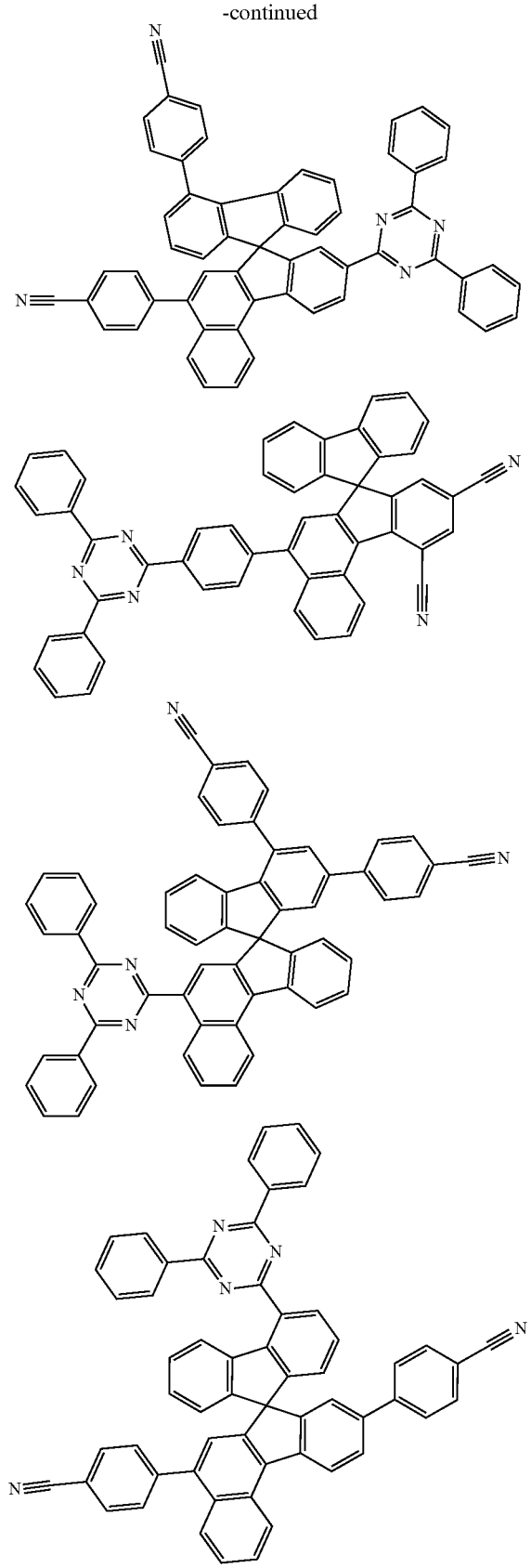
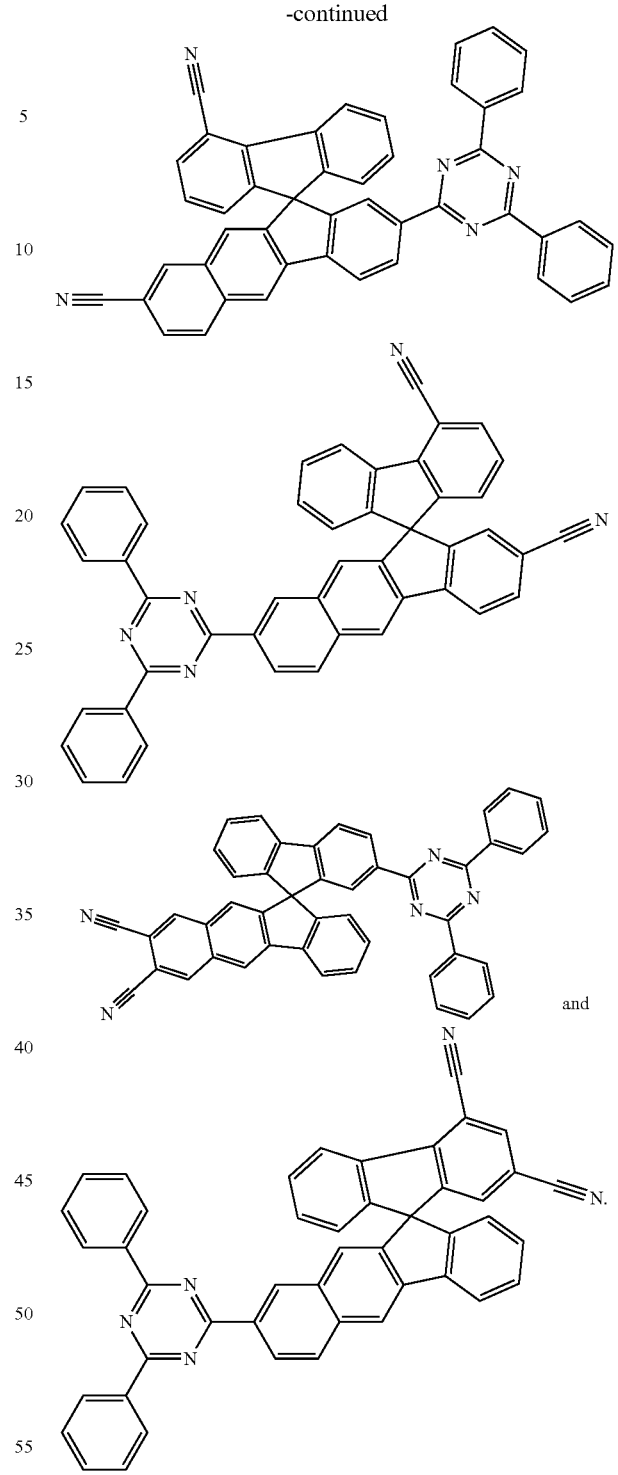
14. An organic light emitting device comprising: a first electrode; a second electrode provided to face the first electrode; and at least one layer of the organic material layers provided between the first electrode and the second electrode, wherein one or more layers of the organic material layers comprise the compound according to claim 1.
* * * * *